(12) United States Patent
Foley et al.

(10) Patent No.: US 8,206,299 B2
(45) Date of Patent: *Jun. 26, 2012

(54) IMAGE GUIDED HIGH INTENSITY FOCUSED ULTRASOUND TREATMENT OF NERVES

(75) Inventors: Jessica L. Foley, Seattle, WA (US); Shahram Vaezy, Seattle, WA (US); James W. Little, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/887,211

(22) Filed: Sep. 21, 2010

(65) Prior Publication Data

US 2011/0009734 A1 Jan. 13, 2011

Related U.S. Application Data

(60) Continuation of application No. 12/390,975, filed on Feb. 23, 2009, which is a division of application No. 11/016,701, filed on Dec. 16, 2004, now Pat. No. 7,510,536.

(60) Provisional application No. 60/529,916, filed on Dec. 16, 2003.

(51) Int. Cl.
*A61B 8/00* (2006.01)
*A61H 1/00* (2006.01)
(52) U.S. Cl. ........................................... 600/439; 601/2
(58) Field of Classification Search ........ 601/2; 600/411, 600/437, 439
See application file for complete search history.

(56) References Cited

U.S. PATENT DOCUMENTS

| 385,256 A | 6/1888 | Eggers | |
|---|---|---|---|
| 2,992,553 A | 7/1961 | Joy | 73/644 |
| 4,059,098 A | 11/1977 | Murdock | 73/644 |

(Continued)

FOREIGN PATENT DOCUMENTS

DE 04230415 3/1994

(Continued)

OTHER PUBLICATIONS

Aaslid et al., "Noninvasive transcranial Doppler ultrasound recording of flow velocity in basal cerebral arteries."*Journal of Neurosurgery*, vol. 57: 769-774, 1982.

(Continued)

*Primary Examiner* — Michael Rozanski
(74) *Attorney, Agent, or Firm* — King & Spalding LLP; Peter J. Dehlinger

(57) ABSTRACT

A method for using high intensity focused ultrasound (HIFU) to treat neurological structures to achieve a desired therapeutic effect. Depending on the dosage of HIFU applied, it can have a reversible or irreversible effect on neural structures. For example, a relatively high dose of HIFU can be used to permanently block nerve function, to provide a non-invasive alternative to severing a nerve to treat severe spasticity. Relatively lower doses of HIFU can be used to reversibly block nerve function, to alleviate pain, to achieve an anesthetic effect, or to achieve a cosmetic effect. Where sensory nerves are not necessary for voluntary function, but are involved in pain associated with tumors or bone cancer, HIFU can be used to non-invasively destroy such sensory nerves to alleviate pain without drugs. Preferably, ultrasound imaging synchronized to the HIFU therapy is used to provide real-time ultrasound image guided HIFU therapy of neural structures.

9 Claims, 36 Drawing Sheets

U.S. PATENT DOCUMENTS

| | | | |
|---|---|---|---|
| 4,484,569 A | 11/1984 | Driller et al. | 128/60 |
| 4,545,386 A | 10/1985 | Hetz et al. | 600/462 |
| 4,601,296 A | 7/1986 | Yerushalmi | 607/156 |
| 4,688,578 A | 8/1987 | Takano et al. | 600/459 |
| RE33,590 E | 5/1991 | Dory | 128/999.999 |
| 5,039,774 A | 8/1991 | Shikinami et al. | 528/60 |
| 5,065,742 A | 11/1991 | Belikan et al. | 128/24 |
| 5,080,101 A | 1/1992 | Dory | 128/999.999 |
| 5,080,102 A | 1/1992 | Dory | 128/999.999 |
| 5,088,498 A | 2/1992 | Beach et al. | 600/453 |
| 5,150,712 A | 9/1992 | Dory | 128/999.999 |
| 5,170,790 A | 12/1992 | Lacoste et al. | 600/437 |
| 5,178,148 A | 1/1993 | Lacoste et al. | 600/439 |
| 5,183,046 A | 2/1993 | Beach et al. | 600/453 |
| 5,215,680 A | 6/1993 | D'Arrigo | 516/11 |
| 5,219,401 A | 6/1993 | Cathignol et al. | 128/999.999 |
| 5,230,334 A | 7/1993 | Klopotek | 128/999.999 |
| 5,289,820 A | 3/1994 | Beach et al. | 600/443 |
| 5,311,869 A | 5/1994 | Okazaki | 128/999.999 |
| 5,391,140 A | 2/1995 | Schaetzle et al. | 601/4 |
| 5,394,877 A | 3/1995 | Orr et al. | 600/459 |
| 5,471,988 A | 12/1995 | Fujio et al. | 128/999.999 |
| 5,474,071 A | 12/1995 | Chapelon et al. | 600/439 |
| 5,492,126 A | 2/1996 | Hennige et al. | 600/439 |
| 5,507,790 A | 4/1996 | Weiss | 607/100 |
| 5,520,188 A | 5/1996 | Hennige et al. | 128/999.999 |
| 5,522,878 A | 6/1996 | Montecalvo et al. | 607/152 |
| 5,526,815 A | 6/1996 | Granz et al. | 128/999.999 |
| 5,536,489 A | 7/1996 | Lohrmann et al. | 424/9.52 |
| 5,558,092 A | 9/1996 | Unger et al. | 128/999.999 |
| 5,573,497 A | 11/1996 | Chapelon | 601/2 |
| 5,609,485 A | 3/1997 | Bergman et al. | 434/262 |
| 5,638,823 A | 6/1997 | Akay et al. | 600/528 |
| 5,657,760 A | 8/1997 | Ying et al. | 128/999.999 |
| 5,666,954 A | 9/1997 | Chapelon et al. | 600/439 |
| 5,720,286 A | 2/1998 | Chapelon et al. | 600/439 |
| 5,720,287 A | 2/1998 | Chapelon et al. | 600/439 |
| 5,755,228 A | 5/1998 | Wilson et al. | 600/459 |
| 5,762,066 A | 6/1998 | Law et al. | 128/999.999 |
| 5,769,790 A | 6/1998 | Watkins et al. | 600/439 |
| 5,807,285 A | 9/1998 | Vaitekunas et al. | 601/2 |
| 5,810,007 A | 9/1998 | Holupka et al. | 600/439 |
| 5,817,021 A | 10/1998 | Reichenberger | 600/439 |
| 5,823,962 A | 10/1998 | Schaetzle et al. | 600/439 |
| 5,827,204 A | 10/1998 | Grandia et al. | 601/2 |
| 5,833,647 A | 11/1998 | Edwards | 604/22 |
| 5,840,028 A | 11/1998 | Chubachi et al. | 600/437 |
| 5,846,517 A | 12/1998 | Unger | 424/9.52 |
| 5,853,752 A | 12/1998 | Unger et al. | 424/450 |
| 5,873,828 A | 2/1999 | Fujio et al. | 600/439 |
| 5,879,314 A | 3/1999 | Peterson et al. | 601/2 |
| 5,882,302 A | 3/1999 | Driscoll, Jr. et al. | 600/371 |
| 5,895,356 A | 4/1999 | Andrus et al. | 600/439 |
| 5,897,495 A | 4/1999 | Aida et al. | 600/411 |
| 5,906,580 A | 5/1999 | Kline-Schoder et al. | 600/459 |
| 5,919,139 A | 7/1999 | Lin | 600/443 |
| 5,922,945 A | 7/1999 | Allmaras et al. | 73/52 |
| 5,931,786 A | 8/1999 | Whitmore, III et al. | 600/459 |
| 5,951,476 A | 9/1999 | Beach | 600/437 |
| 5,976,092 A | 11/1999 | Chinn | 600/459 |
| 5,993,389 A | 11/1999 | Driscoll, Jr. et al. | 600/371 |
| 5,997,481 A | 12/1999 | Adams et al. | 600/459 |
| 6,007,499 A | 12/1999 | Martin et al. | 601/3 |
| 6,036,650 A | 3/2000 | Wu et al. | 600/462 |
| 6,039,694 A | 3/2000 | Larson et al. | 600/459 |
| 6,050,943 A | 4/2000 | Slayton et al. | 600/439 |
| 6,067,371 A | 5/2000 | Gouge et al. | 382/128 |
| 6,071,239 A | 6/2000 | Cribbs et al. | 600/439 |
| 6,128,522 A | 10/2000 | Acker et al. | 600/411 |
| 6,179,831 B1 | 1/2001 | Bliweis | 606/21 |
| 6,221,015 B1 | 4/2001 | Yock | 600/439 |
| 6,267,734 B1 | 7/2001 | Ishibashi et al. | 601/2 |
| 6,409,720 B1 | 6/2002 | Hissong et al. | 606/27 |
| 6,425,867 B1 | 7/2002 | Vaezy et al. | 600/439 |
| 6,443,894 B1 | 9/2002 | Sumanaweera et al. | 600/443 |
| 6,488,639 B1 | 12/2002 | Ribault et al. | 601/2 |
| 6,491,672 B2 | 12/2002 | Slepian et al. | 604/267 |
| 6,548,047 B1 | 4/2003 | Unger | 424/9.51 |
| 6,551,576 B1 | 4/2003 | Unger et al. | 424/9.52 |
| 6,584,360 B2 | 6/2003 | Francischelli et al. | 607/98 |
| 6,595,934 B1 | 7/2003 | Hissong et al. | 601/3 |
| 6,599,256 B1 | 7/2003 | Acker et al. | 601/2 |
| 6,626,855 B1 | 9/2003 | Weng et al. | 601/3 |
| 6,633,658 B1 | 10/2003 | Dabney et al. | 382/128 |
| 6,656,136 B1 | 12/2003 | Weng et al. | 601/2 |
| 6,676,601 B1 | 1/2004 | Lacoste et al. | 600/439 |
| 6,685,639 B1 | 2/2004 | Wang et al. | 600/439 |
| 6,709,407 B2 | 3/2004 | Fatemi | 600/559 |
| 6,716,184 B2 | 4/2004 | Vaezy et al. | 601/3 |
| 6,719,694 B2 | 4/2004 | Weng et al. | 600/439 |
| 6,719,699 B2 | 4/2004 | Smith | 600/459 |
| 6,726,627 B1 | 4/2004 | Lizzi et al. | 600/439 |
| 6,735,461 B2 | 5/2004 | Vitek et al. | 600/411 |
| 6,764,488 B1 | 7/2004 | Burbank et al. | 606/51 |
| 6,846,291 B2 | 1/2005 | Smith et al. | 600/459 |
| 6,875,176 B2 | 4/2005 | Mourad et al. | 600/442 |
| 6,875,420 B1 | 4/2005 | Quay | 424/9.52 |
| 6,905,498 B2 | 6/2005 | Hooven | 606/50 |
| 6,932,771 B2 | 8/2005 | Whitmore et al. | 607/105 |
| 6,955,648 B2 | 10/2005 | Mozayeni et al. | 600/454 |
| 7,022,077 B2 | 4/2006 | Mourad et al. | 600/442 |
| 7,052,463 B2 | 5/2006 | Peszynski et al. | 600/459 |
| 7,285,093 B2 | 10/2007 | Anisimov et al. | 600/437 |
| 7,305,264 B2 * | 12/2007 | Larson et al. | 600/427 |
| 7,445,599 B2 | 11/2008 | Kelly et al. | 600/437 |
| 7,470,241 B2 | 12/2008 | Weng et al. | 601/3 |
| 7,510,536 B2 * | 3/2009 | Foley et al. | 601/2 |
| 7,534,209 B2 | 5/2009 | Abend et al. | 600/437 |
| 7,628,764 B2 | 12/2009 | Duarte et al. | 601/2 |
| 7,684,865 B2 | 3/2010 | Aldrich et al. | 607/40 |
| 7,697,972 B2 | 4/2010 | Verard et al. | 600/424 |
| 2002/0193831 A1 | 12/2002 | Smith, III | 607/5 |
| 2003/0018255 A1 | 1/2003 | Martin et al. | 600/3 |
| 2003/0069569 A1 | 4/2003 | Burdette et al. | 600/427 |
| 2003/0195420 A1 | 10/2003 | Mendlein et al. | 600/459 |
| 2004/0002654 A1 | 1/2004 | Davidson et al. | 600/454 |
| 2004/0078034 A1 | 4/2004 | Acker et al. | 606/27 |
| 2004/0097840 A1 | 5/2004 | Holmer | 601/2 |
| 2004/0122493 A1 | 6/2004 | Ishibashi et al. | 600/437 |
| 2004/0153126 A1 | 8/2004 | Okai | 606/27 |
| 2004/0234453 A1 | 11/2004 | Smith | 424/9.5 |
| 2004/0254620 A1 | 12/2004 | Lacoste et al. | 607/96 |
| 2005/0065436 A1 | 3/2005 | Ho et al. | 600/431 |
| 2005/0240102 A1 | 10/2005 | Rachlin et al. | 600/459 |
| 2006/0184069 A1 | 8/2006 | Vaitekunas | 601/2 |
| 2008/0045864 A1 | 2/2008 | Candy et al. | 601/2 |
| 2008/0045865 A1 | 2/2008 | Kislev | 601/3 |
| 2008/0200815 A1 | 8/2008 | Van Der Steen et al. | 600/467 |
| 2008/0319375 A1 | 12/2008 | Hardy | 604/22 |
| 2010/0234728 A1 * | 9/2010 | Foley et al. | 600/439 |
| 2011/0040171 A1 * | 2/2011 | Foley et al. | 600/411 |
| 2011/0040214 A1 * | 2/2011 | Foley et al. | 601/2 |

FOREIGN PATENT DOCUMENTS

| | | |
|---|---|---|
| EP | 0 420 758 | 4/1991 |
| EP | 1 265 223 | 12/2002 |
| JP | H09-103434 | 4/1997 |
| JP | 2002-500939 | 1/2002 |
| JP | 2004-113789 | 4/2004 |
| WO | WO 97/31364 | 8/1997 |
| WO | WO 00/72919 | 12/2000 |
| WO | WO 02/069805 | 9/2002 |

OTHER PUBLICATIONS

Campbell et al. "Pulsatile Echo-encephalography." *Acta Neurologica Scandinavica Supplementum 45*, vol. 46: 1-57, 1970.

Dahl et al., "Simultaneous Assessment of Vasoreactivity Using Transcranial Doppler Ultrasound and Cerebral Blood Flow in Healthy Subjects." *Journal of Cerebral Blood Flow and Metabolism*, vol. 14, No. 6: 974-981, 1994.

Gao et al., "Imaging of the Elastic Properties of Tissue—a Review." *Ultrasound in Medicine & Biology*, vol. 22, No. 8: 959-977, 1996.

Klingelhöfer et al., "Chapter 4: Functional Ultrasonographic Imaging" in Babikian VL, Wechsler LR, eds. *Transcranial Doppler Ultrasonography*. Woburn, MA: Butterworth-Heinemann, 49-66, 1999.

Markwalder et al., "Dependency of Blood Flow Velocity in the Middle Cerebral Artery on End-Tidal Carbon Dioxide Partial Pressure—A Transcranial Ultrasound Doppler Study." *Journal of Cerebral Blood Flow and Metabolism*, vol. 4, No. 3: 368-372, 1984.

Accord et al., "The Issue of Transmurality in Surgical Ablation for Atrial Fibrillation." *Cardiothoracic Surgery Network*: 3pp, Aug. 8, 2005.

American Red Cross., "Blood 101." 4pp., Dec. 11, 2007.

Anand et al., "Monitoring formation of high intensity focused ultrasound (HIFU) induced lesions using backscattered ultrasound." *Acoustical Society of America*; Mar. 10, 2004

Anand et al., "Using the ATL 1000 to Collect Domodulated RF Data for Monitoring HIFU Lesion Formation." *Presented at SPIE Medical Imaging 2003*. 11pp, 2003.

Bachmann et al., "Targeting Mucosal Addressin Cellular Adhesion Molecule (MAdCAM)-1 to Noninvasively Image Experimental Crohn's Disease." *Gastroenterology*; vol. 130: 8-16, 2006.

Bauer et al., "Ultrasound Imaging with SonoVue: Low Mechanical Index Real-Time Imaging." *Acad. Radiol.*; vol. 9, Suppl. 2: S282-S284, 2002.

Beard et al., "An Annular Focus Ultrasonic Lens for Local Hyperthermia Treatment of Small Tumors." *Ultrasound in Medicine & Biology*; vol. 8, No. 2: 177-184, 1982.

Bokarewa et al., "Tissue factor as a proinflammatory agent." *Arthritis Research*, vol. 4: 190-195, Jan. 10, 2002.

Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.

Brayman et al., "Erosion of Artificial Endothelia In Vitro by Pulsed Ultrasound: Acoustic Pressure, Frequency, Membrane Orientation and Microbubble Contrast Agent Dependence." *Ultrasound in Medicine & Biology*; vol. 25, No. 8: 1305-1320, 1999.

Buller et al., "Accurate Three-dimensional Wall Thickness Measurement From Multi-Slice Short-Axis MR Imaging." *Computers in Cardiology*, 245-248, 1995.

Chao et al., "Aspheric lens design." *Ultrasonics Symposium*, 2000 IEEE, vol. 2: Abstract Only, Oct. 2000.

Chen et al., "A comparison of the fragmentation thresholds and inertial cavitation doses of different ultrasound contrast agents." *Journal of the Acoustical Society of America*, vol. 113, No. 1: 643-665, Jan. 2003.

Chen et al., "Inertial Cavitation Dose and Hemolysis Produced In Vitro With or Without Optison." *Ultrasound in Medicine & Biology*, vol. 29, No. 5: 725-737, 2003.

Chong et al., "Tissue Factor and Thrombin Mediate Myocardial Ischemia-Reperfusion Injury." *The Society of Thoracic Surgeons*, vol. 75: S649-655, 2003.

Dayton et al., "The magnitude of radiation force on ultrasound contrast agents." *Journal of the Acoustical Society of America*, vol. 112, No. 5, Part 1: 2183-2192, Nov. 2002.

Dempsey et al., "Thickness of Carotid Artery Atherosclerotic Plaque and Ischemic Risk." *Neurosurgery*, vol. 27, No. 3: 343-348, 1990.

Ebbini et al., "Image-guided noninvasive surgery with ultrasound phased arrays." *SPIE*, vol. 3249: 230-239, Apr. 2, 1998.

Everbach et al., "Cavitational Mechanisms in Ultrasound-Accelerated Thrombolysis at 1 MHz." *Ultrasound in Medicine & Biology*, vol. 26, No. 7: 1153-1160, 2000.

Ewert et al., "Anti-myeloperoxidase antibodies stimulate neutrophils to damage human endothelial cells." *Kidney International*, vol. 41: 375-383, 1992.

Ganapathy et al., "A New General Triangulation Method for Planar Contours." *Computer Graphics* vol. 16, No. 3:69-75, 1982.

Guzman et al., "Ultrasound—Mediated Disruption of Cell Membranes. I. Quantification of Molecular uptake and Cell Viability. / II. Heterogeneous effects on cells." *Journal of the Acoustical Society of America*, vol. 110, No. 1: 588-606, Jul. 2001.

Hadimioglu et al., "High-Efficiency Fresnel Acoustic Lenses." *Ultrasonics Symposium 1993 IEEE*: 579-582, 1993.

Hatangadi, Ram. "A Novel Dual Axis Multiplanar Transesophageal Ultrasound Probe for Three-Dimensional Echocardiograph." *University of Washington, Department of Sciences and Engineering*, vol. 55-11B: Abstract 1pg, 1994.

Holt et al., "Bubbles and Hifu: the Good, the Bad and the Ugly." *Boston University, Department of Aerospace and Mechanical Engineering*: 120-131, 2002.

Hubka et al., "Three-dimensional echocardiographic measurement of left ventricular wall thickness: In vitro and in vivo validation." *Journal of the American Society of Echocardiography*, vol. 15, No. 2: 129-135, 2002.

Hwang et al., "Vascular Effects Induced by Combined 1-MHz Ultrasound and Microbubble Contrast Agent Treatments In Vivo." *Ultrasound in Medicine & Biology*, vol. 31, No. 4: 553-564, 2005.

Hynynen et al., "Potential Adverse Effects of High-Intensity Focused Ultrasound Exposure on Blood Vessels in Vivo." *Ultrasound in Medicine & Biology*, vol. 22, No. 2: 193-201, 1996.

Iannuzzi et al., "Ultrasonographic Correlates of Carotid Atherosclerosis in Transient Ischemic Attack and Stroke." *Stroke*, ProQuest Medical Library, vol. 26, No. 4: 614-619, 1995.

Idell et al., "Fibrin Turnover in Lung Inflammation and Neoplasia." *American Journal of Respiratory and Critical Care Medicine*, vol. 163: 578-584, 2001.

Indman, Paul. "Alternatives in Gynecology." *Hysteroscopy*, OBGYN.net, 2000. http://www.gynalternatives.com/hsc.html.

Kaczkowski et al., "Development of a High Intensity Focused Ultrasound System for Image-Guided Ultrasonic Surgery." *Ultrasound for Surgery*, 2001. <http://cimu.apl.washington.edu/hifusurgerysystem.html>.

Kang et al., "Analysis of the Measurement Precision of Arterial Lumen and Wall Areas Using High-Resolution MRI." *Magnetic Resonance in Medicine*, vol. 44: 968-972, 2000.

Klibanov et al., "Detection of Individual Microbubbles of an Ultrasound contrast Agent: Fundamental and Pulse Inversion Imaging." *Academy of Radiology*, vol. 9, Suppl. 2: S279-S281, 2002.

Kudo et al., "Study on Mechanism of Cell Damage Caused by Microbubbles Exposed to Ultrasound." *Ultrasound in Medicine & Biology*, vol. 29, Supplement: 4pp, 2003.

Lalonde et al., "Field conjugate acoustic lenses for ultrasound hyperthermia." *Ultrasonics, Ferroelectrics and Frequency Control, IEEE Transactions*, vol. 40, Issue 5: Abstract 1pg., Sep. 1993.

Miller et al., "A Review of in Vitro Bioeffects of Inertial Ultrasonic Cavitation From a Mechanistic Perspective." *Ultrasound in Medicine & Biology*, vol. 22, No. 9: 1131-1154, 1996.

Miller et al., "Diagnostic ultrasound activation of contrast agent gas bodies induces capillary rupture in mice." *PNAS*, vol. 97, No. 18: 10179-10184, 2000.

Ng et al., "Therapeutic Ultrasound: Its Application in Drug Delivery." *Medicinal Research Reviews*, vol. 22, No. 2: 204-233, 2002.

O'Leary et al., "Carotid-artery Intima and Media Thickness as a Risk Factor for Myocardial Infarction and Stroke in Older Adults." Cardiovascular Health Study Collaborative Research Group. *New England Journal of Medicine*, vol. 340, No. 1: 14-22, Jan. 7, 1999.

Ostensen et al., "Characterization and Use of Ultrasound Contrast Agents." *Academy of Radiology*, vol. 9, Suppl. 2: S276-S278, 2002.

Owaki et al., "The Ultrasonic Coagulating and Cutting System Injuries Nerve Function." *Endoscopy*, vol. 34, No. 7: 575-579, 2002.

Pignoli et al., "Intimal plus medial thickness of the arterial wall: a direct measurement with ultrasound imaging." *Circulation*, vol. 74, No. 6:1399-1406, Dec. 1986.

Poliachik et al., "Activation, Aggregation and Adhesion of Platelets Exposed to High-Intensity Focused Ultrasound." *Ultrasound in Medicine & Biology*, vol. 27, No. 11: 1567-1576, 2001.

Poliachik et al., "Effect of High—Intensity Focused Ultrasound on Whole Blood With or Without Microbubble Contrast Agent." *Ultrasound in Medicine & Biology*, vol. 25, No. 6: 991-998, 1999.

Porter et al., "Ultrasound, Microbubbles and Thrombolysis." *Progress in Cardiovascular Diseases*, vol. 44, No. 2: 101-110, Oct. 2001.

Rivens et al., "Vascular Occlusion Using Focused Ultrasound Surgery for Use in Fetal Medicine." *European Journal of Ultrasound*, vol. 9: 89-97, 1999.

Rosen et al., "Vascular Occlusive Diseases." 37pp., revised 2002.

Rosenschein et al., "Shock-Wave Thrombus Ablation, A New Method for Noninvasive Mechanical Thrombolysis." *The American Journal of Cardiology*, vol. 70, Issue 15: Abstract, Nov. 15, 1992.

Rosenschein et al., "Ultrasound Imaging-Guided Nonivasive Ultrasound Thrombolysis-Preclinical Results." *Circulation*, vol. 102: 238-245, 2000. <http://www.circulationaha.com.org>.

Schulte-Altedorneburg et al., "Accuracy of In Vivo Carotid B-Mode Ultrasound Compared with Pathological Analysis: Intima-Media Thickening, Lumen Diameter, and Cross-Sectional Area." *Stroke*, vol. 32, No. 7: 1520-1524, 2001.

Tachibana et al., "Albumin Microbubble Echo-Contrast Material as an Enhancer for Ultrasound Accelerated Thrombolysis." *Circulation*, vol. 92: 1148-1150, 1995.

Tachibana et al., "The Use of Ultrasound for Drug Delivery." *Echocardiography*, vol. 18, No. 4: 323-328, May 2001.

Tardy et al., "In Vivo Ultrasound Imaging of Thrombi Using a Target-specific Contrast Agent." *Academy of Radiology*, vol. 9, Suppl. 2: S294-S296, 2002.

Vaezy et al., "Acoustic surgery." *Physics World*: 35-39, Aug. 2001.

Vaezy et al., "Hemostasis and Tumor Treatment using High Intensity Focused Ultrasound: Experimental Investigations and Device Development." *First International Workshop on the Application of HIFU in Medicine*: 46-49, 2001.

Vaezy et al., "Hemostasis using high intensity focused ultrasound." *European Journal of Ultrasound*, vol. 9: 79-87, 1999.

Vaezy et al., "Intra-operative acoustic hemostasis of liver: production of a homogenate for effective treatment." *Ultrasonics*, vol. 43: 265-269, 2005.

Von Land et al., "Development of an Improved Centerline Wall Motion Model." *IEEE*: 687-690, 1991.

Watkin et al., "Multi-Modal Contrast Agents: A First Step." *Academy of Radiology*, vol. 9, Suppl. 2: S285-S287, 2002.

Wickline et al., "Blood Contrast Enhancement with a Novel, Non-Gaseous Nanoparticle Contrast Agent." *Academy of Radiology*, vol. 9, Suppl. 2: S290-S293, 2002.

Williamson et al., "Color Doppler Ultrasound Imaging of the Eye and Orbit." *Survey of Ophthamology*, vol. 40, No. 4: 255-267, 1996.

Yu et al., "A microbubble agent improves the therapeutic efficiency of high intensity focused ultrasound: a rabbit kidney study." *Urological Research*, PubMed: Abstract, 2004.

N.a., "Cavitation." Ultrasound TIP—U.S. Database: Dec. 12, 2007.

N.a., "Mechanical Bioeffects in the Presence of Gas-Carrier Ultrasound Contrast Agents." *Journal of Ultrasound & Medicine*, vol. 19: 120-142, 2000.

N.a., "Breast Cancer—Insightec: focused ultrasound for non invasive treatment." FAQ, 2000. <http://www.exablate2000.com/physicians_faq.html>.

* cited by examiner

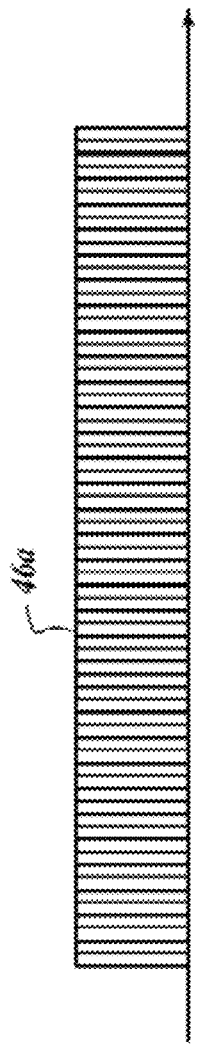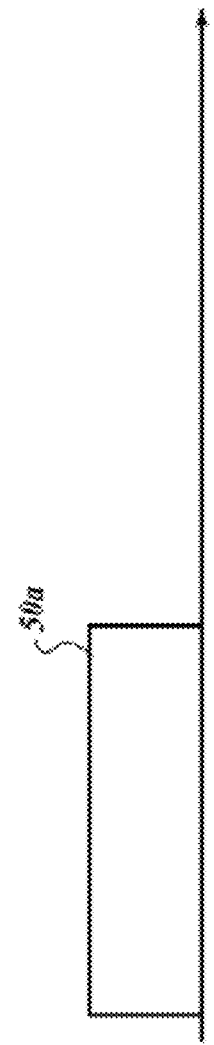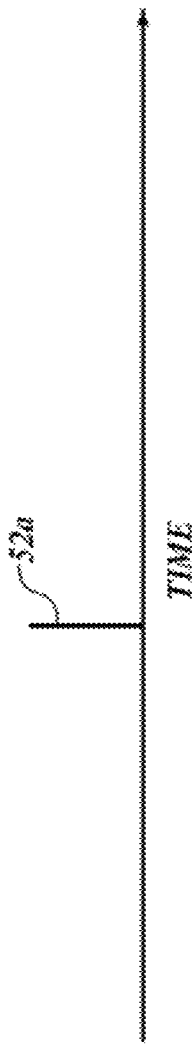

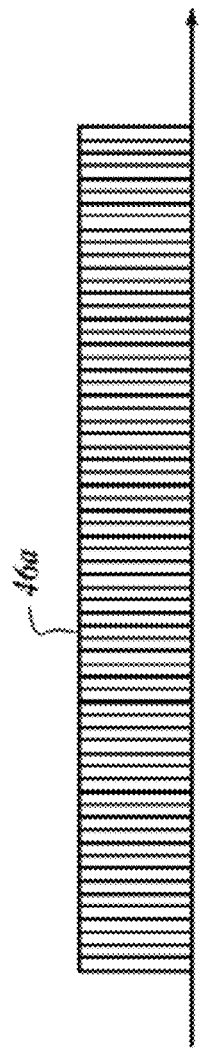
FIG. 3B(1)  FIG. 3B(2)  FIG. 3B(3)  FIG. 3B(4)

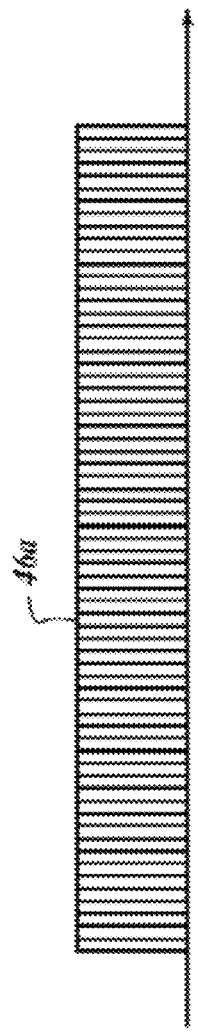
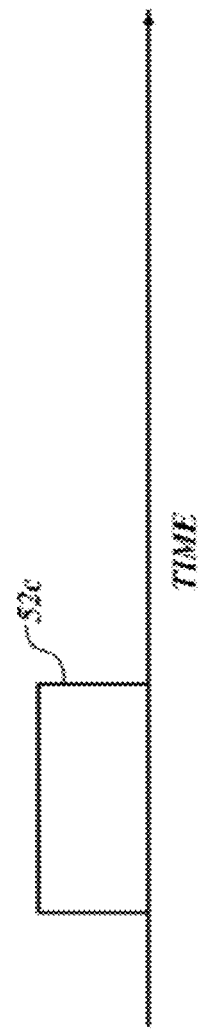
FIG. 3C(1)
FIG. 3C(2)
FIG. 3C(3)
FIG. 3C(4)

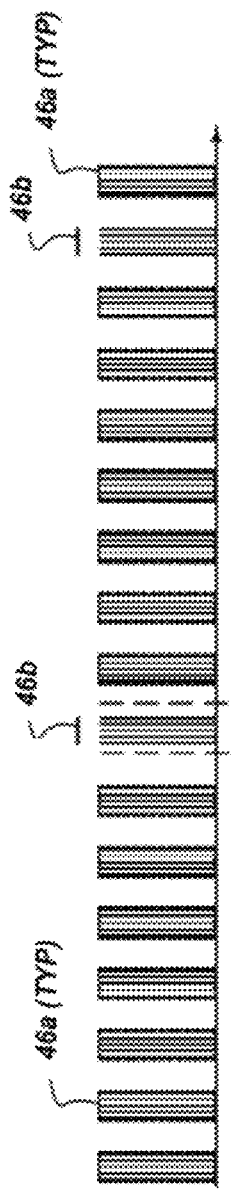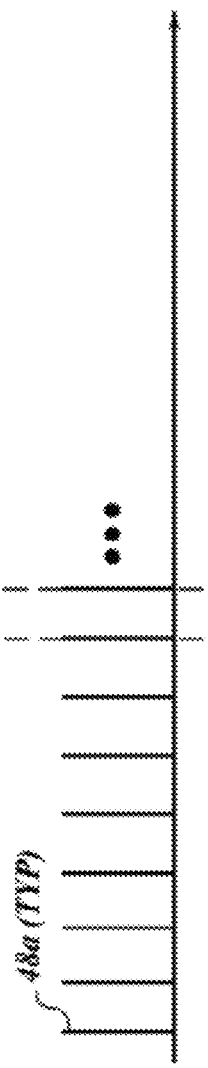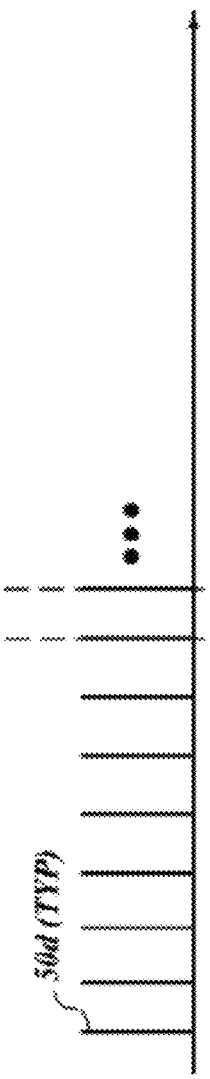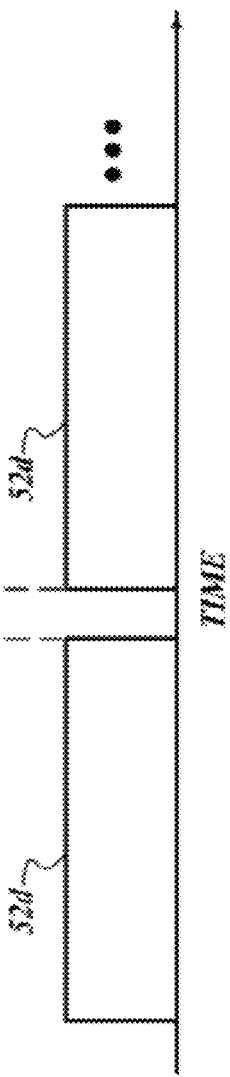

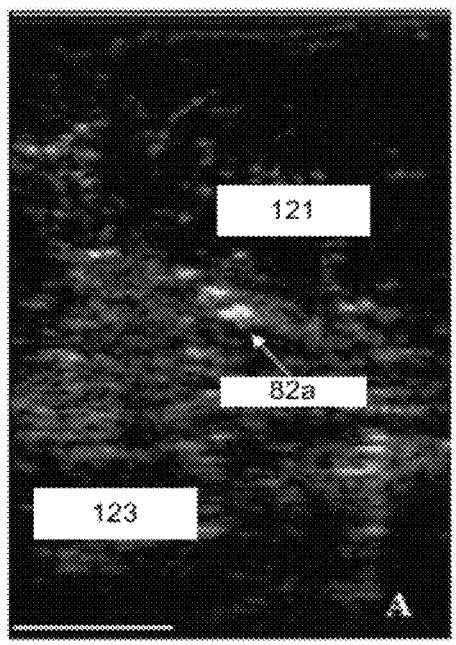
*FIG. 11A*
*FIG. 11B*
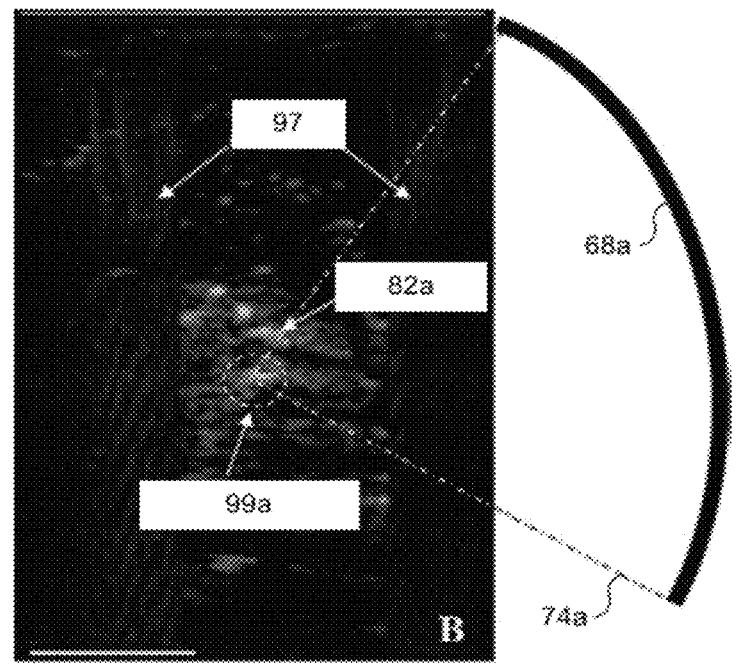

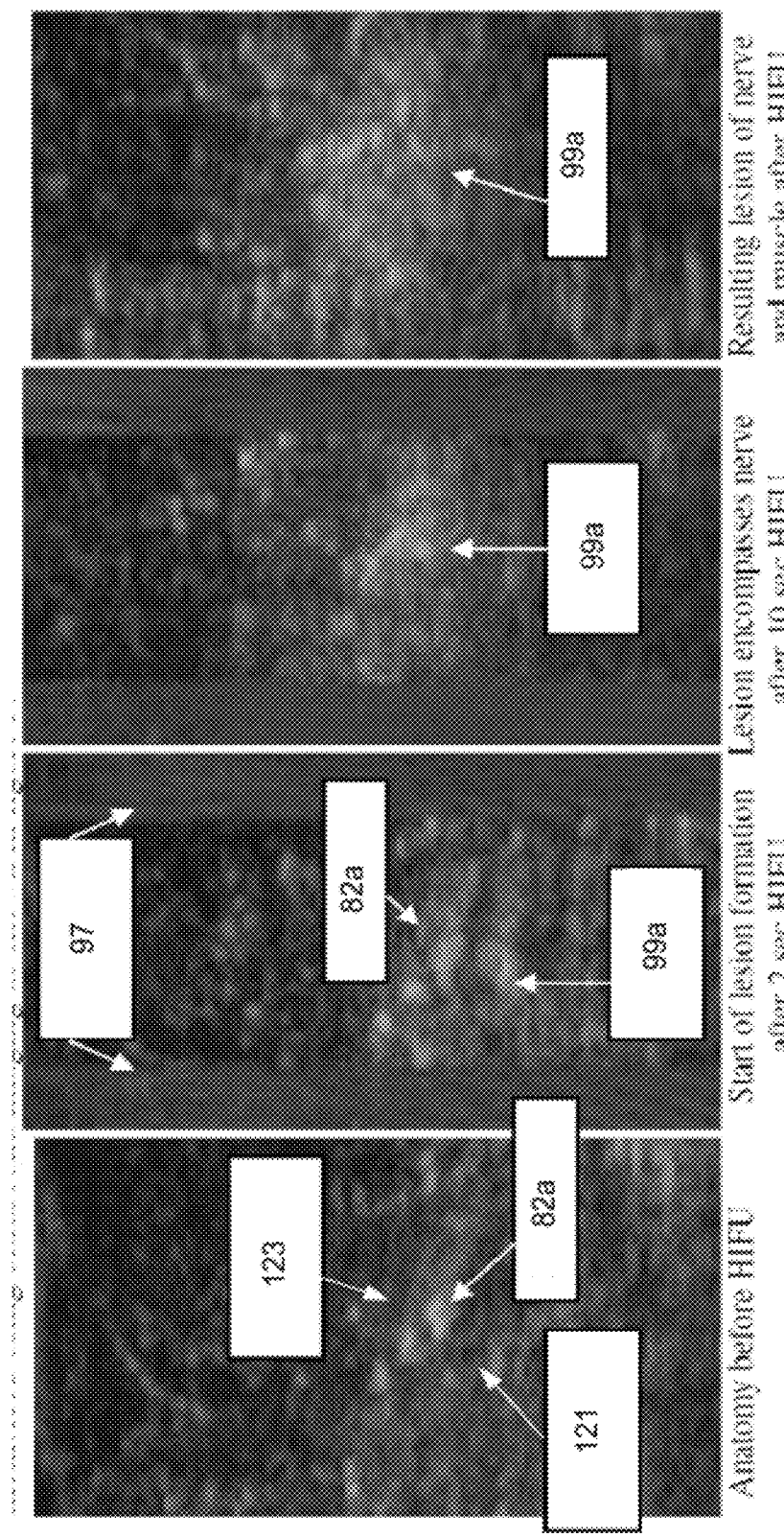

ULTRASOUND IMAGE GUIDED HIFU DEVICE FOR REMOTE APPLICATION TO RAT SCIATIC NERVE

VISUALLY GUIDED HIFU DEVICE FOR DIRECT CONTACT APPLICATION TO RAT SCIATIC NERVE

IMAGE GUIDED HIGH INTENSITY FOCUSED ULTRASOUND TREATMENT OF NERVES

RELATED APPLICATIONS

This application is a continuation of a copending patent application Ser. No. 12/390,975, filed on Feb. 23, 2009, which itself is a divisional of a prior patent application Ser. No. 11/016,701, filed on Dec. 16, 2004, and issued as U.S. Pat. No. 7,510,536 on Mar. 31, 2009; which itself is based on a prior provisional application Ser. No. 60/529,916, filed on Dec. 16, 2003, the benefits of the filing dates of which are hereby claimed under 35 U.S.C. §119(e) and 120.

GOVERNMENT RIGHTS

This invention was made with government support under grant No. DAM-17-02-2-0014 awarded by the U.S. Army. The government has certain rights in the invention.

BACKGROUND

HIFU has emerged as a precise, non-surgical, minimally-invasive treatment for benign and malignant tumors. At focal intensities (1000-10000 $W/cm^2$) that are 4-5 orders of magnitude greater than that of diagnostic ultrasound (approximately 0.1 $W/cm^2$), HIFU can be applied percutaneously to induce lesions (i.e., localized tissue necrosis) at a small, well defined region (approximately 1 mm) deep within tissue, while leaving intervening tissue between the HIFU transducer and the focal point substantially unharmed. Tissue necrosis is a result of tissue at the focal point of the HIFU beam being heated to over 70° C. in a very short period of time (generally less than one second). Tissue necrosis also results from cavitation activity, which causes tissue and cellular disorganization. HIFU is currently being used clinically for the treatment of prostate cancer and benign prostatic hyperplasia, as well as the treatment of malignant bone tumors and soft tissue sarcomas. Clinical trials are currently being conducted for HIFU treatment of breast fibroadenomas, and various stage-4 primary and metastatic cancerous tumors of the kidney and liver.

Therapeutic uses of HIFU have generally been directed at destroying undesired masses of tissue, to necrose tumors, coagulate bleeding, and address urological and gynecological disorders. Most references teach that one must use extreme care when using HIFU to treat tissue near a nerve, to avoid undesirably damaging the nerve. There are however, several medical conditions where it would be desirable to treat a nerve. For example, a temporary blocking of a nerve would prevent transmission of pain signals through that nerve, and could therefore be used for pain management. Temporary or permanent blockage by the nerve could also be used to treat spasticity.

Spasticity is a complication associated with disorders of the central nervous system (CNS), such as multiple sclerosis, cerebral palsy, stroke, and traumatic injury to the brain or spinal cord, and is displayed by uncontrollable muscle contractions. Spasticity due to trauma results from the generation of hyperactive nerve reflexes in pathways below the site of spinal cord or brain damage. It is estimated that over 500,000 individuals in the U.S. and over 12 million worldwide are affected by spasticity, many of whom suffer from severe spasticity, which includes violent and immobilizing spasms, despite paralysis in the lower limbs due to spinal cord injury or disease. Severe spasticity can also affect those with multiple sclerosis, traumatic brain injury, stroke, and cerebral palsy, among other CNS disorders. Many of these individuals retain voluntary function of the hyperactive nerve reflexes, but the interfering spasticity limits this function and compromises quality of life by causing pain and disrupting sleep.

The cause of spasticity is thought to involve hyperactivity of stretch reflexes. One proposed neuronal mechanism is that inhibitory portions of the reflex arc are impaired and thus, reflex muscle contractions may be unintentionally excited and proceed in a less controlled manner. Another proposed neuronal mechanism is that Ia afferents of the stretch reflex sprout new synapses on motoneurons in response to loss of normal supraspinal input due to a CNS disorder; as a result, the sprouted Ia afferents exert exaggerated synaptic excitation of motoneurons causing spasticity.

Mild or moderate spasticity can often be managed with physical methods (e.g., stretching, bracing) or oral spasmolytic medications (e.g., baclofen, tizanidine). However, these treatments are not adequate in the 25% to 50% of patients with severe spasticity. Treatments for severe spasticity include intramuscular blocks with botulinum toxin (BTX), which is often injected into 1 or 2 muscles with localized severe spasticity. For example, spasticity in ankle plantarflexor muscles causing clonus can be reduced with BTX injections into the gastrocnemius and soleus muscles. However, BTX has only modest effects in reducing spasticity. Only 1 or 2 large muscles can be injected because of concerns about systemic effects that could paralyze respiratory muscles, the duration of benefit is only 3-6 months, and repeated injections may be less effective because antibodies to BTX can develop.

Chemical nerve blocks with phenol or alcohol are also common treatments of severe spasticity. These chemical blocks can be applied to both peripheral nerves and spinal nerves to provide treatment of spasticity that is either localized to a specific muscle group or more widespread. The disadvantages to chemical nerve blocks include the risk of infection due to needle insertion, the difficulty in titration of the effect of treatment, and a risk (10 to 30%) of transient dysesthesias.

For very extreme cases of spasticity, patients often undergo peripheral surgery for cutting nerves or tendons, spinal cord surgery for cutting dorsal roots (dorsal rhizotomy) or cutting the spinal cord itself (i.e., longitudinal myelotomy). Other treatments of spinal nerve roots include intrathecal phenol and paravertebral alcohol neurolytic blocks. Paravertebral injections with alcohol carry the risk of infection and the risk of ascending myelopathy if the injected alcohol enters a dural root sleeve. Intrathecal phenol injections carry significant risks, such as the risk of disrupting bowel, bladder, and sexual function, the risk of infection, and the risk of ascending myelopathy because of migration of the phenol. Dorsal rhizotomy and lumbar myelotomy carry all of the risks associated with major surgery (i.e., risks associated with general anesthesia and the risk of infection). A less invasive, radio frequency rhizotomy uses thermo-coagulation of spinal nerves to control spasticity, although the risk of infection is still associated with this technique because the technique requires needle insertion.

Most current treatment options for severe spasticity are primarily used for patients with no preserved voluntary function, because these treatments (BTX, chemical nerve blocks, and the extreme case of nerve transection surgeries) have a non-selective effect on the local nerves and/or muscles. The result will be suppression of voluntary function in the treated region, either temporarily or permanently. Another treatment option, intrathecal baclofen infusion via a subcutaneous pump, has been used to treat patients who retain limited voluntary function. Such treatment (a continuous intrathecal infusion of the spasmolytic medication baclofen around the lumbar spinal cord) has been successful in reducing spastic contractions while preserving voluntary function, although the mechanism of its selectivity is not well understood. Despite its effectiveness, the invasiveness of the procedure and cost of the implantation procedure and the pump itself make other alternative procedures (such as nerve blocks and intramuscular blocks) more attractive for patients with no voluntary function.

Current treatments of spasticity can be classified as those that suppress voluntary function (intramuscular injections, nerve blocks, surgical treatments) and those that can retain voluntary function (stretching, oral medications, and intrathecal baclofen). Only stretching and oral medications are non-invasive treatments, and those treatments are ineffective for severe spasticity. Therefore, it would be desirable to provide a new, non-invasive treatment for severe spasticity. It would further be desirable to employ a non-invasive treatment that can achieve a relatively temporary partial conduction block, a relatively permanent partial conduction block, a relatively temporary complete conduction block, and a relatively permanent complete conduction block.

Severe chronic pain is a common clinical neurological condition. Such pain can be associated with some forms of cancer (particularly bone cancer), pain caused by peripheral nerve injury such as herpetic neuralgia, and some arthritis pain such as spinal facet arthropathies. Current treatments of pain include oral medications (e.g., morphine), local neurolytic alcohol injections, and thermo-coagulation of nerves. Similar to the treatments of spasticity, these methods are invasive, are often less effective than desired, and often have undesirable side effects. It would therefore be further desirable to provide a non-invasive method of treatment for sensory nerves in pain management.

Ultrasound has previously been used to treat less severe pain in physical therapy settings, in which the ultrasound beam is typically unfocused and of relatively low intensity compared to HIFU. The diffuse energy may act to soothe pain by providing heat to the area, acting no differently than a warm bath or massage. It would be desirable to provide a method for alleviating pain using HIFU by treating nerves with HIFU to achieve both thermal and mechanical interaction with nerves.

SUMMARY

This application specifically incorporates by reference the disclosures and drawings of each patent application and issued patent identified above as a related application.

Disclosed herein is a method for using HIFU to treat the nervous system. In a particularly preferred embodiment of the invention, ultrasound imaging is synchronized to the HIFU therapy to achieve real-time ultrasound image guided HIFU therapy of the nervous system. Alternatively, MRI can be used to image the nervous system as it is being treated with HIFU. The treatment site in the nervous system is selected based on the type of therapeutic effect desired. HIFU therapy of the nervous system can be utilized to achieve a treatment for spasticity, to alleviate pain, to provide an anesthetic effect, and to provide a cosmetic effect.

Regardless of the desired therapeutic effect, HIFU therapy of neural structures preferably includes the following steps. First, a specific treatment site in the nervous system is selected. The specific treatment site will be selected based on a thorough knowledge of anatomy and a thorough understanding of the portions of the neural structure that need to be targeted to achieve the desired therapeutic effect. An understanding of how HIFU interacts with the specific portion of the neural structure being targeted is required, including the relevant dosage of HIFU required to achieve the desired therapeutic effect. Empirical studies have indicated that relatively lower levels of HIFU can induce reversible therapeutic effects in neural structures, whereas relatively higher levels of HIFU can induce permanent therapeutic effects in neural structures. Once the specific treatment site has been identified, the appropriate dosage is selected. Just as a physician needs to understand a pharmacological dose required to achieve a desired therapeutic effect, a HIFU clinician will need to understand (preferably based on empirical studies) the HIFU dosage required to achieve the desired therapeutic effect.

Once the treatment site and the dosage have been selected, a HIFU therapy probe is positioned adjacent to the treatment site such that the focal point of the HIFU transducer is directed toward the selected treatment site. The HIFU therapy probe can be positioned externally of the patient, or inside the body cavity of the patient. Either position will facilitate a non-invasive procedure. Of course, the HIFU therapy probe can be invasively disposed adjacent to the treatment site within the body; however, a specific advantage of HIFU therapy of nerves is the ability to induce a therapeutic effect without an invasive procedure. In one aspect of the invention, HIFU transducers having a fixed focal length will be utilized. When using such HIFU transducers, an understanding of the anatomical position of the selected treatment site and knowledge of the focal length of the HIFU transducer will enable a clinician to select an appropriate position for the HIFU therapy probe. In another embodiment of the invention, the HIFU therapy probe will include an array of HIFU transducers, enabling variable focal lengths to be achieved. When using such a HIFU therapy probe, understanding of the anatomical location of the selected treatment site and a thorough understanding of the characteristics of the variable focal lengths can be used to similarly enable a clinician to select an initial positioning of the HIFU therapy probe.

Because it is possible that an improperly positioned HIFU therapy probe could inadvertently damage non-target tissue, preferably, the position of the focal point of the HIFU therapy transducer relative to the treatment site is verified before HIFU therapy of the nervous system is initiated. Several different techniques or combinations thereof can be used to provide such verification. A first technique involves using an imaging technology such as ultrasound or MRI to obtain an image of the treatment site. Based on an understanding of the geometry of the HIFU transducer, an icon can be introduced into this image to indicate the relative position of the focal region of the HIFU transducer, by understanding the position of the HIFU transducer relative to the imaging instrumentation. One aspect of this technique is to couple an ultrasound imaging probe and the HIFU therapy probe to a frame, such that the relative positions of the imaging probe and the HIFU therapy probe do not change (this can also be achieved by combining imaging and therapy transducers on a single probe, where the positions of the transducers are fixed relative to the probe). The position of the focal point of the HIFU transducer in an image provided by the ultrasound imaging probe can be determined geometrically, or empirically, by using a gel phantom. An icon can be introduced into the ultrasound image (for example, by placing a transparent sheet over the ultrasound image and introducing the icon onto the transparent sheet). The ultrasound imaging probe (being still coupled to the frame and the HIFU therapy probe, so that the relative positions of the probes do not change, since changing their relative positions at this point would render the icon inaccurate) is then used to image the treatment site. The ultrasound imaging probe is manipulated until the icon coincides with the selected treatment site. Because the ultrasound imaging probe and the HIFU therapy probe are coupled to the frame, movement of the ultrasound imaging probe will result in a corresponding movement of the HIFU therapy probe. Ensuring that the icon coincides with the treatment site can be used to verify that the HIFU therapy probe is properly positioned relative to the treatment site before initiating HIFU therapy of the nervous system. In still other embodiments of the invention, sophisticated tracking systems are employed to provide the clinician an indication of where the focal point of the HIFU transducer is, relative to the patient, by providing an image of the patient with an icon in the image indicating the position of the focal point.

Another technique that can be used to verify that the HIFU therapy probe is properly positioned relative to the treatment site involves initially positioning the HIFU therapy probe and then using imaging ultrasound to obtain an image of the treatment site. The HIFU therapy probe is then energized at a relatively low setting, using an insufficient amount of energy to induce damage at the focal point of the HIFU therapy transducer, while still using sufficient energy to change the echogenicity of tissue at the focal point. Empirical studies have indicated that relatively low levels will induce a change in echogenicity in tissue without inducing any apparent damage. This change in echogenicity can be detected in the ultrasound image. Because HIFU introduces significant noise into ultrasound image, it is important that the ultrasound imaging system and the HIFU therapy probe be synchronized, so that the treatment site can be visualized in the ultrasound image. This technique can be used independently of the icon technique discussed above, or as further verification that the icon actually does represent the actual focal point of the HIFU transducer.

Still another technique that can be used to verify that the focal point of the HIFU therapy transducer coincides with the desired treatment site is to provide a short HIFU burst, and then to observe any physiological response to the short HIFU burst before the HIFU therapy is initiated. Empirical studies have shown that there are portions of the nervous system that react to HIFU with a characteristic physiological response, much like a physician can induce a knee-jerk response by lightly striking a knee in a specific anatomical location. The HIFU clinician will apply a relatively short burst of HIFU and monitor for any such characteristic physiological reaction. If the expected physiological reaction occurs, it provides an indication that the HIFU therapy probe is properly positioned relative to the treatment site. It should be noted that this technique provides a less qualified verification than the techniques described above and thus appears to be better suited to applications of relatively low dosage of HIFU that do not induce permanent therapeutic effects.

Once the clinician has verified that the HIFU therapy probe is properly positioned, the therapy is provided according to the dosage levels previously determined. The clinician can then determine whether the desired therapeutic effect has been achieved, and if not, additional therapy can be provided. If the desired therapeutic effect has been achieved, the HIFU therapy probe is removed. Again, several different techniques can be used to determine whether the desired therapeutic effect has been achieved. Preferably, the treatment site will be imaged in real-time using synchronized ultrasound so that the formation of the lesions at the treatment site can be monitored. The experienced clinician will be able to then determine, based on the successful formation of lesions, whether the desired therapeutic effect has likely been achieved. Other techniques of determining whether the desired therapeutic effect has been achieved can alternatively be implemented. If the desired therapeutic effect is the treatment of spasticity, the patient can be monitored to determine if spasticity is reduced. If the desired therapeutic effect is the reduction of pain, the patient can be questioned to determine if the pain has been alleviated. If the desired therapeutic effect is to provide an anesthetic effect, again, the patient can be questioned to determine if any anesthetic effect has been induced, and if so, to what degree. If the desired therapeutic effect is to provide a cosmetic effect (for example, neural structures controlling the facial muscles that are currently treated with Botox to provide a more youthful appearance could instead be treated with HIFU to achieve a similar effect), the patient's appearance can be evaluated to determine if the desired cosmetic effect has been achieved.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A (prior art) schematically illustrates an ultrasonic image generated during the simultaneous use of ultrasound for imaging and for providing HIFU therapy in a conventional manner, wherein noise due to the HIFU beam obscures the entire image;

FIG. 1B schematically illustrates an ultrasonic image generated during the simultaneous use of ultrasound for imaging and therapy, wherein pulsing of the HIFU limits the resulting noise to a portion of the image;

FIG. 1C schematically illustrates an ultrasonic image generated during the simultaneous use of ultrasound for imaging and therapy, wherein synchronized pulsing of the HIFU is used to shift the noise caused by the HIFU beam away from a treatment site displayed in the image;

FIG. 2 is a block diagram illustrating the components of a system capable of the simultaneous use of ultrasound for imaging and therapy, in accord with the present invention;

FIGS. 3A(1)-3D(4) illustrate timing and synchronization patterns that enable the simultaneous use of ultrasound for imaging and therapy;

Figure 5A:
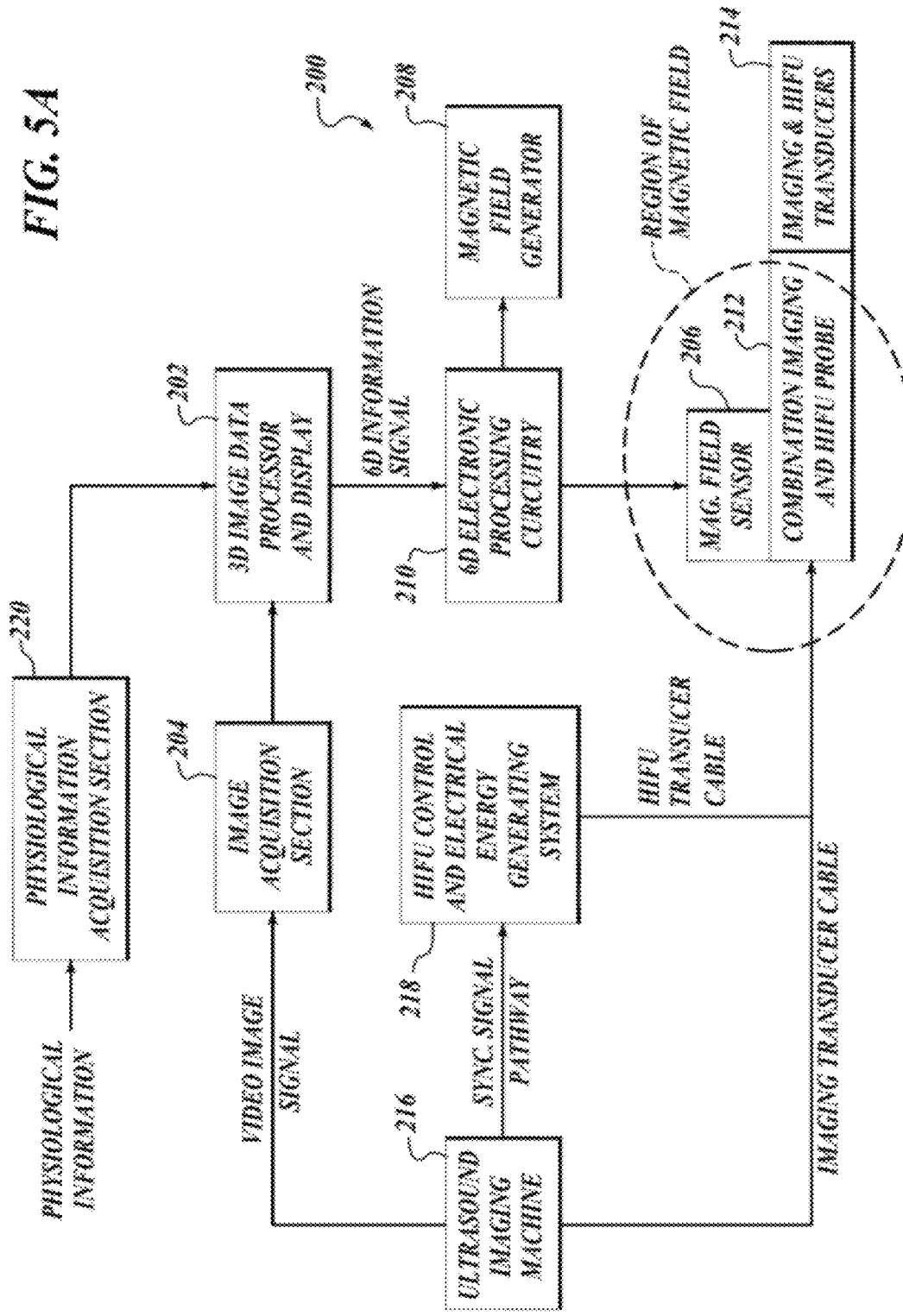
FIG. 5A is a schematic block diagram of a 3D imaging and HIFU therapy system that enables the HIFU therapy to be applied at selected treatment sites in a 3D image of a target area.
Figure 5B:
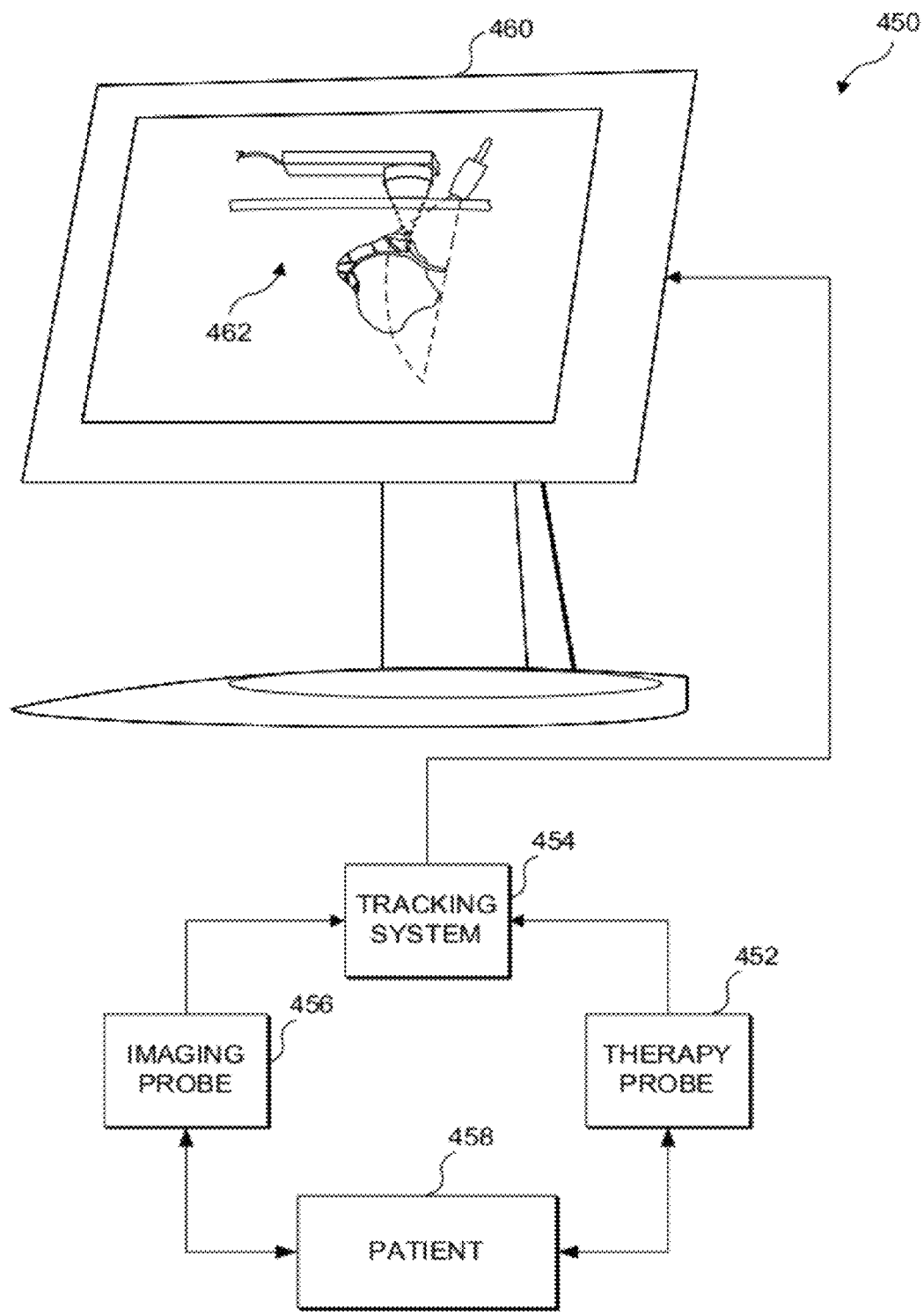
FIG. 5B is a block diagram schematically illustrating the elements of a system for use with the present invention to facilitate free hand visualization of the focal point of a HIFU beam during therapy.
Figure 5C:
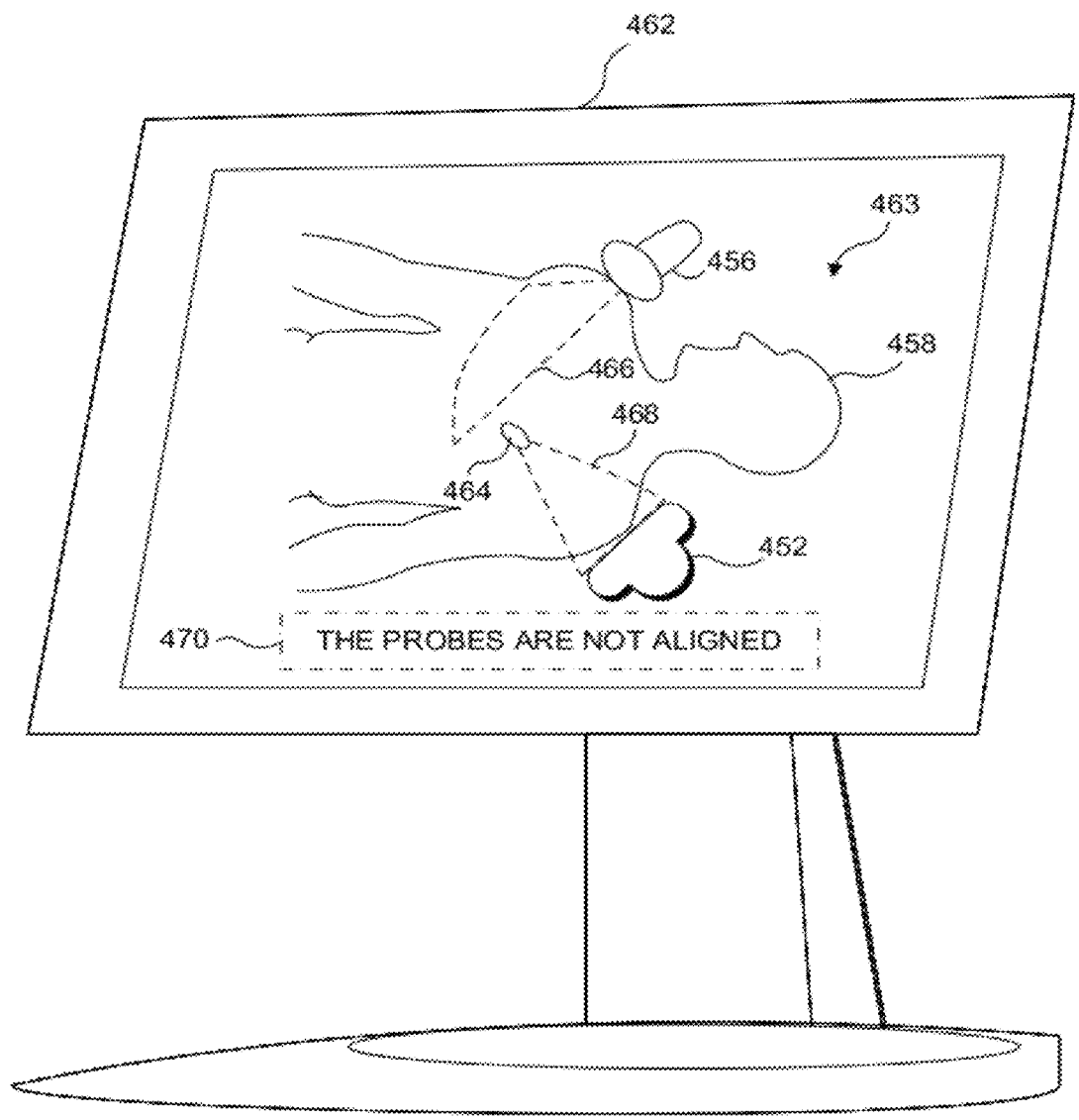
Figure 6A:
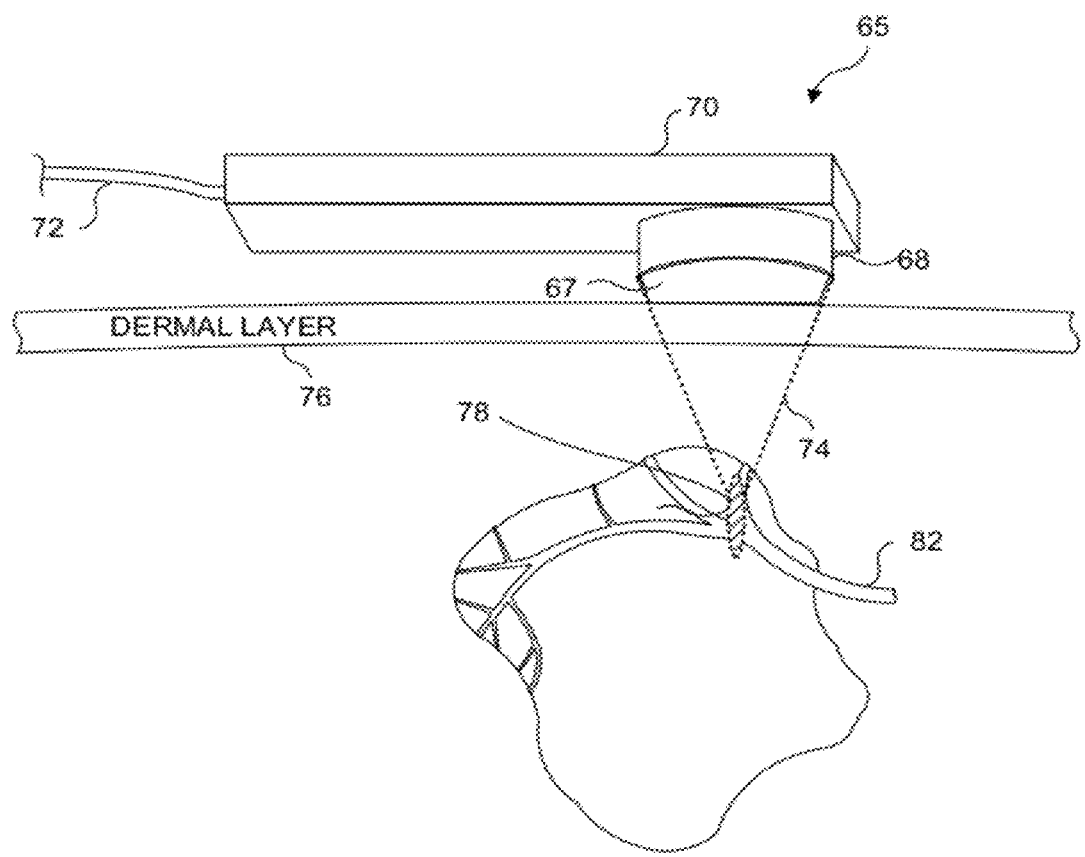
Figure 6B:
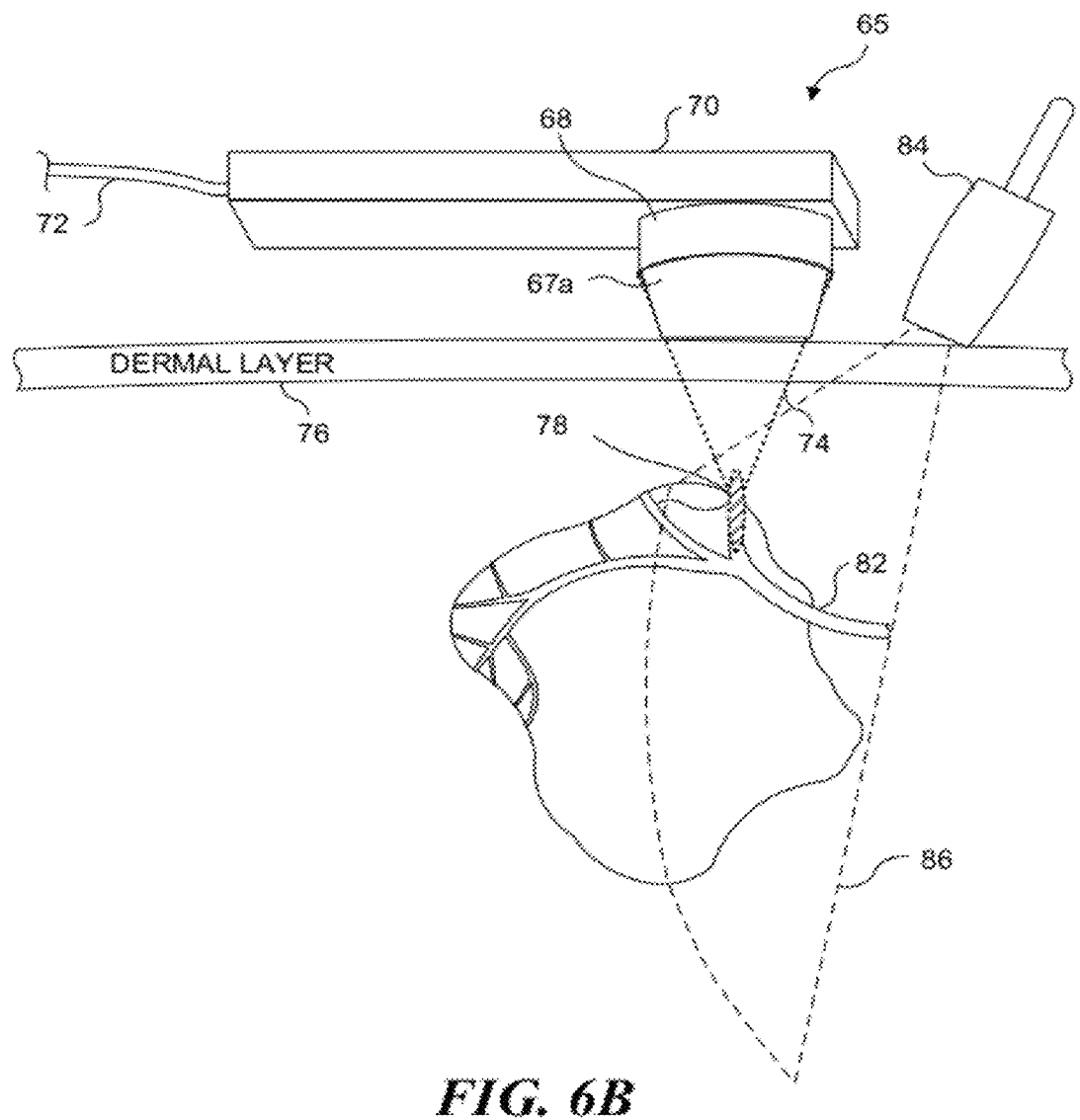
Figure 6C:
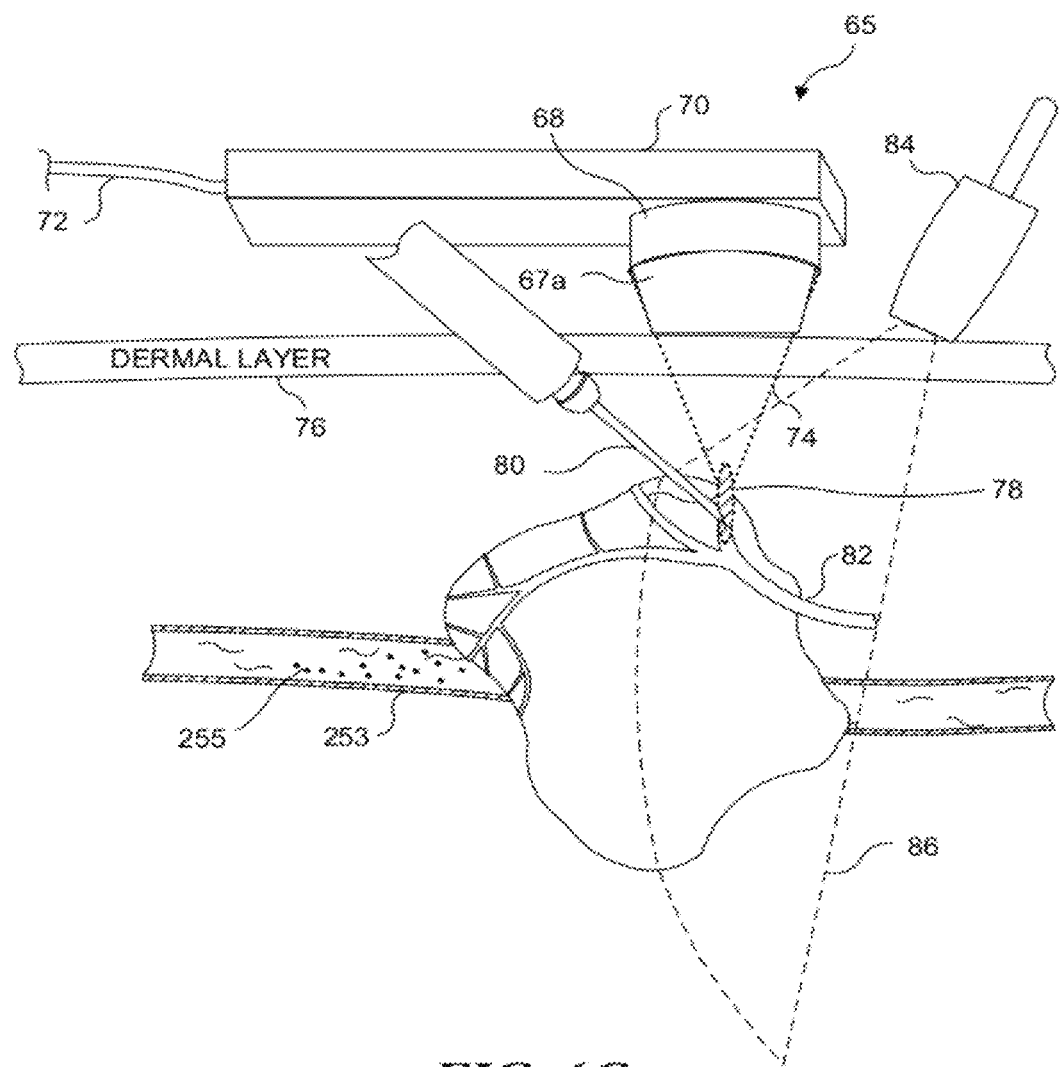
Figure 7:
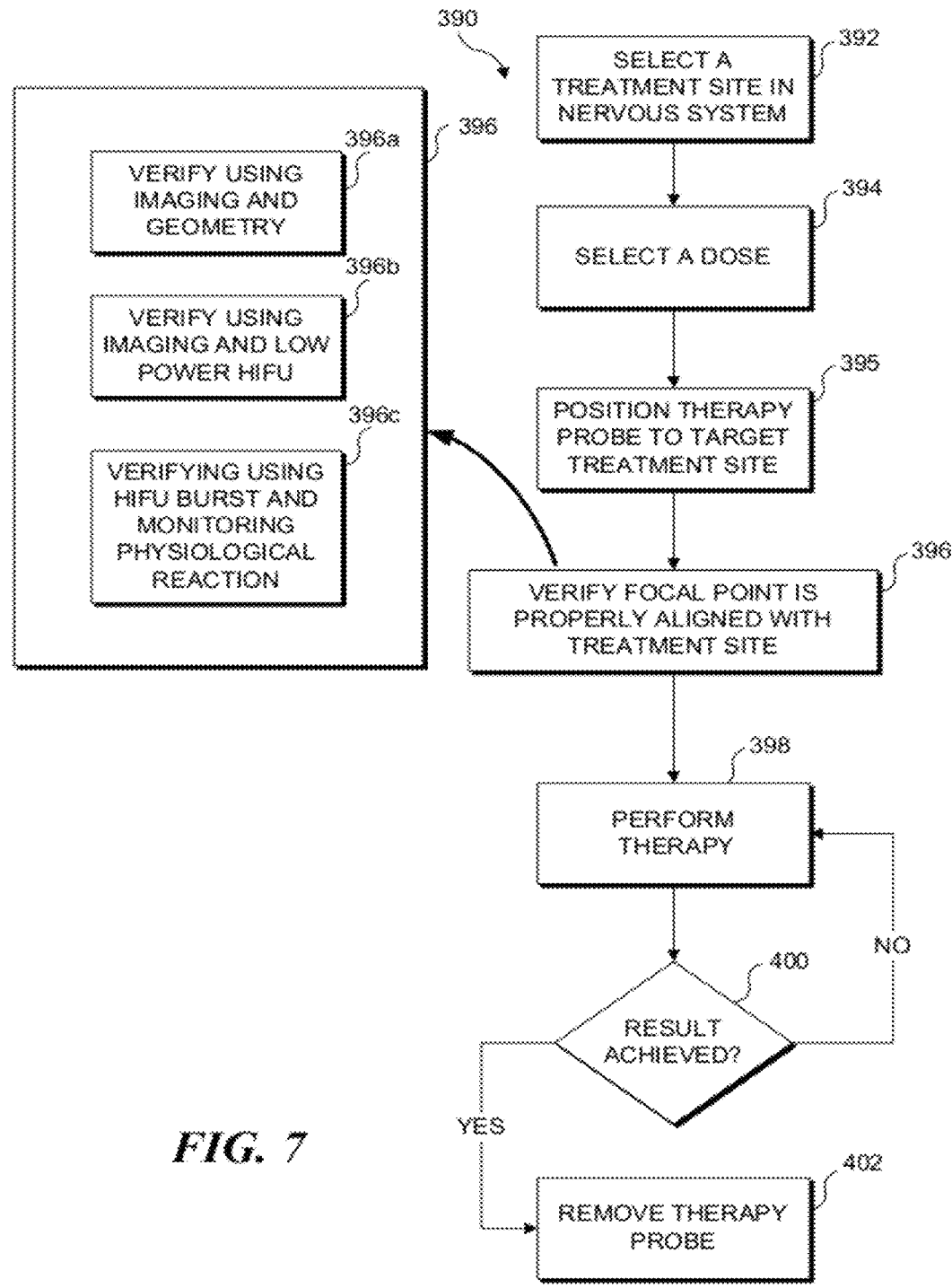
Figure 8A:
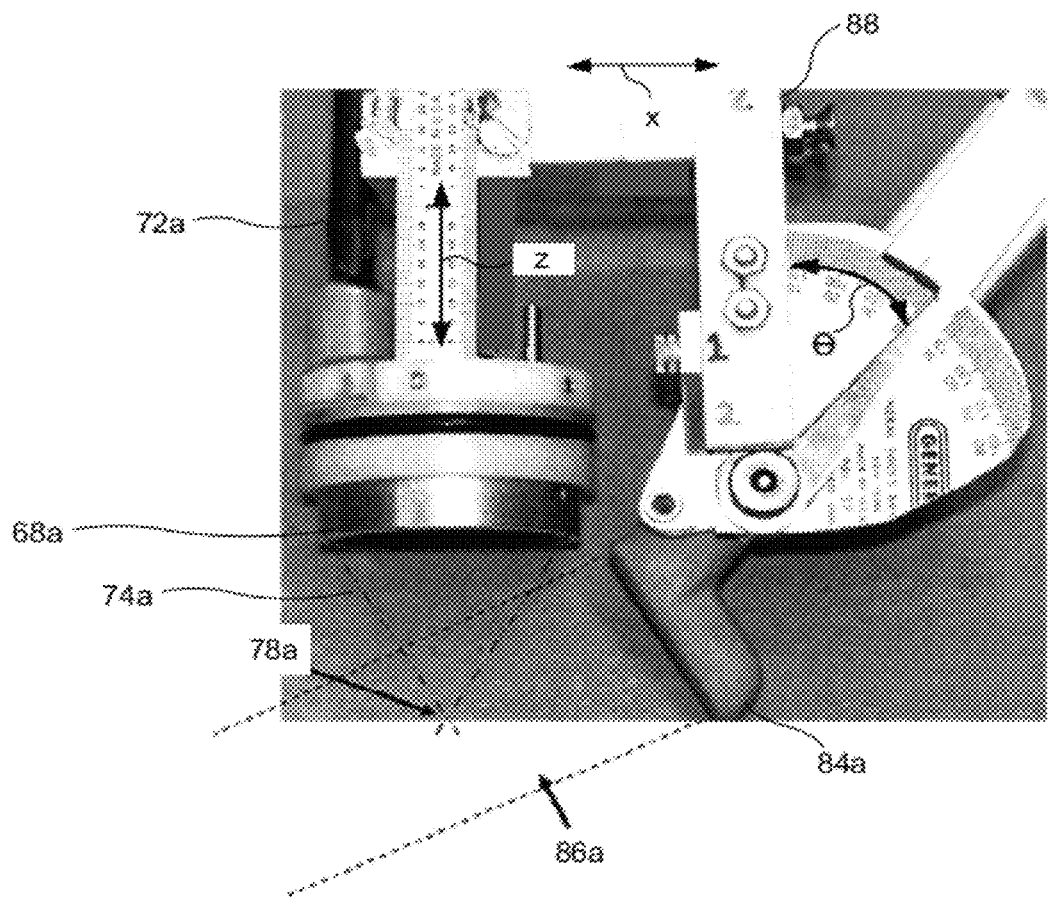
Figure 8B:
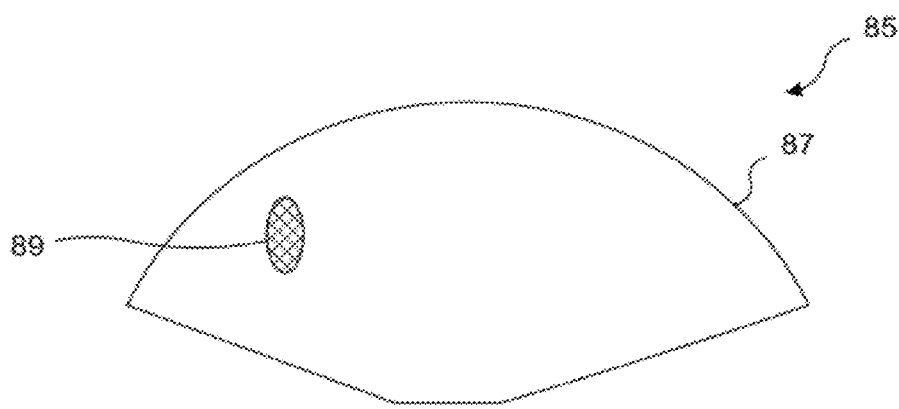
Figure 8C:
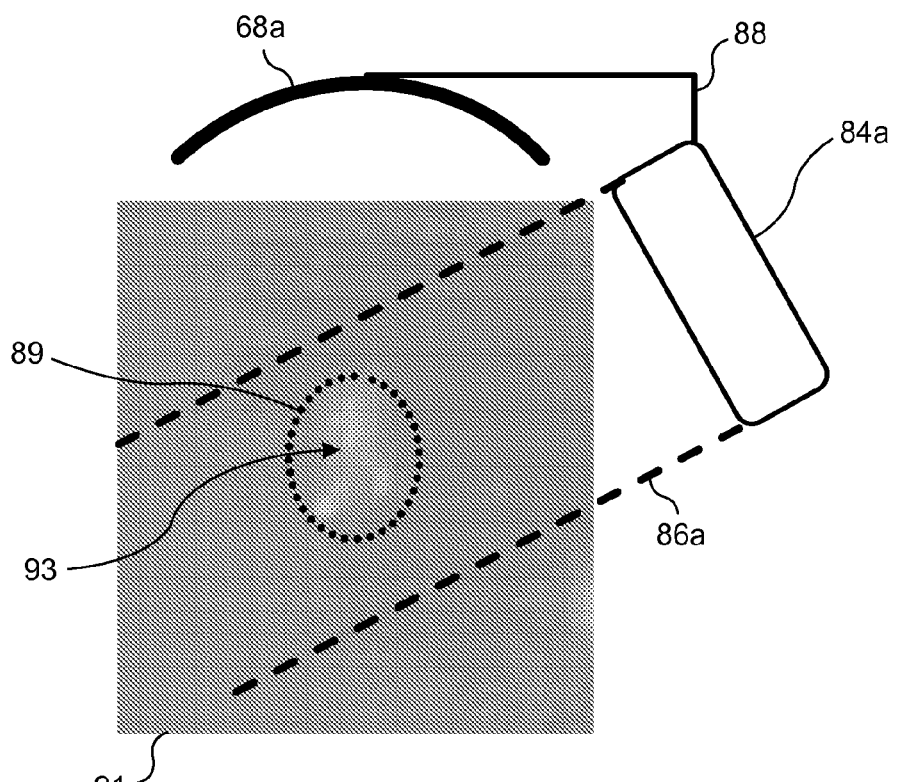
Figure 8D:
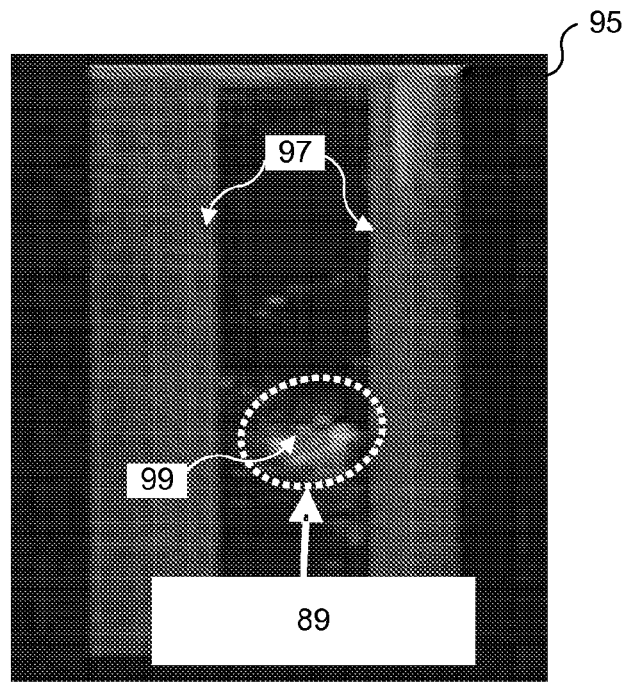
Figure 9A:
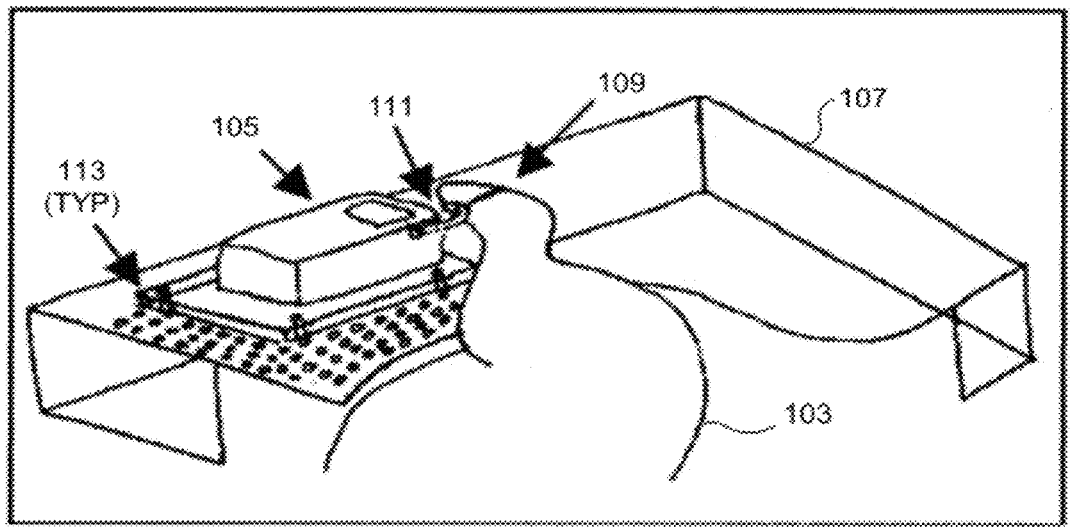
Figure 9B:
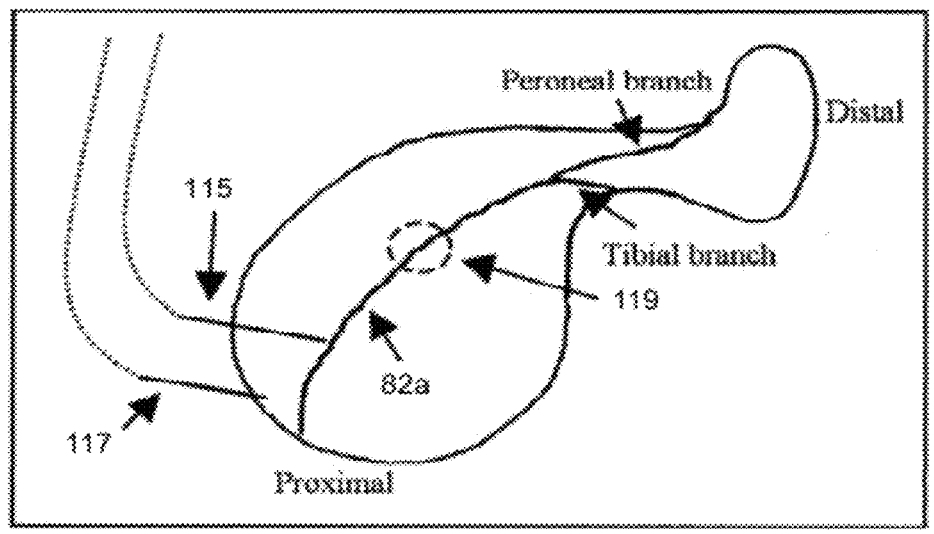
Figure 9C:
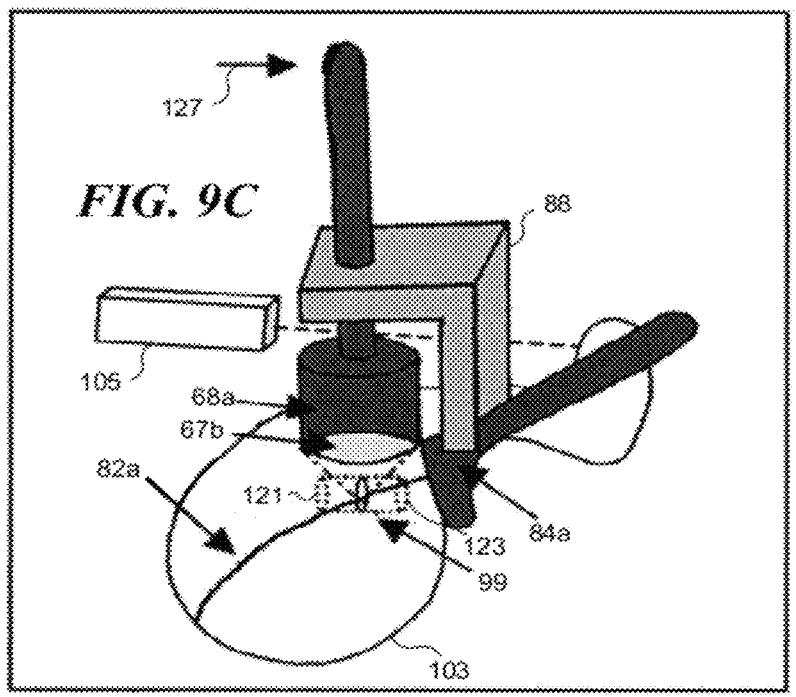
Figure 9D:
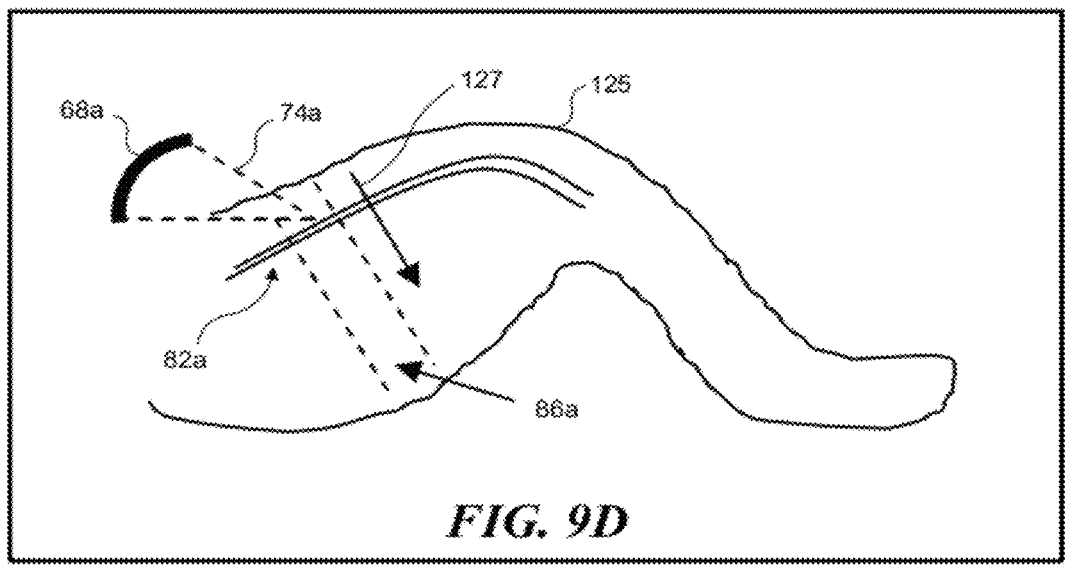
Figure 9E:
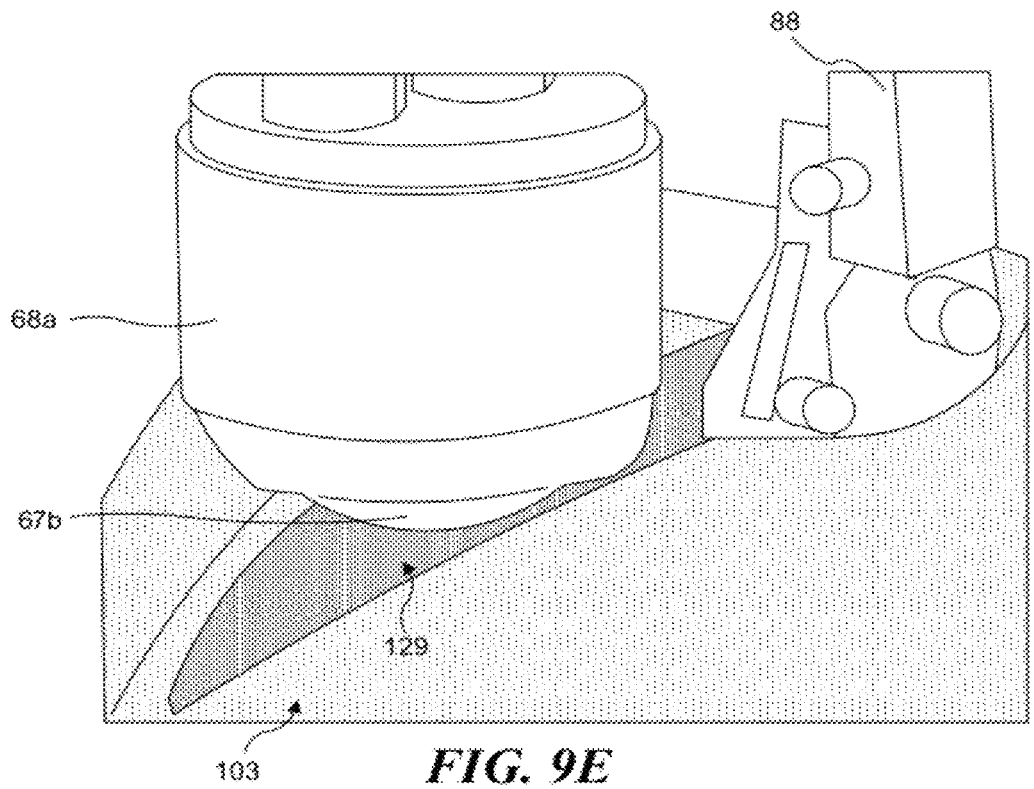
Figure 13:
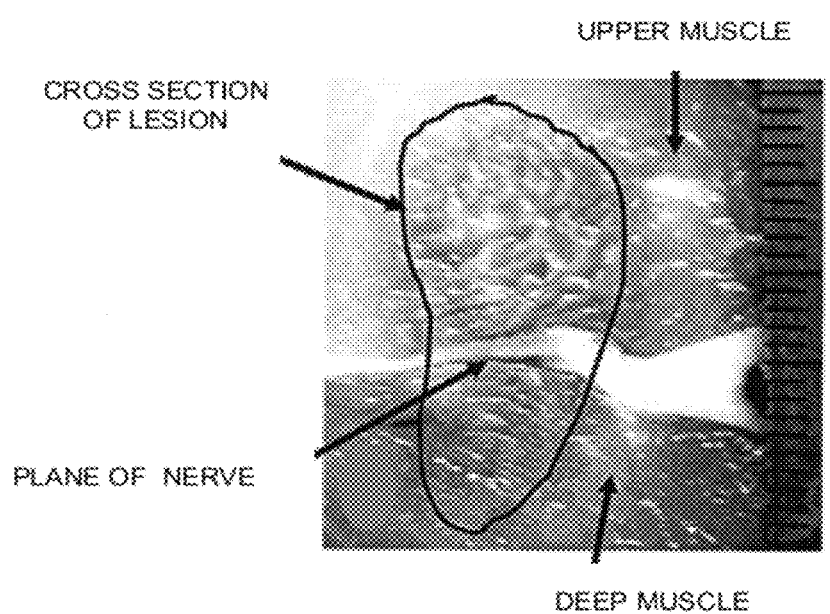
Figure 10A:
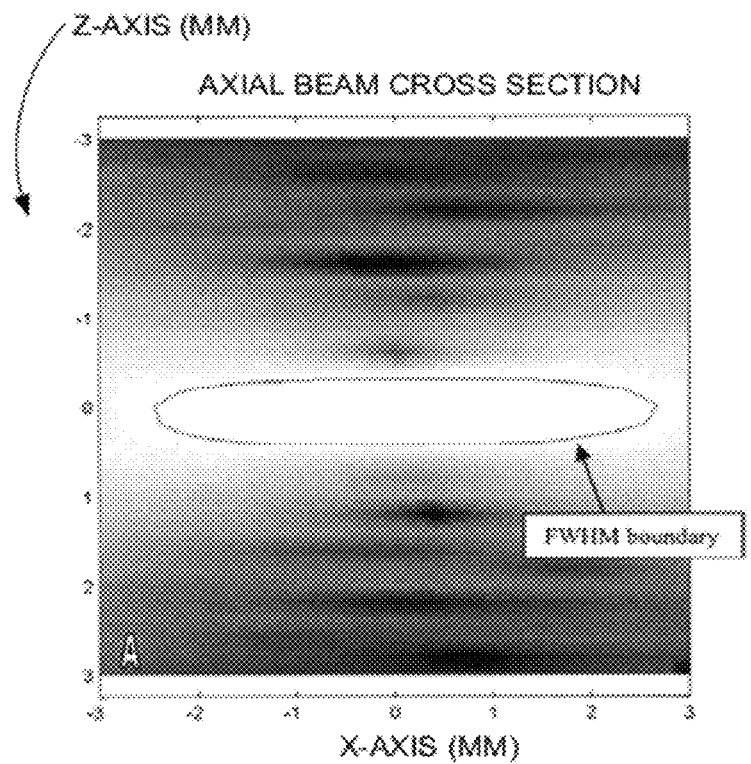
Figure 10B:
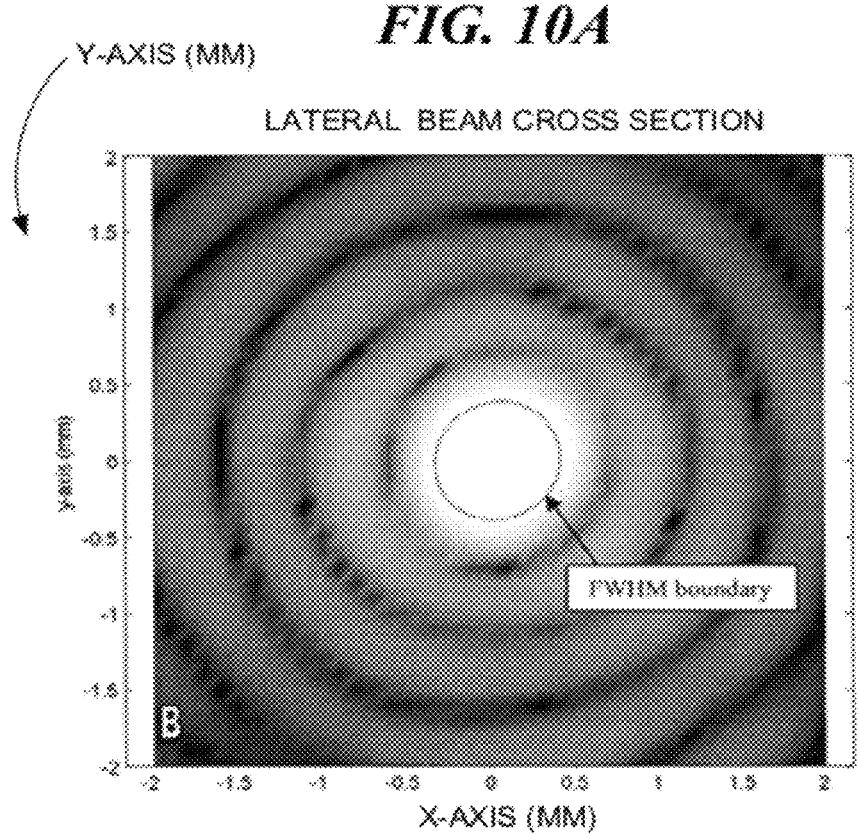
Figure 16A:
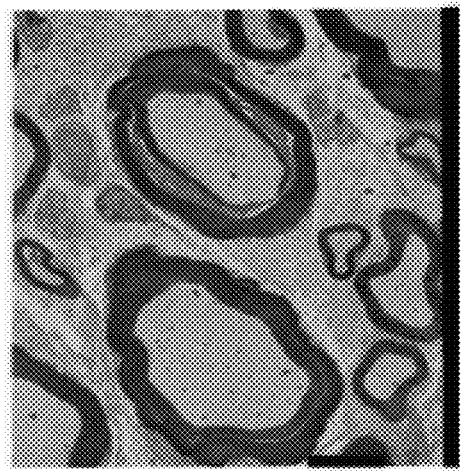
Figure 16B:
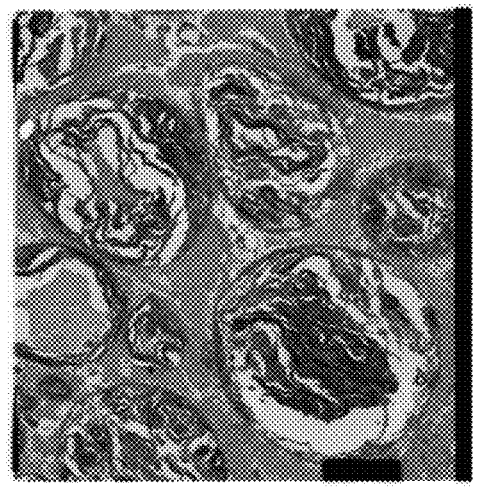
Figure 16C:
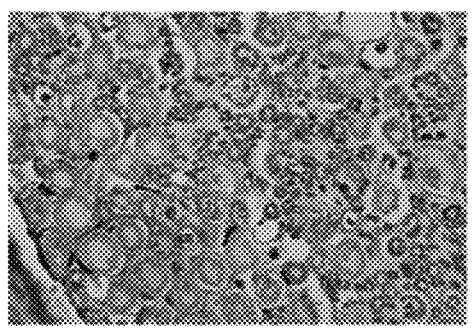
Figure 16D:
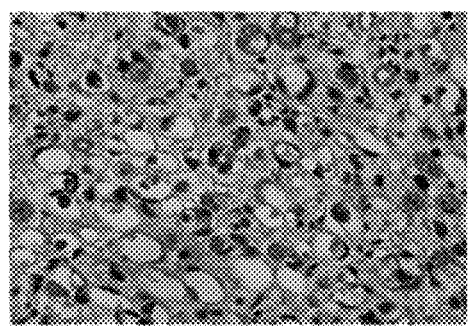
Figure 17:
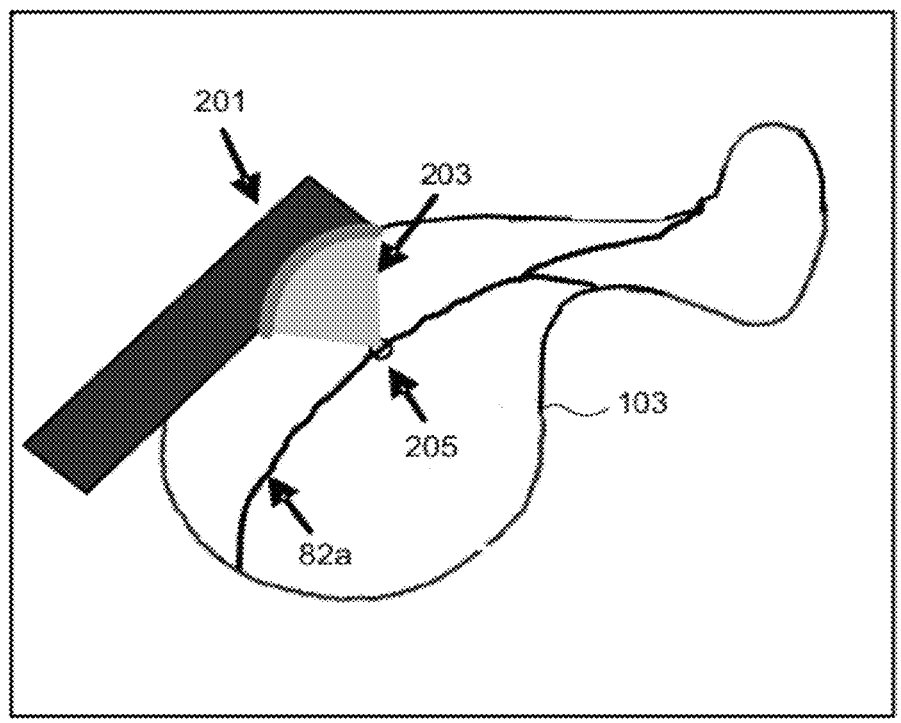
Figure 18:
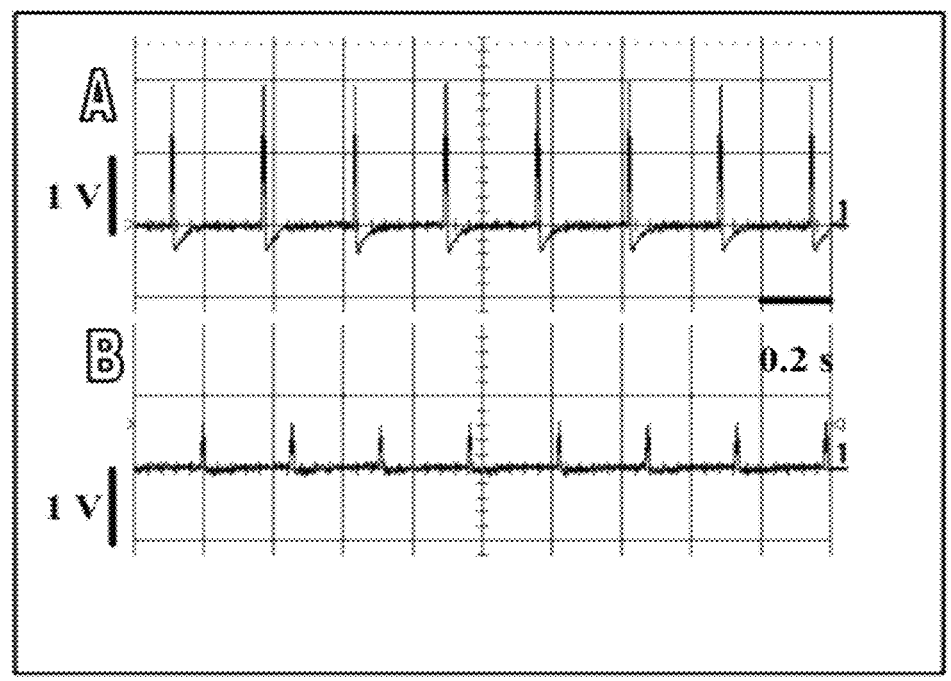
Figure 19:
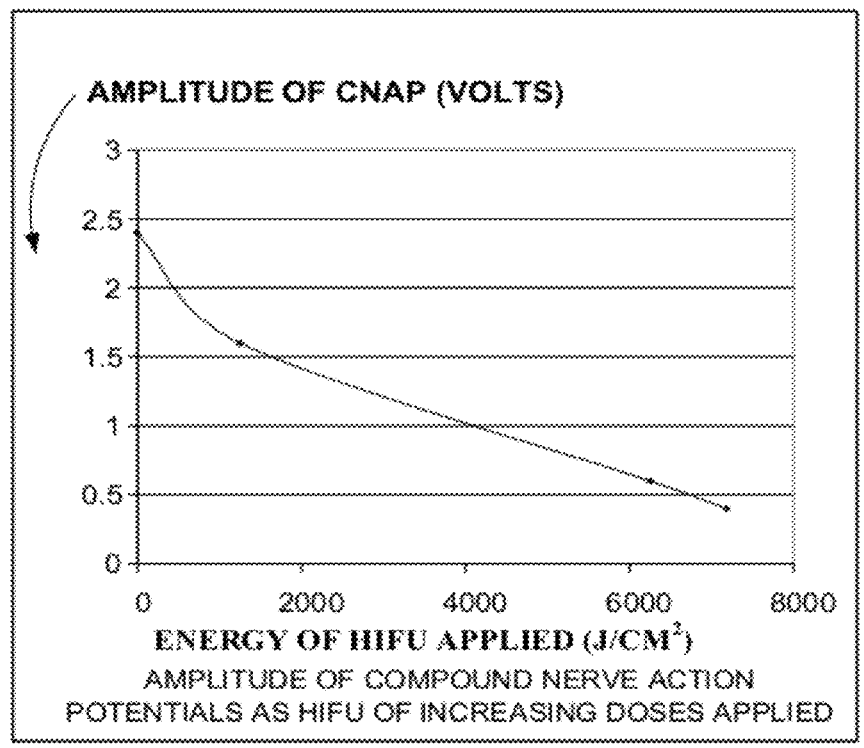
Figure 20:
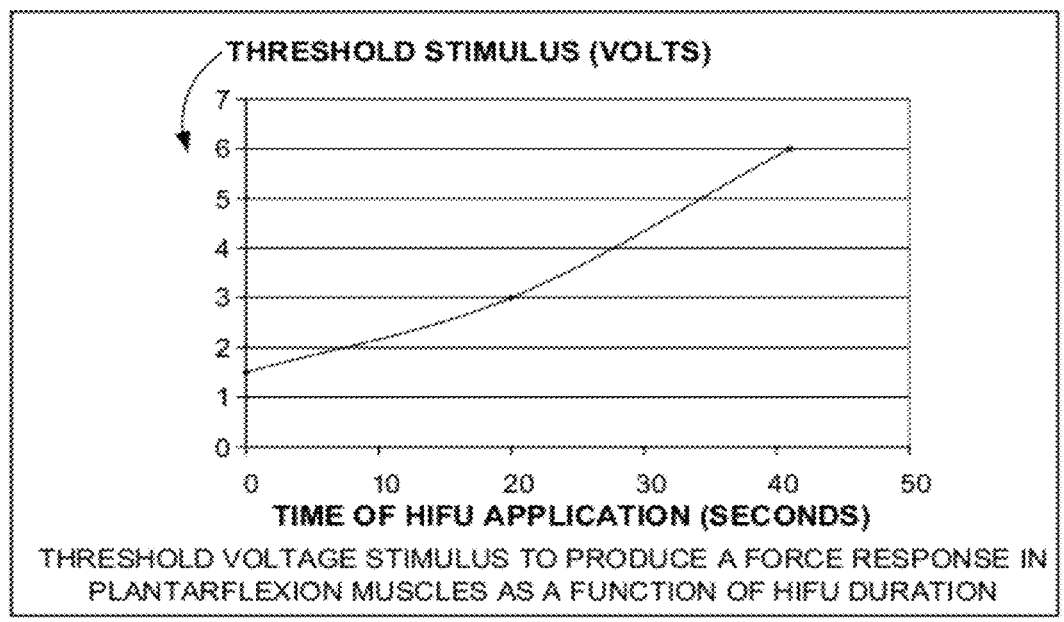
Figure 21:
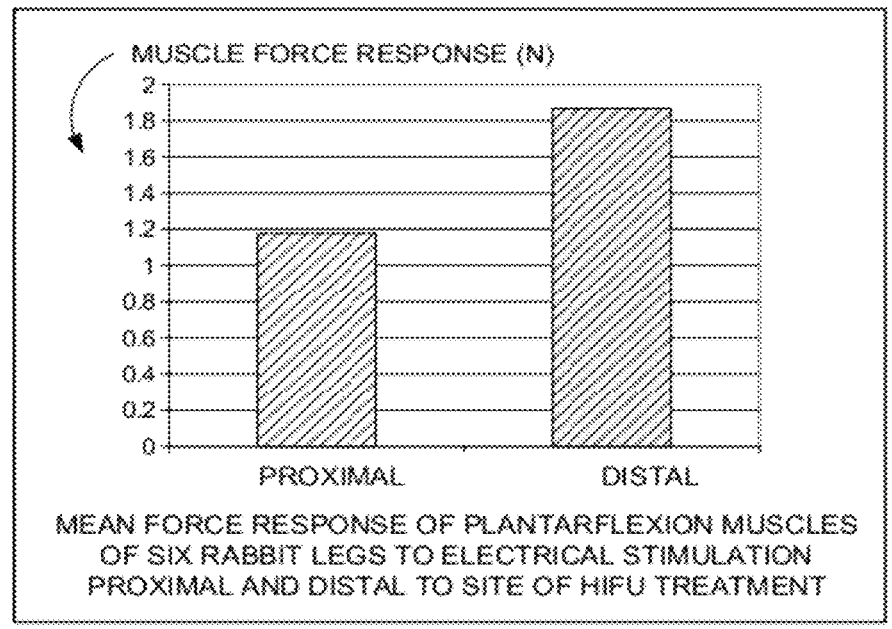
Figure 24:
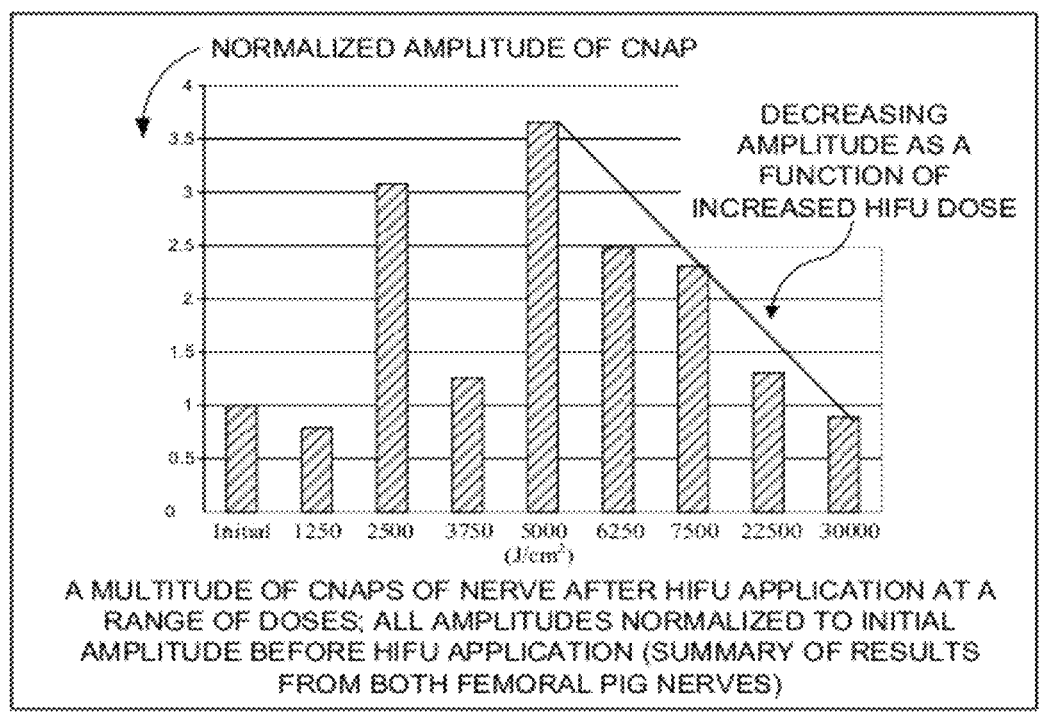
Figure 22:
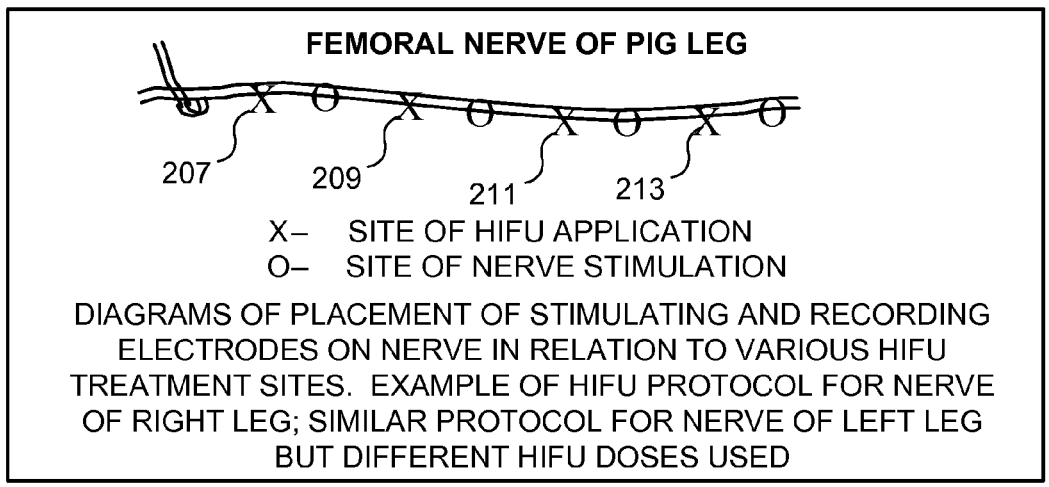
Figure 23:
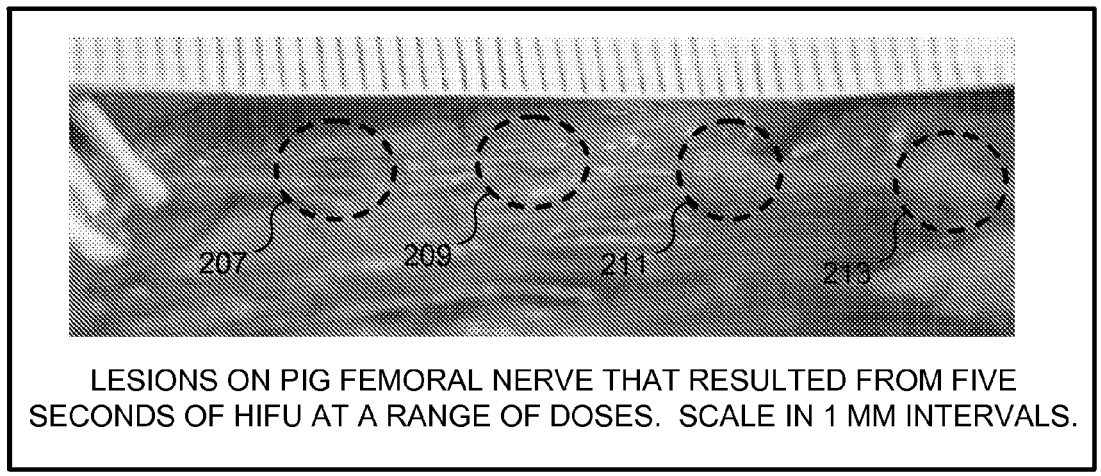
Figure 25:
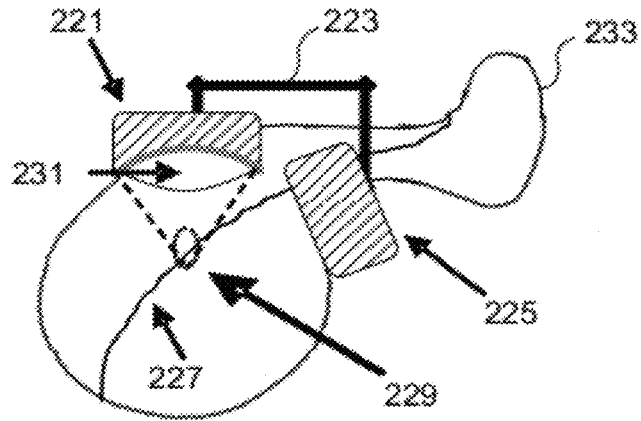
Figure 26:
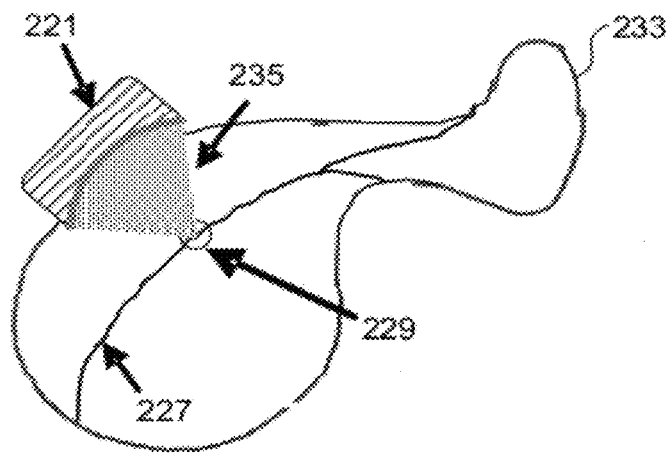
Figure 27:
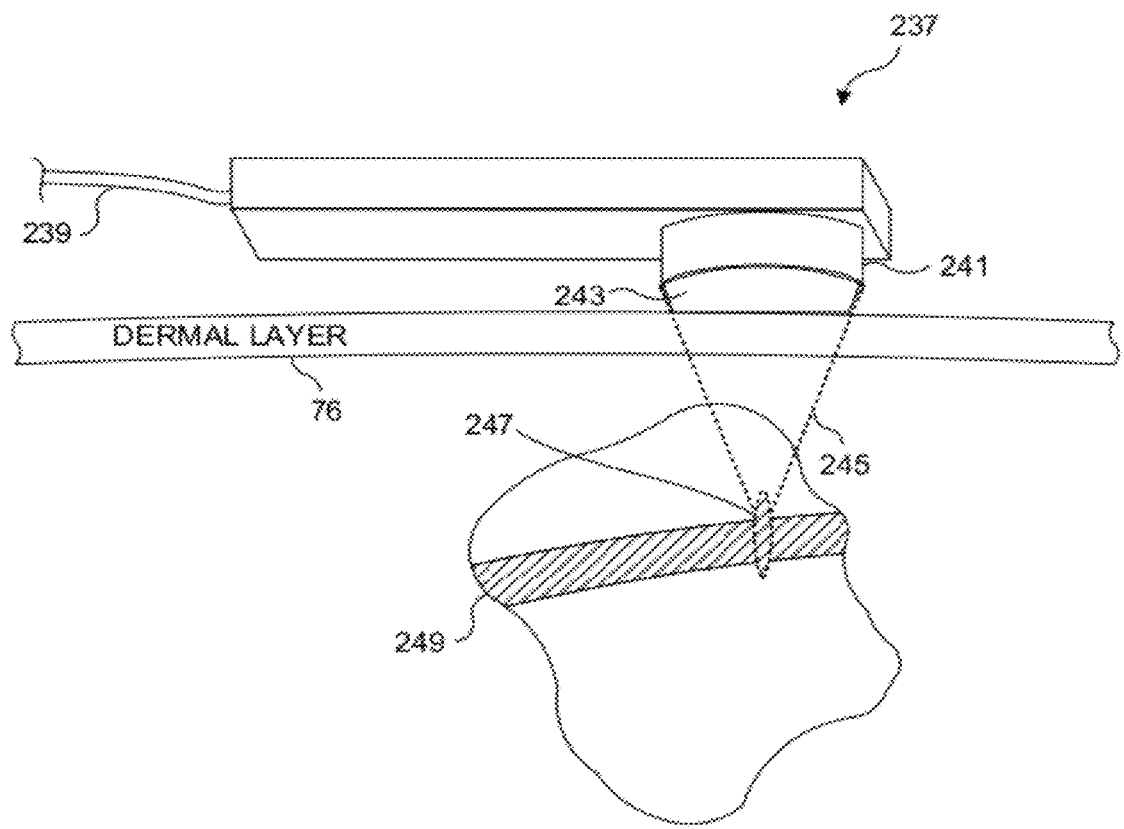

FIG. 5C schematically illustrates an exemplary image provided by the system of FIG. 5B, enabling a clinician to determine how to manipulate a spatial relationship between an imaging probe and a therapy probe to ensure visualization of the focal point of a HIFU beam during therapy;

FIG. 6A schematically illustrates a HIFU therapy probe including a hydrogel standoff/coupling being employed to deliver HIFU transcutaneously to a sub-dermal neural target;

FIG. 6B schematically illustrates an ultrasound imaging probe and a HIFU therapy probe being used together to achieve transcutaneous image guided HIFU therapy of a neural target in accord with the present invention;

FIG. 6C schematically illustrates an ultrasound imaging probe, a HIFU therapy probe and a needle being used together to achieve transcutaneous image guided HIFU therapy of a neural target in accord with the present invention, the needle being readily visible in the ultrasound image and facilitating guidance of the HIFU therapy;

FIG. 7 is a flowchart illustrating the logical steps implemented in a method for using HIFU therapy to treat the nervous system in accord with the present invention;

FIG. 8A is a photograph of a HIFU therapy probe and an ultrasound imaging probe coupled to a frame to ensure that the focal region of the HIFU therapy probe can be visualized in the imaging plane of the ultrasound imaging probe, this HIFU therapy device being used in empirical studies;

FIG. 8B schematically illustrates a transparent sheet configured to overlay an ultrasound image generated by the ultrasound imaging probe of FIG. 8A, with an icon indicating the position of the focal region in the ultrasound image, so that the focal region can be visualized even when the HIFU therapy probe is not energized;

FIG. 8C schematically illustrates the HIFU therapy device of FIG. 8A being used with a gel phantom to enable the focal region of the HIFU transducer to be visualized in an ultrasound image via an icon;

FIG. 8D is an ultrasound image generated using the HIFU therapy device of FIG. 8A, with interference from the HIFU transducer being shifted away from the visualization of the focal region of the HIFU transducer, clearly showing the icon coinciding with a lesion formed by the HIFU;

FIG. 9A schematically illustrates a rabbit's leg coupled to a strain gauge to facilitate empirical studies of HIFU therapy applied to the sciatic nerve of a rabbit;

FIG. 9B schematically illustrates measurement electrodes employed to measure nerve conduction in conjunction with empirical studies of HIFU therapy applied to the sciatic nerve of a rabbit;

FIG. 9C schematically illustrates a HIFU therapy probe and ultrasound imaging probe being used to achieve ultrasound image guided HIFU therapy of the sciatic nerve of a rabbit;

FIG. 9D schematically illustrates how the focal region of the HIFU therapy probe of FIG. 9C is scanned across the sciatic nerve of the rabbit, enabling a HIFU transducer having a relatively small focal region to treat a relatively larger neural structure;

FIG. 9E is a photograph of the HIFU therapy device of FIG. 8A being used to apply therapeutic ultrasound the sciatic nerve of a rabbit via an incision;

FIGS. 10A and 10B are pressure field maps of the HIFU transducer of FIG. 8A which were used to determine the axial and lateral full-width, half-maximum dimensions of the focal region of the HIFU transducer;

FIGS. 11A-11H are ultrasound images obtained during empirical studies of HIFU therapy of the sciatic nerve of a rabbit using the HIFU device of FIG. 8A;

FIGS. 12A-12F are photographs of HIFU induced lesions on the sciatic nerve of a rabbit produced during the above noted empirical studies;

FIG. 13 is a cross-sectional image of rabbit tissue showing a HIFU induced lesion extending through the sciatic nerve into adjacent muscular tissue;

FIGS. 14A &14B, 14C & 14D, 15A & 15B, and 16A & 16B, are microscopic images of rabbit neural tissue before and after (respectively) HIFU therapy;

FIGS. 16C & 16D are microscopic images of rabbit neural tissue after HIFU therapy;

FIG. 17 schematically illustrates a different HIFU therapy probe being used to achieve HIFU therapy of the sciatic nerve of a rabbit in another empirical study;

FIG. 18 graphically illustrates compound nerve action potentials before and after HIFU therapy of the sciatic nerve of a rabbit;

FIG. 19 graphically illustrates compound nerve action potentials as a function of increasing doses of HIFU therapy of the sciatic nerve of a rabbit;

FIG. 20 graphically illustrates the threshold voltage stimulus required to produce a force response as a function of increasing duration of HIFU therapy of the sciatic nerve of a rabbit;

FIG. 21 graphically illustrates a mean force response to electrical stimulation distal to proximal of application of HIFU therapy of the sciatic nerve of a rabbit;

FIG. 22 schematically illustrates HIFU therapy of the femoral nerve of a pig in a plurality of different sites;

FIG. 23 is a photograph of HIFU induced neural lesions in the femoral nerve of a pig;

FIG. 24 graphically illustrates compound nerve action potentials for a plurality of different HIFU doses applied to the sciatic nerve of a rabbit;

FIG. 25 schematically illustrates yet another HIFU therapy device being used to achieve ultrasound image guided HIFU therapy of the sciatic nerve of a rat, in which the focal region of the HIFU transducer is larger than the neural treatment site;

FIG. 26 schematically illustrates another HIFU therapy device being used to achieve direct guided HIFU therapy of the sciatic nerve of a rat, in which the focal region of the HIFU transducer is larger than the neural treatment site; and FIG. 27 schematically illustrates still another HIFU therapy device being used to achieve direct guided HIFU therapy of a neural structure, in which the focal region of the HIFU transducer is larger than the neural structure.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Overview of the Concepts Disclosed Herein

The concepts disclosed herein encompass a method for using HIFU to treat nerves. Nerves can be targeted to alleviate pain, to provide an anesthetic effect, or to reduce spasticity. HIFU treatment of nerves offers potential to replace Botox (i.e., BTX) injections to achieve a cosmetic effect, as discussed in greater detail below. Depending on the dose of HIFU delivered to the nerve, a relatively temporary blockage or a relatively permanent blockage can be achieved. Furthermore, depending on how much of a nerve is treated, a partial conductive block or a complete conductive block can be achieved. Because of the relatively small size of nerves, and the potential for HIFU beams to damage non-target tissue, it is particularly important to accurately position the focal point of the HIFU transducer on a carefully selected portion of the nervous system before beginning treatment. It is also important to be able to visualize the focal point of the HIFU beam in real-time, to ensure that the focal point is properly positioned relative to a target nerve, and to monitor treatment to ensure that damage to non-target tissue does not occur (or such damage is minimal). A particularly preferred embodiment of the present invention synchronizes ultrasound imaging with HIFU to achieve ultrasound image guided HIFU therapy of nerves. Alternatively, Magnetic Resonance Imaging (MRI) can be used instead of ultrasound. MRI imaging does have a small latency (and thus, is not "real-time" imaging), but the latency is sufficiently small so that MRI is usable to achieve image guided HIFU therapy of nerves.

Various combinations of HIFU transducers and imaging transducers can be beneficially employed. The HIFU transducer and imaging transducer can be integrated into a single instrument. A separate HIFU therapy probe and ultrasound imaging probe can be employed. Depending on the location of the nerve being targeted, one or more of the HIFU transducer and imaging transducer can be disposed external of the patient, or in a body cavity of the patient. For embodiments in which the HIFU transducer and imaging ultrasound transducer are implemented on separate probes, the use of a frame to maintain the proper spatial orientation between the probes is useful. In the following description, a synchronization technique useful to enable real-time ultrasound image guided HIFU therapy to be achieved is described. The techniques of using HIFU to treat nerves in accord with the present invention is then discussed in detail, including a discussion of relevant empirical data.

The terms "therapeutic transducer," "HIFU transducer," and "high intensity transducer," as used herein and in the claims that follow, all refer to a transducer that is capable of being energized to produce ultrasonic waves that are much more energetic than the ultrasonic pulses produced by an imaging transducer, and which can be focused or directed onto a discrete location, such as a treatment site in a target area. However, in at least one embodiment of the present invention, not all ultrasonic waves produced by such a transducer are necessarily at a high intensity, as is explained below.

The concepts disclosed herein encompass using HIFU therapy to treat neural structures. The term neural structures is intended to encompass all anatomical structures associated with nervous systems including peripheral nerves, sensory nerves, spinal mot nerves, nerve endings, motor endplates, all other nerves, and regions of the brain. Many of the examples included below specifically refer to treating a nerve (as opposed to a different neural structure); however, such examples are not intended to limit the invention. It should be understood that these concepts can be applied to neural structures in general, and not simply to nerves alone.

Synchronizing Imaging and HIFU to Achieve Real-Time Image Guided Therapy

When administering HIFU therapy, it is very desirable to be able to observe a treatment site, to ensure that lesions induced by the HIFU therapy are being produced at the desired location. Failure to properly aim the HIFU beam will result in undesired tissue necrosis of non-target tissue. From a practical standpoint, this goal has not proven easy to accomplish when ultrasound is used to visualize the focal point, because the HIFU beam used for therapy completely saturates the signal provided by the imaging transducer. One analogy that might help to make this problem clear relates to the relative intensities of light. Consider the light coming from a star in the evening sky to be equivalent to the low power imaging ultrasound waves that are reflected from a target area toward the imaging transducer, while the light from the sun is equivalent to the HIFU generated by the therapy transducer. When the sun is out, the light from the stars is completely overwhelmed by the light from the sun, and a person looking into the sky is unable to see any stars, because the bright light from the sun makes the dim light coming from the stars substantially imperceptible. Similarly, the HIFU emitted by the therapy transducer completely overwhelms the ultrasonic waves produced by the imaging transducer, and any ultrasonic image generated is completely saturated with noise caused by the HIFU emitted from the therapeutic transducer.

Figure 1A:
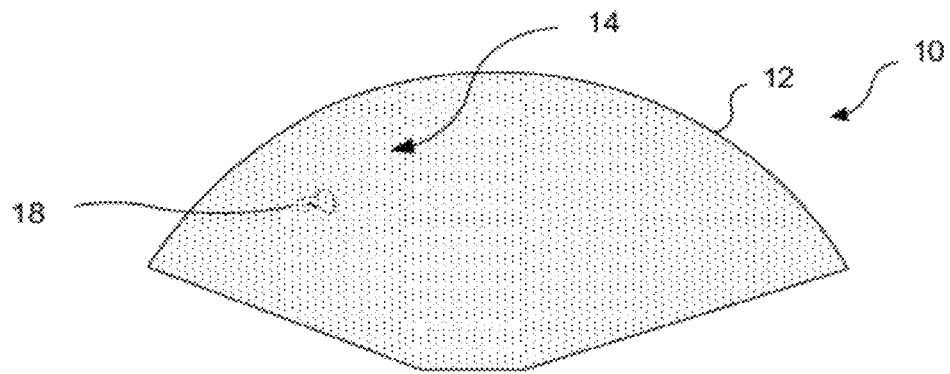

FIG. 1A illustrates an ultrasound image 10 in which a scanned image field 12 is completely obscured by noise 14, as is typical during the simultaneous reception of energy from a reflected imaging pulse and a HIFU wave (neither shown). In regard to ultrasound image 10, a clinician may desire to focus the HIFU wave on a treatment site 18. However, because noise 14 completely saturates scanned image field 12, it is virtually impossible to accurately focus the HIFU wave onto treatment site 18. If the therapy transducer is completely de-energized, noise 14 is eliminated from the scanned image field. However, under these conditions, the focal point of the HIFU wave will not be seen, and thus, the HIFU wave cannot be accurately focused on treatment site 18. While some change in echogenicity at the HIFU focal point will persist for a time after the HIFU wave is no longer present, any change in a position of the therapy transducer (or treatment site 18) will not register until the therapeutic transducer is re-energized, and thus, the HIFU wave cannot be focused in real-time.

Some prior art systems have included a targeting icon in an ultrasound image to indicate the position of the known focal point of a specific HIFU transducer in a scanned image. While this icon may be helpful in determining whether the HIFU was previously focused, it still does not enable a clinician to observe real-time results. Once the HIFU therapeutic transducer is energized, the scanned ultrasound image is completely saturated with noise, and the clinician cannot monitor the progress of the treatment without again de-energizing the HIFU therapeutic transducer.

Figure 1B:
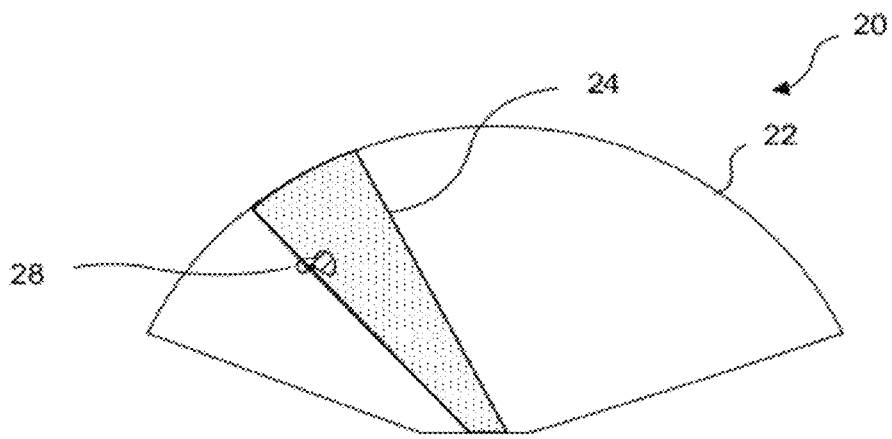

FIG. 1B illustrates one technique in which the effect of noise disrupting the ultrasound image is reduced. In FIG. 1B, the HIFU wave generated by the therapeutic transducer has been pulsed. This technique produces an ultrasound image 20, in which the location of noise 24 in a scanned field 22 is a function of the interference between the pulsed HIFU wave generated by the therapy transducer and the ultrasonic imaging ultrasound pulses generated by the scanning transducer. In FIG. 1B, noise 24 substantially masks a treatment site 28. This result will not occur in all cases, because to an observer, noise 24 will move across scanned field 22 as the interference between the HIFU waves and the imaging pulses varies in time. Pulsing of the HIFU wave alone can thus enable the clinician to view a noise-free image of the treatment site only when noise 24 is randomly shifted to a different part of scanned field 22, away from the treatment site. However, this pulsing of the HIFU beam generates an image that is extremely distracting to a clinician, as noise 24 flickers across scanned field 22, making it difficult to concentrate and difficult to consistently determine where the focal point of the HIFU wave is relative to the treatment site, in real-time.

Figure 1C:
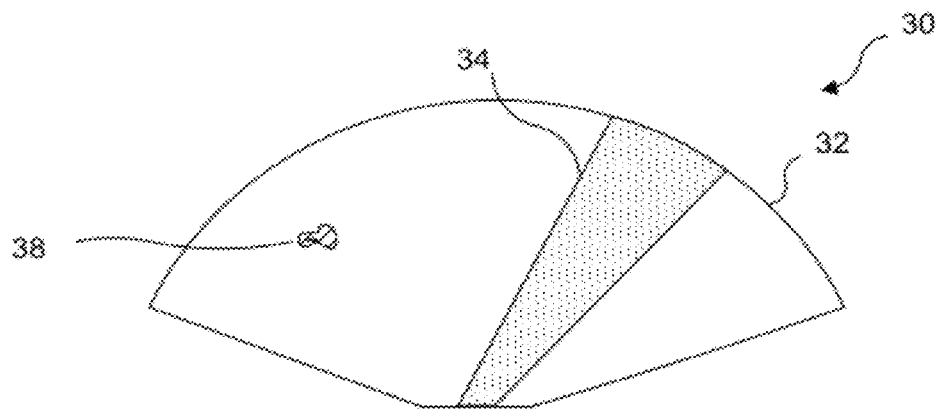

FIG. 1C illustrates an ultrasound image 30 in which a HIFU wave from a therapy transducer has been both pulsed and synchronized with respect to the ultrasonic imaging pulses from an imaging transducer, to ensure that noise 34 does not obscure a treatment site 38. In ultrasound image 30, noise 34 has been shifted to a location within a scanned field 32 of the image that is spaced apart from treatment site 38, by selectively adjusting both the pulsing and the synchronization of the HIFU wave relative to the image pulses. Preferably, noise 34 is shifted completely away from treatment site 38, enabling the clinician to view a noise-free, stable image of treatment site 38 that clearly shows the location of the focal point of the HIFU wave relative to the treatment site. Thus, the HIFU wave can be focused in real-time onto treatment site 38, and a clinician can, in real-time, view the therapeutic effects of the HIFU wave on treatment site 38. It will therefore be apparent that a clinician can de-energize the therapeutic transducer, terminating the generation of the HIFU wave as soon as a desired therapeutic effect has been achieved at the treatment site. In this manner, undesired effects on non-target tissue can be minimized.

Figure 2:
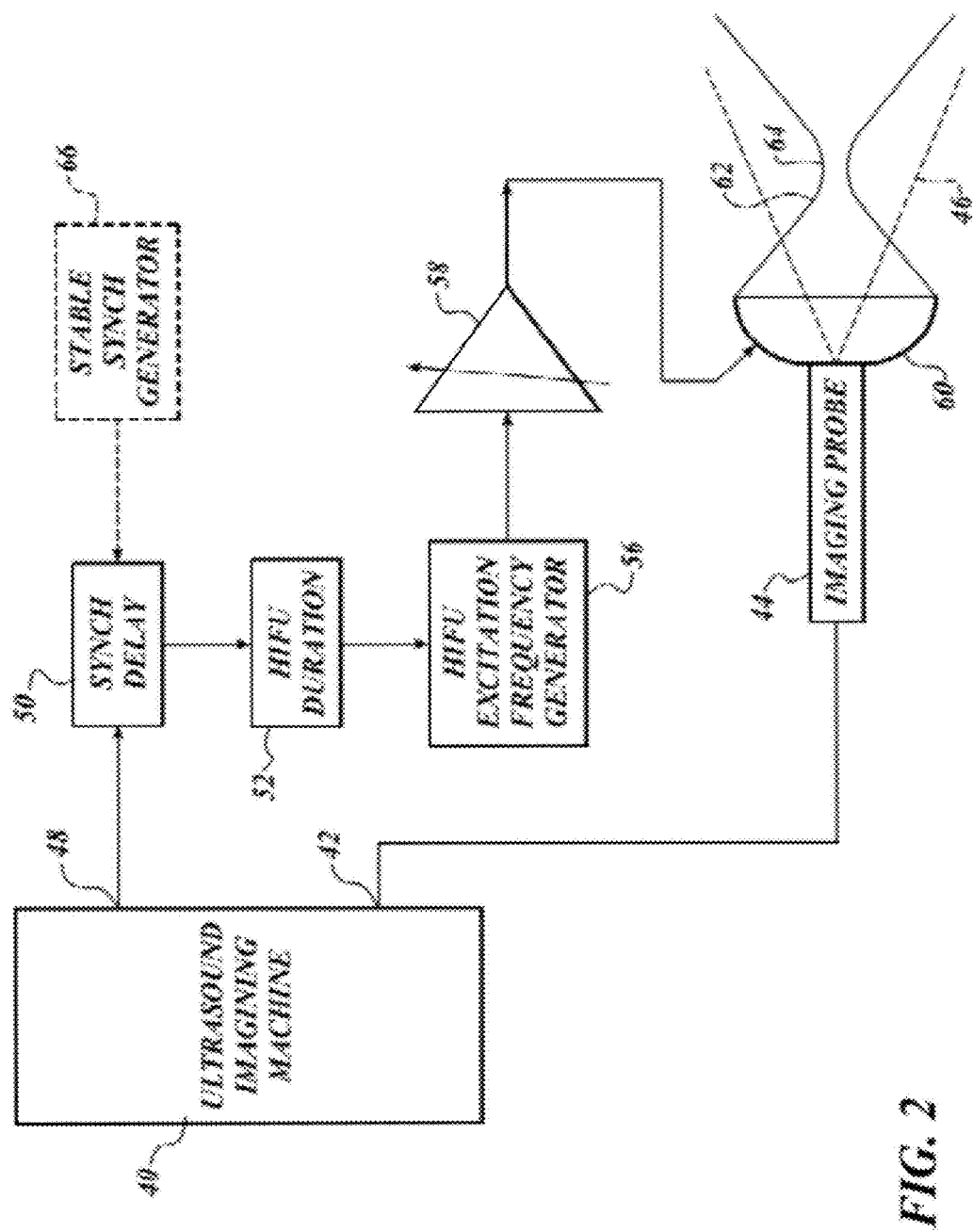

FIG. 2 illustrates a block diagram of an embodiment of the present invention that synchronizes the image and HIFU waves required for the simultaneous imaging and therapy in real-time. An ultrasound imaging machine 40 is an ultrasound imaging system of the type that is well known to those of ordinary skill in the art and can be purchased from vendors such as ATL Inc., of Bothell, Wash. An imaging probe 44 is also of a type well known to those of ordinary skill in the art is connected to ultrasound imaging machine 40 via a cable 42. Imaging probe 44 generates ultrasonic imaging pulses that propagate to the target area, are reflected from structures and tissues within the body, and are received by the imaging probe. The signal produced by the imaging probe in response to the reflected ultrasound waves is communicated to the ultrasound imaging machine through cable 42 and processed to provide a visual representation of the structure and tissue that reflected the ultrasonic imaging pulses. An imaging beam sector 46 from imaging probe 44 is identified in the Figure by dash lines. Also included in the present invention is a therapeutic transducer 60. When excited, this therapeutic transducer generates HIFU waves that are focused at a particular point of interest, i.e., a treatment site within a patient's body. In FIG. 2, the path of a HIFU beam 62 is indicated by dotted lines. HIFU beam 62 narrows to a focal point 64. Those of ordinary skill in the art will recognize that the position of focal point 64 relative to therapeutic transducer 60 is a function of the geometry of the therapeutic transducer and will normally depend upon the application. For example, a therapeutic transducer that will be used to apply HIFU therapy to the nervous system of a patient from within a body will have a different optimum focal point than a therapeutic transducer used to apply treatment to the nervous system from outside a patient's body. It should also be understood that therapeutic transducers having a fixed focal length can be employed, or an array of therapeutic transducers having a variable focal length can be employed. While arrays of therapeutic transducers require more sophisticated control systems, such arrays offer the benefit of enabling therapy probes having multiple focal lengths to be achieved. When a therapy probe having a fixed focal length is employed, and an initial positioning of that therapy probe does not result in the focal point of the therapy transducer being incident on the desired portion of the nervous system, in general the therapy probe itself will need to be repositioned until the focal point of the therapy transducer is properly positioned relative to the nervous system. When a therapy probe including an array of therapy transducers having variable focal lengths is employed, and the initial positioning of the therapy probe does not result in the focal point of the therapy transducers being properly positioned relative to the nervous system, the array can be manipulated to vary the focal length of the therapy transducers until the focal point is properly positioned. Of course, there may be times when the initial positioning is so far off that the therapy probe itself still must be moved.

It should be noted that ultrasound imaging machine 40 differs from prior art systems in several ways, including its inclusion of a synchronization output signal 48. Preferably, ultrasound imaging machine 40 is modified to enable synchronization output signal 48 to be obtained. Because such a synchronization output signal has not been required for prior art ultrasonic imaging applications, provision of a synchronization output signal has generally not been made in prior art ultrasound imaging machines. If a prior art imaging machine that has not been modified to provide synchronization output signal 48 is used, the synchronization output signal can instead be derived from the ultrasonic imaging signal conveyed by cable 42.

Synchronization output signal 48 is supplied to a synchronization delay circuit 50. Synchronization delay circuit 50 enables the user to selectively vary the initiation of each HIFU wave with respect to each sequence of ultrasonic imaging pulses that are generated to form an ultrasonic image. Referring to FIG. 1C, delay 50 enables a user to vary the position of noise 34 in scanned field 32, so that the noise is moved away from treatment site 38, to a different portion of scanned field 32. The user is thus provided a noise-free image of treatment site 38.

A HIFU duration circuit 52 is used to control the duration of the HIFU wave. A longer duration HIFU wave will apply more energy to the treatment site. Generally, the more energy that is applied to a treatment site, the faster a desired therapeutic effect will be achieved. However, it should be noted that if the HIFU wave is too long, the duration of noise 34 as shown in ultrasound image 30 will increase and can extend into the next ultrasound imaging pulse to obscure treatment site 28, or may completely obscure ultrasound image 30, generating a display very similar to ultrasound image 10 in FIG. 1A. Thus, the user will have to selectively adjust HIFU duration circuit 52 to obtain a noise-free image of treatment site 38, while providing a sufficient level of energy to the treatment site to effect the desired therapeutic effect in an acceptable time.

A HIFU excitation frequency generator 56 is used to generate the desired frequency for the HIFU wave, and a power amplifier 58 is used to amplify the signal produced by the HIFU excitation frequency generator to achieve the desired energy level of the HIFU wave; power amplifier 58 is thus adjustable to obtain a desired energy level for the HIFU wave. Optionally, a stable synchronization signal generator 66 can be used to synchronize the HIFU wave to the imaging ultrasonic wave, instead of using synchronization output signal 48 from ultrasound imaging machine 40. Stable synchronization signal generator 66 can be used to provide a stable synchronizing pulse to initiate the HIFU wave, and the timing of this stable synchronizing pulse can be selectively varied until a noise-free image of the treatment site has been obtained. A drawback of using stable synchronization signal generator 66 instead of synchronization output signal 48 is that any change in the timing of the ultrasound imaging pulses, such as is required to scan deeper within tissue, will require an adjustment to stable synchronization signal generator 66 that would not be required if synchronization output signal 48 were used. The processor will be able to automatically find a stable synchronization signal using information from the movement of the noise.

Figure 4:
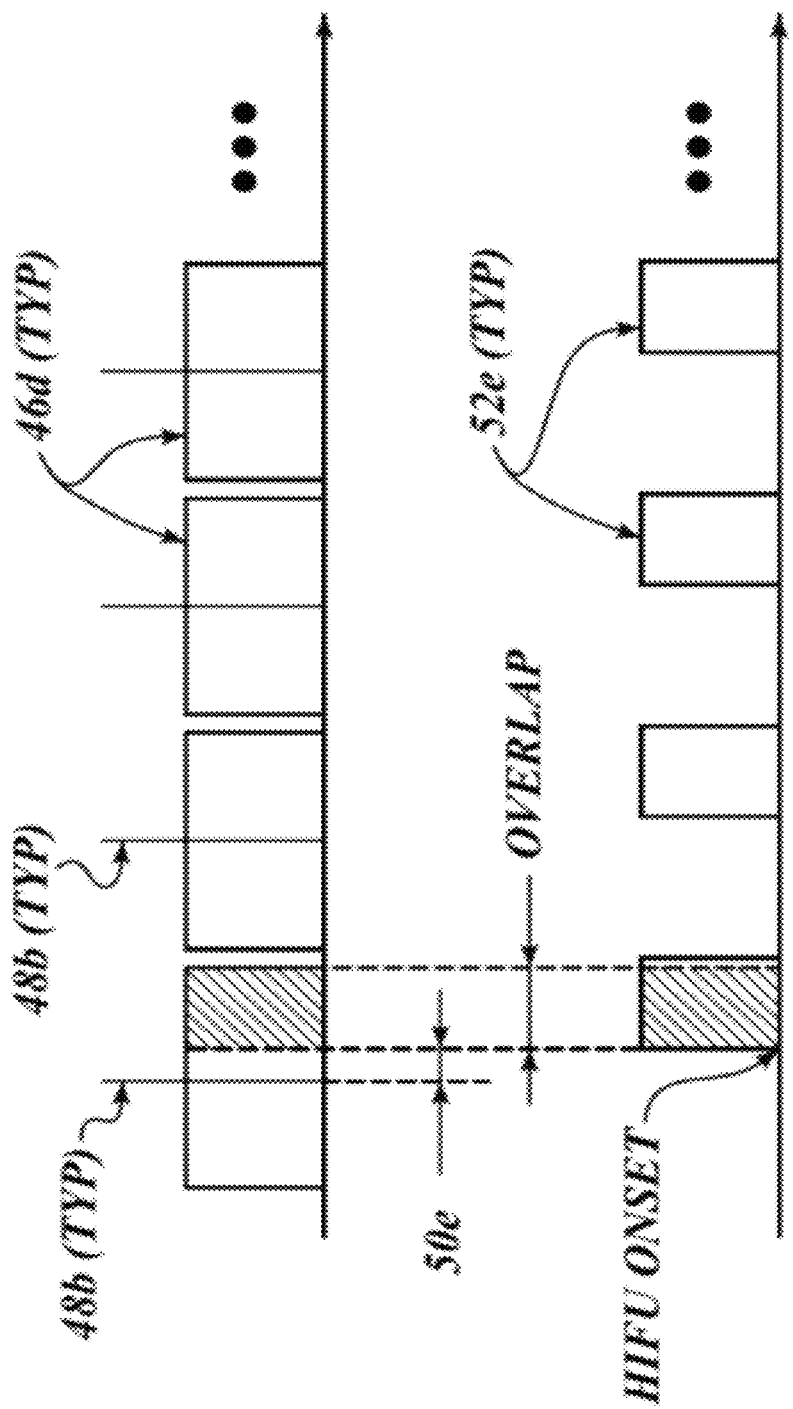
FIG. 4 illustrates yet another timing and synchronization pattern for synchronizing the HIFU and imaging scans.

FIGS. 3A(1)-3D(4) and FIG. 4 provide further detail for the synchronization and pulsing features of the present invention. FIG. 3A(1) shows ultrasound imaging pulses 46a produced by imaging machine 40 and imaging probe 44 that are used to acquire an ultrasound image of a target area (such as ultrasound image 30 of FIG. 1C). A synchronization pulse 48a is shown in FIG. 3A(2). It should be noted that synchronization pulse 48a is illustrated as occurring before the generation of ultrasound imaging pulses 46a; however, the timing of synchronization pulse 48a relative to the imaging pulses is not critical, so long as it is stable. Synchronization pulse 48a merely establishes a timing reference point, from which a delay 50a (shown in FIG. 3A(3)), used for the initiation of the HIFU wave, is set such that noise from the HIFU wave in an ultrasonic image generated by imaging pulses 46a is shifted away from the image of the treatment site. Delay 50a is not fixed; instead, it is adjusted by the user until a noise-free image of the treatment site is obtained.

A HIFU duration 52a, shown in FIG. 3A(4), determines the duration of the HIFU wave. HIFU duration 52a may be very brief, as shown in FIG. 3A(4), or extended, as shown in FIGS. 3B(4) and 3C(4). An increase in the duration of the HIFU wave will cause a greater portion of an ultrasound image to be obscured by noise, and may cause the HIFU wave to interfere with the image of the treatment site. In FIG. 3A(4), delay 52a is very short, and the resulting noisy region in the ultrasound image is very small. However, a short duration HIFU wave means a correspondingly small amount of HIFU energy will be delivered to the treatment site, thus increasing the length of the treatment. A clinician must balance the length of HIFU duration needed to maintain a noise-free image of the treatment site against the time required to complete the therapy. It should be noted that as an alternative to using HIFU duration 52a to control the HIFU excitation frequency generator to variably set the duration of the HIFU wave, the HIFU excitation frequency generator itself can be adjusted to control the duration.

FIGS. 3B(1)-3C(4) similarly illustrate timing patterns that incorporate different settings for the delay relating to the initiation of the HIFU wave (delay 50b in FIG. 3B(3), and delay 50c in FIG. 3C(3)) and the delay relating to the duration of the HIFU wave (duration 52b in FIG. 3B(4), and duration 52c in FIG. 3C(4)). FIGS. 3D(1)-3D(4) illustrate a timing pattern that enables a longer duration HIFU wave (thus more energy applied to the treatment site) to be used, while still enabling a noise-free image of the treatment site to be generated. In FIG. 3D(1), ultrasound imaging pulses 46a and 46b appear to be much shorter than in FIGS. 3A(1), 3B(1) and 3C(1), but actually are of the same duration, as the scales of FIGS. 3D(1)-3D(4) have been significantly increased. Synchronization pulse 48a of FIG. 3D(2) is obtained and used as described above. A delay 50d in FIG. 3D(3) is set to obtain a noise-free image of the treatment site, also as described above; however, as clarified below, not all of these synchronization pulses govern the image that is produced, because duration 52d dominates. The significant difference between FIGS. 3D(1)-3D(4) and FIGS. 3A(1)-3C(4) is that duration 52d has been significantly increased in FIG. 3D, such that a very long burst of HIFU energy is emitted, almost to the point of continuous emission. Here, the noise-free imaging occurs only every seventh image, during interrogation wave 46b. By adjusting duration 52, more or fewer images will experience interference, and therefore, various duty cycle lengths for HIFU exposure can be accommodated. It should be noted that as the number of images interfered with by the HIFU wave increases (here, 6 out of 7 images), the resulting image of the target area will arguably provide less real-time feedback. However, the actual time between visible images of the treatment site may be so short as to appear to occur in real-time. But, at very high settings for the HIFU duration (such as would cause the HIFU wave to interfere with 99 out of 100 images of the treatment site), the advantages associated with real-time imaging of the treatment site are diminished. Thus, the HIFU duration will preferably not be set so high as to negate the benefits of real-time imaging of the treatment site and its ability to provide the clinician with immediate feedback concerning the effect of the therapy on the treatment site.

FIG. 4 illustrates another timing sequence that shows the relationships between ultrasound imaging pulses 46d, a synchronization pulse 48b, a delay 50e, and a HIFU duration 52e. In this timing sequence, synchronization pulse 48b occurs during the ultrasound imaging pulses 46d, rather than preceding the ultrasound imaging pulses, as shown in FIGS. 3A-3D. As noted above, the position of each synchronization pulse 48b relative to the ultrasound imaging pulses is not critical, since delay 50e is adjusted to shift the noise away from the image of the treatment site. Again, the duration of the HIFU wave (and thus, the energy applied to the treatment site) is varied either by adjusting duration 52e, as shown in FIG. 4, or by adjusting the HIFU excitation generator.

Imaging of HIFU Focal Point

It will often be important for a clinician to be able to confirm that the focal point of a HIFU transducer is directed at a desired treatment site before initiating HIFU therapy. It has been determined that if the energy level of a HIFU transducer is reduced to a level less than a level that would cause any damage to tissue, the focal point of the HIFU transducer will still be evident within the target area displayed in the image developed from the reflected ultrasound signal produced and received by the ultrasound imaging transducer. The focal point will appear as a bright spot in the displayed image and will rapidly fade over time. Thus, it is possible for a clinician to move the HIFU transducer as necessary to shift the focal point to a desired treatment site in the target area being imaged by the ultrasound imaging transducer and to see the focal point in the image as a bright spot that moves as the position of the HIFU transducer is changed. Only after the focal point is positioned on a desired treatment site will the clinician increase the energy of the ultrasound pulses produced by the HIFU transducer to a level sufficient to achieve the desired therapeutic effect, e.g., to a level sufficient to necrose tissue, to cause hemostasis, or to otherwise treat a neural structure by thermal and mechanical effects. It should be noted that the ultrasound imaging transducer is not receiving the ultrasound signal produced by the HIFU transducer that is reflected by the tissue, but instead, is imaging the effect of the change in echogenicity of the tissue caused by the relatively low energy ultrasound burst produced by the HIFU transducer. This technique can be used with any of the HIFU based therapy methods discussed below.

A further advantage of the preceding technique for imaging the focal point of a HIFU transducer can be achieved by storing the image of each successive treatment site, which will appear as a bright area in the image produced by the ultrasound imaging transducer system. For example, a storage type display, which is readily available, can be used for this purpose. By storing the image of each treatment site to which the HIFU therapy has previously been administered during a current session, it is possible for a clinician to target spaced-apart treatment sites in the target area, thereby ensuring the HIFU therapy has been administered to all of the desired portion of a tumor or other structure in the patient's body. Since each previous treatment site will be visible in the image, it will be apparent that a desired pattern of treatment sites can readily be laid down over the tumor or other structure of interest. The change in echogenicity caused by a relatively high energy therapeutic HIFU wave will be brighter and persist longer in the display, enabling the clinician to easily distinguish between a current prospective focus point for the next treatment site (produced using the low energy pulse) and the previous treatment sites to which the higher energy HIFU therapy has already been administered.

Exemplary Imaging and Tracking Systems

In FIG. 5A, a block diagram is illustrated for a system 200 that enables imaging of a target area in 3D and storing of the locations of treatment sites to which the HIFU therapy has been administered in the 3D image as a HIFU therapy session proceeds. The system includes a 3D image data processor and display 202, an image acquisition section 204, a magnetic field sensor 206, a magnetic field generator 208, and six-dimensional (6D) electronic processing circuitry 210. The latter three components are employed to track the imaging target area and the HIFU focal point as they are redirected in the 3D space and are part of a 6D measurement system (i.e., three spatial coordinates for the 3D orthogonal axes and three angles of rotation around these three orthogonal axes). A 6D measurement system is commercially available from Ascension Technology, Milton, Vt. This 6D measurement system uses 6D electronic processing circuitry 210 and magnetic field generator 208 to produce time sequential orthogonally oriented magnetic fields covering a general area as indicated in the Figure by the dash line that encompasses the region of magnetic field. Magnetic field sensor 206 is mounted on a combined imaging and HIFU therapy probe 212 in a fixed manner relative to imaging and HIFU transducers 214. The magnetic field sensor detects the magnetic field strength in 3D sequentially produced by the magnetic field generator. The 6D electronic processing circuitry uses the information from the magnetic field sensor and the known magnetic fields that were produced to compute the 3D position and the three angular orientations around the three orthogonal axes of the magnetic field sensor (and thus, of the combined imaging and HIFU therapy probe) with respect to the magnetic field generator, yielding the 6D information. The 6D information is supplied to 3D image data processor and display 202 at a rate sufficient to enable movement of the magnetic field sensor to be tracked in the displayed 3D image of the target area. With information derived from calibrating system 200 with the imaging probe, the position of the target area and the HIFU transducer focal point can be related to a 3D spatial point, so long as magnetic field sensor 206 is within the range of the magnetic field produced by magnetic field generator 208. 3D image data processor and display 202 also receive ultrasound image information from an ultrasound imaging machine 216 through image acquisition section 204. It uses this information to develop and display 3D information. An ultrasound imaging machine 216 provides the synchronization signal to a HIFU control and electrical energy generating system 218, as discussed above. The remaining component in FIG. 5A is a physiological information acquisition section 220, which enables synchronization of the imaging and HIFU therapy with physiological activity, such as respiration or cardiac activity (provided by an electrocardiogram system—not shown). Use of the physiological information avoids problems associated with movement of the patient's body due to physiological activity. For example, 3D imaging and HIFU therapy can be controlled so that they are implemented only at the end of expiration in the breathing cycle, since motion of the patient is more repeatable than at mid inspiration. A physiological sensor such as a respiration detector (not shown), which is well known in the art, can provide the information for this section of the system.

While system 200 has been described in conjunction with a single probe that includes both an imaging transducer and a therapy transducer, those of ordinary skill in the art will readily recognize that system 200 can be modified to track the positions of separate imaging probes and therapy probes.

Yet another aspect of the present invention is directed to a system and method that enables free hand registration of the imaging and therapy probes, which can be employed to target portions of the nervous system for HIFU therapy. FIG. 5B schematically illustrates a system 450 that facilitates such free hand registration. System 450 includes a HIFU therapy probe 452, an ultrasound imaging probe 456, a tracking system 454, and a display 460. It should be understood that any type of HIFU therapy probe (configured for internal or external use), and any type of ultrasound imaging probe (configured for internal or external use), can be used in connection with system 450. Instead of using a physical or mechanical frame to maintain a spatial relationship between the HIFU therapy probe and the ultrasound imaging probe, system 450 relies on tracking system 454 to ensure that the spatial relationship between the HIFU therapy probe and the ultrasound imaging probe enables the focal point of the HIFU therapy probe to be visualized in the imaging plane generated by the ultrasound imaging probe. Tracking system 454 includes a processor that is able to keep track of the spatial relationship between the ultrasound imaging probe and the HIFU therapy probe. Such tracking systems are commercially available and can be obtained from companies such as Ascension Technology, of Milton, Vt. Tracking systems for medical instruments are available based on several different technologies, including acoustic, light, and magnetic based tracking systems, any of which could be used to implement tracking system 454. Magnetic based tracking systems (e.g., the Ascension PC BIRD™) that could be used for medical instruments are available from Mind Flux of Roseville, Australia.

System 450 functions as follows. HIFU therapy probe 452 and ultrasound imaging probe 456 are positioned relative to a patient 458. The clinician can view an image 462 on display 460. Image 462 includes a representation of patient 458, and the relative locations of ultrasound imaging probe 456 and HIFU therapy probe 452. Preferably image 462 will include a visual representation of the imaging plane provided by ultrasound imaging probe 456, and the HIFU beam generated by HIFU therapy probe 452. The clinician can determine from image 462 whether ultrasound imaging probe 456 and HIFU therapy probe 452 are properly aligned, so that the focal point of the HIFU beam can be visualized in an image provided by the ultrasound imaging probe. If the probes are not properly aligned, image 462 will provide the clinician a reference for determining how to reposition one or both of ultrasound imaging probe 456 and HIFU therapy probe 452, so that the focal point of the HIFU beam can be visualized in the ultrasound image. Depending on the size of display 460, the ultrasound image provided by ultrasound imaging probe 456 can be displayed along with image 462, or a separate display can be provided to display the ultrasound image generated by ultrasound imaging probe 456. The astute observer will recognize that image 462 corresponds to FIG. 6B, which is described in greater detail below.

FIG. 5C is an enlarged view of display 460, including an image 463. The relative positions of ultrasound imaging probe 456, patient 458, and HIFU therapy probe 452 are presented in image 463. An image plane 466 provided by ultrasound imaging probe 456, a HIFU beam 468 provided by HIFU therapy probe 452, and a focal point 464 can be visualized in image 463. An optional message 470 informs the clinician that the probes are not properly aligned, which is apparent, because imaging plane 466 and beam 468 do not overlap, and further, because focal point 464 does not lie within image plane 466. While monitoring display 460 and image 463, the clinician can change the relative positions of ultrasound imaging probe 456 and HIFU therapy probe 452, until focal point 464 lies within imaging plane 466.

It should be noted that image 463 is a two-dimensional (2D) image, and those of ordinary skill in the art will readily recognize that even if the HIFU beam and the imaging plane overlap in two dimensions, they may not overlap in three dimensions. When image 463 indicates that the imaging plane and the HIFU beam overlap, a clinician can view the ultrasound image provided by the ultrasound imaging probe, to determine whether the focal point of the HIFU beam can actually be visualized in the ultrasound image. If not, an indication is provided that the spatial relationship and orientation between the imaging plane and the HIFU beam are not properly aligned, and the clinician can further manipulate the relative positions of the imaging probe and/or the HIFU therapy probe, until the focal point of the HIFU beam both overlaps the imaging plane in image 463 and can be visualized in the ultrasound image provided by the ultrasound imaging probe. It should be also understood that tracking system 454 can provide additional images from different perspectives (or image 463 could be rotated by tracking system 454) to provide feedback to a clinician indicating which direction the ultrasound imaging probe and/or the therapy probe should be manipulated, so that the HIFU beam can be visualized in the image provided by the ultrasound imaging probe.

System 450 offers several advantages, including ease-of-use, the ability to visualize complex treatment strategies, and the ability to visualize complex nervous system geometries.

Use of Anesthetic Agent to Enhance Image of Low Power HIFU at a Treatment Site

While operating a HIFU transducer at a substantially reduced power to determine the location of its focal point within a target area will produce a bright spot visible in the image, it may sometimes be desirable to enhance the visibility of the focal point in the image—in either a 2D or 3D image. The change in echogenicity of the tissue due to the administration of a relatively low power HIFU wave to the tissue enables the location to be seen in the image of the target area. However, it is believed that a substantially brighter spot showing where the HIFU wave (at low power) was focused can be achieved if an anesthetic agent or other blood soluble agent having a relatively high vapor pressure has previously been administered to the patient. Use of such agents, which will readily vaporize when exposed to the slight elevated temperatures caused by low power ultrasound acting on tissue, should produce small bubbles at the focal point of the HIFU transducer. These bubbles will produce a substantially brighter spot in the ultrasound image and at an even lower energy level of the HIFU transducer than the spots produced by the low energy HIFU waves when no such agent has been administered to the patient. Reduction of the HIFU energy to an even lower level when determining the focal point will further ensure that the focal point of the HIFU transducer can be seen in the ultrasound image produced by the imaging transducer without risk of damage to tissue that is not intended to be treated.

Advantage of Simultaneous, Real-Time Imaging

Major advantages in achieving real-time imaging of therapeutic HIFU while it is being applied are: (1) the HIFU treatment can be stopped when a HIFU induced lesion has grown to the point at which it begins to extend beyond the desired treatment site, so that the HIFU focal point can then be repositioned to another treatment site and HIFU therapy reactivated; (2) the focal point of the HIFU wave can be observed in the image due to changes in the echogenicity of the tissue at the focal point, which are apparent in the images of the target area, providing an instant feedback that can enable a clinician to adjust the focal point onto a desired treatment site; (3) the HIFU focal point can be adjusted during the administration of the HIFU therapy to compensate for tissue movement within the patient's body due to breathing or for other reasons; (4) real-time visualization of a treatment site is very reassuring to the medical therapist, in confirming that the HIFU energy is being applied to the correct position (and that healthy tissue is not being damaged); and (5) the combined imaging and therapeutic treatment can be accomplished much faster than in the past, when it was necessary to render treatment, stop the treatment, image the site, and then continue the treatment.

Two methods for HIFU therapy visualization are MRI and ultrasound, and both can be used to image the nervous system. Ultrasound imaging has the advantage of requiring less expensive and more portable instrumentation, compared with MRI. Empirical studies have shown that synchronized ultrasound imaging provides real-time imaging of the HIFU treatment. MRI provides imaging visualization of the HIFU thermal field and coagulated region within about five seconds of treatment and is thus not truly a real-time visualization. But, the MRI latency may be acceptable, particularly if MRI enables greater resolution to facilitate treatment of very fine neural structures. With ultrasound imaging, treating multiple sites within the nervous system, or treating a neural structure larger than the focal region of the HIFU transducer, is facilitated, since the HIFU-induced hyperechoic spot remains after treatment for a duration dependent on the exposure intensity. Furthermore, treatment dosimetry, and not just treatment location, can be determined, since the hyperechoic spot size is proportional to the size of the lesion created, which is important with respect to the treatment of the nervous system using HIFU, because initial studies have indicated a dose effect. As described in greater detail below, nerve conduction can be disrupted on a relatively temporary basis or on a relatively permanent basis depending on the dose of HIFU delivered to the nerve.

Useful Therapy Probes, Imaging Probes, and Frames

The present invention for treating a portion of the nervous system using HIFU therapy can be implemented using a variety of different ultrasound imaging probes and ultrasound therapy probes. Combination probes, where the therapeutic ultrasound transducer and the imaging ultrasound transducer are combined on a single probe are particularly useful if the combination probe is intended to be introduced into a body cavity. In such combination probes, the spatial relationship between the imaging transducer and the HIFU transducer is generally static, because both the scanning transducer and the HIFU transducer are combined in a single instrument. Movement of the probe will generally not move the focal point of the HIFU transducer out of the imaging plane of the scanning transducer, because both transducers are part of the combination probe. Some combination probes are based on prior art imaging probes to which a therapy head has been retrofitted, while other combination probes integrate the imaging and therapy transducers into a single new device.

The present invention can also be implemented using separate imaging probes and therapy probes. One advantage of using separate imaging probes and therapy probes is that ultrasound imaging probes are relatively ubiquitous, and many medical offices already have access to ultrasound imaging probes and ultrasound imaging systems. Thus, the ability to simply purchase an ultrasound therapy probe to enable image guided HIFU therapy of the nervous system will likely reduce the cost of implementing this new treatment method.

When separate imaging probes and therapy probes are employed, it may be beneficial to utilize a frame or bracket to maintain a desired spatial orientation between the imaging probe and the therapy probe, particularly when the tracking systems described above are not employed. When such a frame is employed, before therapy is initiated, the clinician will verify that the focal point of the therapy probe will lie within the image plane of the imaging probe. This step can either be established geometrically (by understanding the beam geometry of the ultrasound imaging probe and the HIFU therapy probe, and then ensuring that the probes are positioned so that the beams overlap) or empirically. An icon can be added to an ultrasound image generated by the imaging probe to represent the predicted location of the focal point of the HIFU beam. The clinician can then manipulate the position of the combined instruments until the icon overlies the desired treatment point in the ultrasound image. The position of the icon verifies that the focal point of the HIFU transducer will coincide with the desire to treatment site. As discussed in greater detail below, the clinician can then employ one of several additional techniques to verify that the focal point is indeed properly positioned before initiating therapy, if so desired.

Having described a technique for synchronizing HIFU with ultrasound imaging to enable visualization of the focal point of the HIFU beam during therapy, exemplary tracking systems, probes and frames, the following discussion covers the use of HIFU therapy to treat the nervous system. In accord with the present invention, HIFU therapy can be employed to alleviate pain, to provide an anesthetic effect, to treat spasticity, and to provide a cosmetic effect.

HIFU Therapy Applied to the Nervous System

FIG. 6A illustrates an exemplary use of HIFU therapy applied to the nervous system of the patient in accord with the present invention. In a HIFU therapy probe 65, an acoustic coupling 67 is attached to a therapy transducer 68 that is mounted to a handle 70. A lead 72 couples the transducer to a power supply (not shown). In FIG. 6A, probe 65 is being used to apply HIFU to a nerve 82 proximate to a dermal layer 76 of a patient (not otherwise shown). While many different acoustic transducers are suitable for HIFU applications, many HIFU transducers exhibit a generally conical-shaped beam 74, and a substantially smaller, generally elliptical focal region 78. When probe 65 is positioned so that focal region 78 is coincident to nerve 82, and therapy transducer 68 is energized, HIFU therapy of nerve 82 is achieved.

As described in greater detail below, depending on the duration and power levels of HIFU employed, the therapy can result in a partial blockage of nerve function, a complete blockage of nerve function, a relatively temporary blockage of nerve function, or a relatively permanent blockage of nerve function. It should be understood that nerve 82 is intended simply as a schematic representation of an exemplary nerve and is not intended to represent any specific nerve structure. It should also be understood that suitably configured HIFU therapy probes for treating neural structures could be used inside a patient's body (inserted either via a body cavity or incision) and are not limited to external use. The use of an external HIFU therapy probe or a HIFU therapy probe configured for insertion into a body cavity are preferred to inserting HIFU therapy probes into the body via an incision, because the two former techniques are less invasive than the latter technique.

An important component in any type of ultrasound therapy system is the mechanism for coupling the acoustic energy into the tissue. Good acoustic coupling is necessary to efficiently transfer the ultrasound energy from the transducer to the treatment site. The ideal acoustic coupler is a homogenous medium that has low attenuation and acoustic impedance similar to that of the tissue being treated. Due to its desirable acoustic transmission characteristics, water has commonly been used as the coupling medium in many therapeutic applications of ultrasound.

Several different types of acoustic couplings are known. Acoustic viscous coupling gels can be smeared over the distal end of the probe and on the patient's skin (or tissue layer in a body cavity) to facilitate acoustic coupling. Water is an excellent acoustic coupling medium, and water filled sacks or envelopes are often disposed between an acoustic transducer and the skin layer to facilitate acoustic coupling. While the use of aqueous filled membranes is well known, there are some disadvantages to using aqueous filled membranes for acoustic coupling. These disadvantages include a requirement for degassing the aqueous solution (the presence of gas bubbles will significantly impede transmission of the ultrasound waves), sterilization concerns, and containment issues. Hydrogels are solids having a particularly high water content, and are efficient coupling media for diagnostic ultrasound. Hydrogels are hydrophilic, cross-linked, polymer networks that become swollen by absorption of water. The high water content and favorable mechanical properties of hydrogels have made them attractive for a wide range of biomedical applications, including soft contact lenses, maxillofacial reconstruction, burn dressings, and artificial tendons. Since hydrogels consist mostly of water, they inherently have low attenuation and acoustic impedance similar to tissue. They can be formed into rigid shapes and have relatively low material costs. Unlike the ultrasound transmission gels typically used for diagnostic scans, hydrogels can have consistencies similar to soft rubber, and can be formed into relatively rigid, 3D shapes. In one preferred embodiment of the present invention, acoustic coupling 67 is implemented as a hydrogel coupling. It should be understood, however, that acoustic coupling 67 can also be implemented as a viscous ultrasound transmission gel or an aqueous filled membrane.

Acoustic transducer 68 has a fixed focal length. That is, focal region 78 is separated from acoustic transducer 68 by a fixed distance (absent any interactions with matter that would tend to deflect the acoustic waves responsible for focal region 78). Yet, the present invention is not limited to the use of fixed focal length acoustic transducers, and phased arrays of acoustic transducers having variable focal lengths can also be employed. However, a fixed focal length acoustic transducer can be utilized to achieve a robust, relatively simple, and useful HIFU therapy probe. In applications where a fixed focal length acoustic transducer is used for HIFU therapy, acoustic coupling 67 can be used to control the position of focal region 78 relative to the patient. If a relatively thicker acoustic coupling 67 is employed, focal region 78 will be disposed closer to dermal layer 76, while if a relatively thinner acoustic coupling 67 is employed, the focal region will penetrate further below the dermal layer and deeper into the subcutaneous target. Thus, the thickness of acoustic coupling 67 can be used to control the position of the focal region relative to a patient's tissue. As noted above, hydrogels can be formed into relatively rigid, 3D shapes and are relatively inexpensive. Thus, a plurality of hydrogel couplings of different thicknesses can be provided to enable HIFU therapy probe 65 to deliver HIFU to treatment sites disposed at various distances from dermal layer 76. This effect is readily apparent in FIG. 6B, in which an acoustic coupling 67a replaces acoustic coupling 67 of FIG. 6A, and focal region 78 now coincides with a different portion of nerve 82. In FIG. 6B, an ultrasound imaging probe 84 generates an image plane 86. Focal region 78 lies within image plane 86, so that focal region 78 can be visualized in an ultrasound image provided by image ultrasound imaging probe 84 during therapy, using the synchronization method described above.

FIG. 6C schematically illustrates a needle 80 positioned at the nerve to be treated. Such a needle can be used to introduce nerve block agents, such as alcohol, to enhance a conduction block achievable via HIFU therapy alone. In addition to being used to introduce a therapeutic agent into the treatment area, needle 80 can be readily visualized in an ultrasound image and can be used as a reference to facilitate guidance of the HIFU therapy. The needle can also be used to introduce micro-bubbles into the treatment site to induce cavitation, which will tend to increase the efficiency of the HIFU therapy. The introduction of bubbles to the treatment site enhances therapy in a number of ways. First, such micro-bubbles can be readily visualized in the ultrasound image, enhancing the image of the treatment site. Second, such micro-bubbles can be used to lower the cavitation threshold at the treatment site and enable lower HIFU energies to be used to achieve the same therapeutic effect provided by higher energy HIFU. The lower energy HIFU is less likely to introduce undesirable damage to adjacent tissue, which is quite important if sensitive structures are disposed near the neural treatment site.

Also included in FIG. 6C is a blood vessel 253 into which contrast agents 255 have been introduced. Blood vessel 253 is disposed relatively close to nerve 82, and a clinician will want to ensure that the HIFU therapy of nerve 82 does not inadvertently damage blood vessel 253. Introducing ultrasound contrast agents (or MRI contrast agents if MRI is being used to visualize the treatment site) into blood vessel 253 will enable the blood vessel to be more readily visualized, so that the clinician can ensure that the focal point of the HIFU transducer does not impinge on blood vessel 253. Furthermore, by providing real-time and ultrasound guided HIFU therapy, the clinician can monitor the ultrasound image of the treatment site during therapy, and if any lesion induced by the HIFU therapy begins to expand undesirably close to blood vessel 253, the clinician can terminate the therapy.

FIG. 7 shows a flowchart 390 that indicates a sequence of logical steps to perform HIFU therapy on the nervous system. As noted above, such therapy can be used to treat spasticity, to alleviate pain, to achieve an anesthetic effect, or achieve a cosmetic effect. The steps indicated in FIG. 7 can be used for any of these purposes. In a block 392, a treatment site associated with the nervous system is selected, while in a block 394, a specific dose is selected. The particular treatment site will be a function of the type of therapy being implemented. If the therapy is to alleviate pain, then a nerve or nerve ganglia involved in the conduction of pain signals will be selected. Those of ordinary skill in the art will readily recognize that the step of choosing an appropriate treatment site must be carried out very carefully. Preferably, the treatment site selected will maximize a beneficial therapeutic effect, while minimizing any undesired effects. For example, assume that the HIFU therapy is intended to alleviate pain in an extremity (such as a hand). Many different nerves are involved in the conduction of sensory signals from the arm to the brain, and any of those nerves can be used to interrupt the pain signals from the hand. Selecting a nerve close to the brain will likely result in interrupting the transmission of signals in the nervous system that are unrelated to the pain sensation being transmitted from this extremity. Selecting a nerve very close to the site where the pain signals originate will still block the conduction of pain signals from the extremity to the brain, but will be much less likely to interfere with the transmission of other sensory signals. The determination of an appropriate dose will preferably be based on empirical studies, much in the way that pharmacological doses are selected. Thus, selection of a treatment site and dose will be based not only on a thorough knowledge of anatomy and the nervous system, but also on empirical studies that substantiate that the proposed treatment will achieve the desired therapeutic effect.

In a block 395, the therapy probe is positioned such that the focal region (or focal point) of the therapy transducer is incident on the treatment site selected. Determining where the therapy probe should be positioned will be a function of the anatomical position of the nerve and the focal length of the therapy transducer. Verification of the anatomical position of the treatment site can be carried out in a pre-therapy exam using imaging technologies such as ultrasound or MRI. Based on the identified location of the treatment site, and the known focal length of the therapy transducer, an optimal position for the therapy probe can be fairly accurately established. In a block 396, the accuracy of the positioning of the therapy probe relative to the treatment site (and more importantly, the position of the focal point relative to the treatment site) is evaluated to verify that the therapy probe is properly positioned. As described in detail below, several different techniques can be used to verify that the therapy probe, and the focal point of the therapy transducer, are properly positioned relative to the treatment site. Once the proper positioning of the therapy probe has been verified, in a block 398, the therapy transducer is energized using the dose information determined in block 394, to provide HIFU therapy to the nervous system. In a decision block 400, the treatment site and/or patient are evaluated to determine whether the desired therapeutic effect has been achieved. Such an evaluation preferably includes imaging the treatment site during therapy using ultrasound (to achieve real-time image guided therapy). Or this evaluation may alternatively be based on MRI imaging of the treatment site, which as noted above, incurs a latency problem. As discussed in detail above, real-time image guided therapy is preferred, because the clinician may monitor the treatment site in real-time and halt the therapy if the thermal and mechanical effects (such as lesion formation) extend beyond the identified treatment site. Thus, real-time image guided therapy provides the clinician the assurance that therapy can be halted if the therapeutic effect desired begins to extend beyond the selected treatment site. Empirical studies establishing a dose response for HIFU as applied to the nervous system will provide a margin of safety, however real-time image guiding of HIFU therapy will provide an additional measure of safety.

Such an evaluation may also be based on monitoring the patient's physiological responses. For example, if HIFU therapy is being used to alleviate pain, the patient can be questioned to determine if the level of pain has decreased. If HIFU therapy is being used to control spasticity, the patient can be monitored for a period of time after the therapy to determine if the spasticity has decreased. If HIFU therapy is being used to provide an anesthetic effect, the patient can be queried to determine if any anesthetic effect has been achieved, and if so, if such an effect has reached the desired intensity. If HIFU therapy is being used as an alternative to Botox therapy to achieve a cosmetic effect (i.e., a temporary paralysis of nerves controlling facial muscles to reduce wrinkles and simulate a more youthful appearance), the effect of the therapy on the patient's cosmetic appearance can be evaluated. If it is determined that the therapy has successfully achieved the desired result, then in a block 402, the therapy probe is removed. If it is determined that the desired therapeutic effect has not yet been achieved, additional therapy can be provided.

As noted in the details of block 396 (shown in FIG. 7), several different techniques can be used to verify that the focal point of the HIFU transducer coincides with the selected treatment site in the nervous system. In a block 396a, a combination of imaging and HIFU beam geometry are used to verify that the focal point properly coincides with the selected treatment site. As indicated above, the focal length of a HIFU transducer is a well-defined parameter. Referring now to FIG. 6B, if the relative positions of therapy probe 65 and imaging probe 84 are known, the relative position of focal region 78 within imaging plane 86 can be determined. An icon can be introduced into the ultrasound image provided by imaging probe 84 to indicate the anticipated position of focal region 78 (based on the relative positions of the therapy probe in the imaging probe, and the known characteristics of the focal length). If the ultrasound image from imaging probe 84 indicates that focal region 78 does not properly coincide with the selected treatment site, therapy probe 65 and imaging probe 84 can be moved in concert until the icon corresponding to the predicted position of the focal region properly coincides with the selected treatment site. If the therapy transducer and imaging transducer are implemented as a single probe, any movement of the imaging transducer will result in a corresponding movement of the therapy transducer. If the imaging transducer and the therapy transducer are implemented as separate instruments, care must be taken so that any movement of the imaging probe is matched by a corresponding movement of the therapy probe (unless a sophisticated tracking system such as those described above is used to independently track and display the positions of each probe). This result can be achieved by using a frame to couple the imaging probe to the therapy probe. In this event, any movement of the imaging probe used to ensure that the icon representing the focal region of the HIFU transducer coincides with the desired treatment site will result in a corresponding motion of the therapy probe. While this technique has been specifically described as using ultrasound imaging, those of ordinary skill in the art will readily recognize that MRI could be used in place of ultrasound imaging to achieve the same result.

Yet another technique for verifying that the focal point of the HIFU transducer coincides with the selected treatment site involves the use of relatively low power HIFU combined with imaging, as indicated in a block 396b. As noted above, even a relatively low power HIFU wave will change the echogenicity of the target at the focal point of the HIFU transducer. This change in echogenicity can be identified using imaging ultrasound. Thus, in this technique, the HIFU transducer is energized at a power setting selected to change the echogenicity of the treatment area at the focal point as well as minimize any therapeutic effects, so that if the focal point is not correctly aligned, minimal undesirable effects on non-target tissue will occur. Empirical studies have indicated that relatively low levels of HIFU will change the echogenicity of the treatment site without any other appreciable effects on non-targeted tissue (i.e., no tissue necrosis or noticeable damage). This change in echogenicity persists briefly, so that the change can be detected by using imaging ultrasound after a relatively short burst of low power HIFU has been delivered. Alternatively, the synchronization techniques described above can be used in real-time to visualize the treatment site as the low level HIFU is being delivered. Regardless of the approach used, the change in echogenicity in the ultrasound image is identified to determine whether the therapy probe is properly positioned so that the focal region coincides with the selected treatment site. If not, the therapy probe is repositioned, and an additional verification step is performed, until the change in echogenicity induced by the relatively low power HIFU burst coincides with the desired treatment site. This verification technique can be used in connection with a frame, thereby ensuring that the spatial orientation between the imaging probe in the therapy probe remained fixed, or this technique can be used in freehand registration of the probes without requiring a sophisticated tracking system, as described above.

Still another technique to verify that the therapy probe is properly positioned so that the focal region of the therapy transducer coincides with the selected treatment site is based on applying a relatively short burst of HIFU and monitoring the patient's physiological reaction, as indicated in a block 396c. Depending on the nerve or other portion of the nervous system that is being targeted, a specific and well-defined physiological reaction may result based on delivering HIFU therapy to the treatment site. An analogy to this technique would be the well-known knee-jerk response a physician can induce in a patient by lightly striking the patient's knee in a particular anatomical location. Where such well-defined physiological responses to the application of HIFU exist and are empirically identified, they can be used to verify that the focal region of the therapy transducer is probably positioned relative to the treatment site. Because this technique does not provide actual visual verification (via medical imaging) that the focal region of the HIFU transducer actually coincides with the desired treatment site, this technique is likely to be better suited to providing relatively lower doses of HIFU therapy that do not result in permanent effects. As discussed in greater detail below, empirical evidence indicates that a well-defined dose response between a level of HIFU therapy applied and an induced therapeutic effect on the nervous system can be identified. Empirical evidence indicates that based on the dose, the therapeutic effect can be temporary (i.e., a non-permanent interruption of nerve conduction) or permanent. When this verification technique is used in combination with the relatively lower doses of HIFU that enable non-permanent therapeutic effects to be achieved, if the expected physiological response is indicated even when the desired treatment site has not been accurately targeted, there is little danger that an undesirable permanent effect will result.

Yet another method to determine if HIFU therapy of the nervous system has been successful is to measure the physiological response of the treated neural structure to electrical simulation, to determine if conduction of neural impulses through that neural structure have been blocked. A blockage indicates successful treatment.

HIFU Therapy and Dose Response

For each potential clinical application of HIFU, the biological effects on the specific tissue of interest must be determined in order to achieve the desired clinical outcome. Different parameters of HIFU can result in variable effects on the tissue, such as a peripheral nerve. To enable the use of HIFU to produce effects on the nerve, ranging from partial conduction block to irreversible axonal degeneration (to treat a range of severities of spasticity), HIFU parameters can be appropriately varied to achieve these effects. HIFU application to a specific structure within the body (i.e., to a tumor or nerve) can be described using the standard treatment parameter of "dose." In this paradigm, the HIFU dose is quantified in a similar way as in other forms of medical treatment involving applying energy to tissue, i.e., as the intensity $I$ ($W/cm^2$) multiplied by the duration $t$ (s) of the exposure (Dose=$I \times t$) in units of $J/cm^2$. Dose is an important parameter in the production of biological effects during HIFU treatment. Furthermore, different tissues in the body absorb acoustic energy at different rates (different absorption coefficients) and thus, the same HIFU dose may result in different biological effects when applied to a range of tissue types. It is therefore important to investigate the dose-dependence of the specific tissue (i.e., neural structures) of interest, varying both intensity and duration, in order to develop the most optimal treatment plans to produce the desired biological effects.

It is believed that manipulating the HIFU dose will achieve a graded effect on the nerve and the suppression of its function. Higher intensities, resulting in lesion formation of an entire nerve fiber or bundle, will completely block the nerve conduction for the nerve or bundle, much as a surgical separation of the nerve would. Intermediate intensities, damaging less of the nerve structure, will cause less (or reversible) suppression of nerve function. Either dose response has clinical application. A permanent nerve block would provide an effect essentially like severing the nerve, such that the spasticity or pain associated with a specific nerve would be prevented indefinitely. Any voluntary function provided by this nerve would also be eliminated. Therefore, this effect would be useful primarily for patients who no longer have voluntary function, such as those with a complete transection of the spinal cord, yet having spasticity and/or pain. Where empirical dose studies indicate levels of HIFU with reversible effects, such dose could be employed to treat spasticity or pain without hindering the voluntary function of a patient. Particularly with respect to achieving an anesthetic effect or a cosmetic effect, the empirical identification of HIFU doses resulting in reversible effects for particular neural structures is required.

Empirical Studies

A series of in vivo studies have been completed that support the conclusion that HIFU can provide a range of effects on peripheral nerves that appear to be controllably variable from a partial conduction block, to a complete conduction block (acute effects), and from a reversible block, to irreversible axonal degeneration (chronic effects). The initial work focused on developing an ultrasound image-guided HIFU system and a HIFU protocol to completely suppress the function of the sciatic nerve complex of rabbits. Investigation of the long-term effects of such complete blocks has also begun, indicating axonal degeneration as a chronic effect of HIFU treatment. Furthermore, initial results of acute studies using rabbit and pig femoral nerves have indicated the likelihood of partial conduction block as an acute effect of HIFU treatment with variable exposure parameters.

$1^{st}$ Study: Complete Conduction Block of the Rabbit Sciatic Nerve Complex

One empirical study used ultrasound image-guided HIFU to target and suppress the function of the sciatic nerve complex of rabbits in vivo. The results of this study support the conclusion that ultrasound image guided HIFU can be used to locate, target, and treat peripheral nerves to treat severe spasticity. Such a technique will provide a non-pharmacological, non-invasive alternative to surgical severing of nerves.

FIG. 8A is a photograph of the system employed, which included an ultrasound imaging transducer 84a (CL10-5, Philips HDI-1000™, Philips Ultrasound, Bothell, Wash.) and a HIFU transducer 68a (SU-107™, Sonic Concepts, Woodinville, Wash.), each transducer being coupled to a custom frame 88 to ensure that the geometrical orientations of the two beam patterns were coplanar, enabling a HIFU focus 78a of HIFU beam 74a to be visualized in an image plane 86a. Note that frame 88 includes adjustments along the x and z axis, as well as an angular adjustment, as respectively indicated by arrows x, z, and θ. The compact linear array imaging transducer employed has a broadband frequency of 5-10 MHz. The 3.2 MHz single-element HIFU transducer has a focal length of 3.5 cm. Specially molded polyacrylamide based hydrogels (not shown in FIG. 8A, but see FIGS. 6A and 6B) were employed to provide efficient coupling of the HIFU energy into tissue, enabling transmission of the HIFU beam to its focal zone and formation of a lesion encompassing the nerve. The gel standoffs also enabled proper positioning of the HIFU focus at the depth of the sciatic nerve, as described above in connection with FIGS. 6A and 6B.

The HIFU transducer and imaging transducer were synchronized as discussed above, to enable the visualization of the HIFU focus within the ultrasound image. The synchronization enabled the HIFU focal region to be seen in the window between the interference bands created by the overlapping on-time of the HIFU and the imaging. This method of synchronization enables the precise visualization of the HIFU focus as it formed a hyperechoic region in the ultrasound image. Once the HIFU and imaging transducers were secured to the frame, a tissue-mimicking phantom was used to determine where the focus appeared in an ultrasound image generated with the imaging transducer. As indicated in FIG. 8B, an icon 89 was marked on a transparent sheet 87 overlaying an ultrasound image 85, for use as a reference for later imaging, where icon 89 corresponds to the HIFU focus. As long as the relative positions of the HIFU transducer and imaging transducer are not changed (i.e., the ultrasound imaging transducer end of the HIFU transducer remain coupled to the frame), transparent sheet 87 can be used to identify the position of the HIFU focus before the HIFU transducer is energized by placing the transparent sheet (including the icon) over an image of the target area obtained using the ultrasound imaging transducer. In more sophisticated systems, this icon could be generated electronically in the ultrasound image (or other image, see FIG. 5C and the related text).

FIG. 8C schematically illustrates HIFU transducer 68a, and imaging transducer 84a secured to frame 88 and disposed adjacent to a gel phantom 91. The HIFU transducer is energized to generate a lesion 93 in the gel phantom. Generally elliptical icon 89 is added to a transparent sheet as discussed above. FIG. 8D is a photograph of ultrasound image 95, including a lesion 99 and interference bands 97. Ultrasound image 95 was generated after moving frame 88 (with the therapy and imaging transducers in their same relative positions) to a treatment subject (a rabbit as described below) and obtaining a pre-therapy ultrasound image. The overlay sheet including icon 89 (described in connection with FIG. 8B) was then placed over the pre-therapy ultrasound image, and the position of the frame (and the therapy and imaging transducers attached to the frame) was manipulated until icon 89 coincided with the desired treatment location. HIFU transducer 68a was energized during real-time imaging (note interference bands 97), and lesion 99 was generated in the location indicated by the icon verifying that the use of a gel phantom, an icon, and a frame enable accurate prediction of the focal region of the HIFU beam.

In the first empirical study, eleven New Zealand white rabbits were anesthetized and the sciatic nerve complexes of both legs were treated with HIFU. Each animal was oriented on a surgical table 107 as schematically indicated in FIG. 9A, such that its leg 103 was stabilized and perpendicularly coupled to a tension force gauge 105 (FGV-2A™ from Shimpo, in Itasca, Ill.). The proper orientation was achieved by placing the animal on its side with the top leg supported by the weight of custom-designed polycarbonate surgical table 107. The custom-designed surgical table included a plurality of holes 113 to enable the strain gauge to be selectively positionable. Pins (not separately shown) could be inserted into these holes to secure the strain gauge, thereby rigidly attaching the force gauge to the table to prevent movement during the experiment. A strap 111 was tied around the foot of the rabbit at the metatarsal joint and connected directly to the force gauge. A 3 cm incision was then made in the skin transversely across the leg at the mid-thigh level. The skin was pulled back to expose the lateral hamstring muscle. For this terminal study, HIFU was applied through a polyacrylamide gel coupler, directly to the surface of the lateral hamstring muscle (with the nerve complex positioned under the muscle layer) in order to eliminate the problems that can occur when HIFU must transmit through the skin. The primary goal of this empirical study was to couple the high energy beam into the muscle tissue such that the beam would focus at a treatment site 119 in sciatic nerve complex 82a, as indicated in FIG. 9B. Effective coupling is achieved by minimizing the impedance mismatch between the ultrasound transducer, gel coupler, and the skin. The formation of air pockets between the gel coupler and the skin can result in a significant impedance mismatch. The reflection of the high energy beam at this air interface would direct much of the energy on the skin, leading to burns. Rabbits have a very fine layer of hair covering their legs, which is difficult to remove completely, and any remaining hair can result in air pockets between the coupling medium and the skin. This issue is not present in humans, and much better HIFU coupling can be achieved with human skin. Later rabbit studies achieved adequate skin preparation, and successfully transmitted HIFU through the rabbit skin to provide a non-invasive treatment of the nerve.

As schematically shown in FIG. 9B, the tip of an anodal stimulating electrode 115 (Teflon-coated except for the exposed tip; Teca, DMG50™, Oxford Instruments Medical Inc., Hawthorne, N.Y.) was inserted subcutaneously near the hip bone, and a similar cathodal stimulating electrode 117 was positioned near the nerve just below the sciatic notch, via sequential repositioning as electrical stimulation intensity through the tip of the needle was reduced. The settings of the electrical stimulator (Model S88™, Grass Telefactor and, West Warwick, R.I.) included 1 pulse/s with 50 ms duration and an initial voltage of 15 V. The force response of the plantarflexion muscles in the rabbit foot to this electrical stimulus was measured with the force gauge. The voltage of the electrical stimulus was lowered to assure that the baseline muscle response was still strong, even at voltages below 5 V. Once a strong baseline force response was observed (approximately 0.55 N), the electrodes were removed so that HIFU treatment could begin.

The image-guided HIFU device of FIG. 8A was placed on the surface of the lateral hamstring muscle (with a layer of ultrasonic coupling gel between the HIFU probe and the muscle) and oriented so that the sciatic nerve complex, which was under the muscle, could be viewed transversely in the ultrasound image, as is schematically indicated in FIG. 9C. A gel coupler 67b was attached to HIFU transducer 68a. Gel coupler 67b was selected to have a thickness such that the HIFU could be targeted into the muscle just below the nerve (as indicated by the position of the focus marked on the overlying transparent sheet, as described in connection with FIG. 8B). The nerve complex was again located in the ultrasound image (through visualization of the cross section of the complex as a hyperechoic structure between the muscles of the leg), and the treatment plan was confirmed. HIFU was targeted initially at a point 121 in the muscle tissue immediately adjacent to the nerve, and treatment was applied such that the lesion progressed upward (towards the transducer) through the nerve and into the upper muscle, as indicated by a point 123. An arrow 127 indicates the direction of scanning. The acoustic output of the transducer for all experiments was 60 W at a duty cycle of 55%, and an acoustic intensity of 1480-1850 W/cm2 (ISATA, spatial-average, temporal-average). A scanning rate of HIFU application (0.5-0.6 mm/s) was used to ensure that the entire nerve complex was treated (the nerve complex was 3-4 times larger than the HIFU focal region). HIFU treatment continued until the HIFU focus had been scanned across the entire nerve complex, as evidenced by the progression of the hyperechoic spot in the image (note the cylindrical shape formed by scanning the generally elliptical focal region). The nerve was again stimulated using the near-nerve electrodes by positioning the electrodes proximal to the HIFU treatment site. If any force response remained, the nerve was retreated with HIFU. The experiment was complete when no force response remained. A successful block was indicated by no force response to stimulation of the nerve proximal to the HIFU site, yet a strong force response, approximately 0.55 N, to stimulation (at voltages less than 5 V) of the nerve distal to the HIFU site. FIG. 9D is substantially similar to FIG. 9C, and shows the scanning motion from another perspective, with knee 125 being visible in FIG. 9D.

FIG. 9E is a photograph of the above-described procedure. An incision 129 has been made in rabbit leg 103, and frame 88, HIFU transducer 68a, and imaging transducer 84a (not visible in FIG. 9E) are positioned adjacent the incision, such that a gel coupling 67b contacts the muscle tissue to acoustically couple the HIFU transducer to the muscle tissue.

After euthanization, segments of the sciatic nerve complex (~1 cm length) at the HIFU treatment site, as well as 2 cm proximal and distal to the site, were taken for histology. Tissue samples from six animals were fixed in formalin for light microscopy and samples from three animals were fixed in 3% glutaraldehyde for transmission electron microscopy (TEM); time from HIFU treatment to nerve fixation was 30 to 60 min.

Because the rabbit sciatic nerve complex runs loosely between two muscles of the leg, any movement of the muscle layers (needed for immediate observation of the HIFU lesion encompassing the nerve) could disrupt the morphology of the nerve and the adjacent tissue. To enable measurement of the volumes of the lesions, the legs of two animals (four legs) were frozen upon sacrifice to keep the tissue morphology intact. On the following day, the legs were cut in thin slices (2-5 mm) to expose the cross-sectional views of the lesions formed by HIFU treatment. Images of each slice of the lesions were taken using a digital camera (Canon USA Inc., Lake Success, N.Y.) and their areas were determined using the image analysis software ImageJ™ (NIH, Bethesda, Md.). The approximate volumes of the lesions were estimated by adding the volumes of each slice.

The nerve samples fixed in formalin were embedded in paraffin, cut in either cross section or longitudinally with respect to the axons, stained with hematoxylin and eosin (to observe nuclei of Schwann cells) or Masson's trichrome (to observe myelin layers), and observed with a light microscope (DMLS, Leica Microsystems Inc., Bannockburn, Ill.). The samples fixed in 3% glutaraldehyde were cut in cross section into 2 mm pieces, stained with 1% osmium tetroxide and 1% uranyl acetate, dehydrated with a series of increasing concentrations of ethanol, and embedded in plastic (3:2 ratio of Spurr's epoxy: propylene oxide). The samples were cut in semi-thin sections (1 μm), post stained with Richard's stain (methylene blue/azure II), to observe myelin and axon organization, and observed with a light microscope (Leica DMLS). Samples were then cut in thin sections (~100 nm) and observed with a transmission electron microscope (EM 420T) operating at 120 kV.

Beam profiles of the acoustic pressure field of the 3.2-MHz HIFU transducer in both the axial and lateral dimensions were obtained as indicated in FIGS. 10A and 10B, which represent maps of pressure fields associated with HIFU transducer 68a. The grey-scale on the maps represents the dB difference from the maximum measured pressure amplitude. The map of FIG. 10A represents an axial cross section of the beam path where the full-width, half-maximum (FWHM) boundary denotes the focal region of the transducer. Focal dimension in the axial direction is 5.1 mm. FIG. 10B corresponds to a lateral cross section of the beam path at the HIFU focus. The FWHM boundary indicates that the lateral focal dimension is 0.76 mm. Thus, the focal dimensions of the HIFU beam, specified as the axial and lateral (FWHM) dimensions of the pressure field were measured to be 5.1 mm and 0.76 mm, respectively. Therefore, the area of a lateral cross section of the HIFU beam directly at the focus was calculated to be 0.0045 cm2. This area was the spatial area of the beam that had approximately the same pressure distribution and would also correspond to the area of tissue that would receive the same energy distribution with HIFU application. In addition, this area was much smaller than the cross-sectional area of the rabbit sciatic nerve complex, and thus, scanning was required to treat the entire cross-sectional area of the nerve complex. There is a linear relationship between acoustic power and electrical power for the HIFU transducer, and the efficiency of the transducer (conversion of electrical to acoustic power) was measured to be 85%. For the 60 W of acoustic power and the 55% duty cycle used in the in vivo studies, and taking into account the attenuation through the gel coupler (having an attenuation coefficient of about 0.6 dB/cm) and the rabbit muscle (having an attenuation coefficient of about 2.5 dB/cm), the intensity at the focus was determined to be about 1480-1850 W/cm2, dependent upon the depth of the nerve into the leg (nominally 2-2.5 cm) and the thickness of the corresponding gel coupler (nominally 1-1.5 cm). Such intensities have been shown to produce coagulative necrosis in tissue within 1 second of HIFU application. The temperature at the face of the transducer, with HIFU of 60 W acoustic power at 55% duty cycle and duration of 40 seconds, increased from a baseline of 21.3° C. to 35.9° C. The temperature returned to baseline 10 minutes after treatment ceased. The electrical powers (forward and reflected) varied within only 1 W as temperatures were increased.

Successful targeting and conduction block was achieved in 100% of the 22 nerve complexes of the 11 rabbits treated. The duration of HIFU to achieve complete conduction block was 36±14 seconds (mean±SD). High-resolution ultrasound (CL10-5) provided visualization of the sciatic nerve complex and guidance to target the HIFU treatment. The treatment of the nerve was monitored using ultrasound imaging, as shown in FIGS. 11A-11D. The nerve complex was imaged in cross section and observed as a round hyperechoic structure between the two major muscles of the leg as indicated in the ultrasound image of FIG. 11A. The HIFU focus was targeted just below the nerve for the initiation of the treatment is indicated by the ultrasound image of FIG. 11B. As the device was scanned across the nerve complex, the lesion formation was visualized by the progression of the hyperechoic region in the image as indicated by the ultrasound image of FIG. 11C. After HIFU treatment had been completed, the lesion remained visible in the image for several minutes, as indicated by the ultrasound image of FIG. 11D.

Figure 11C:
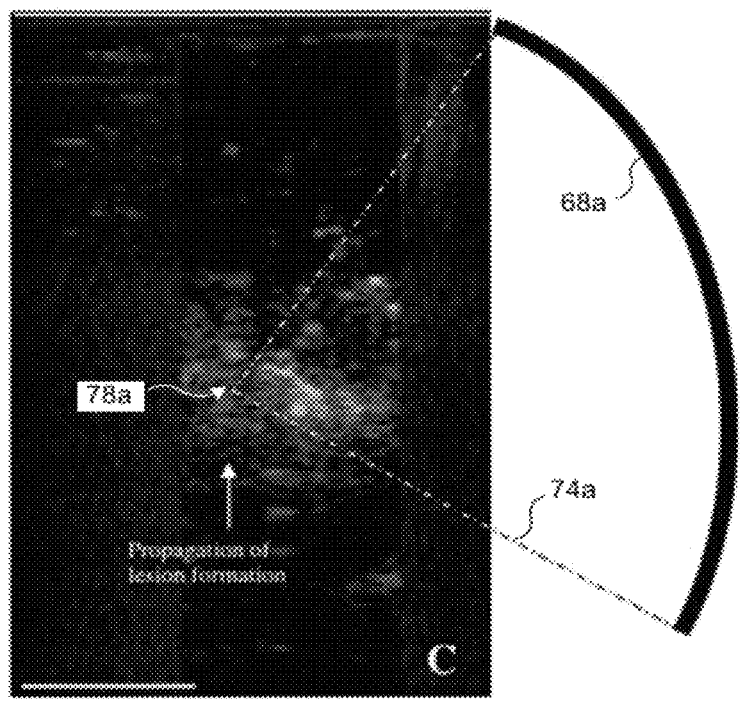
Figure 11D:
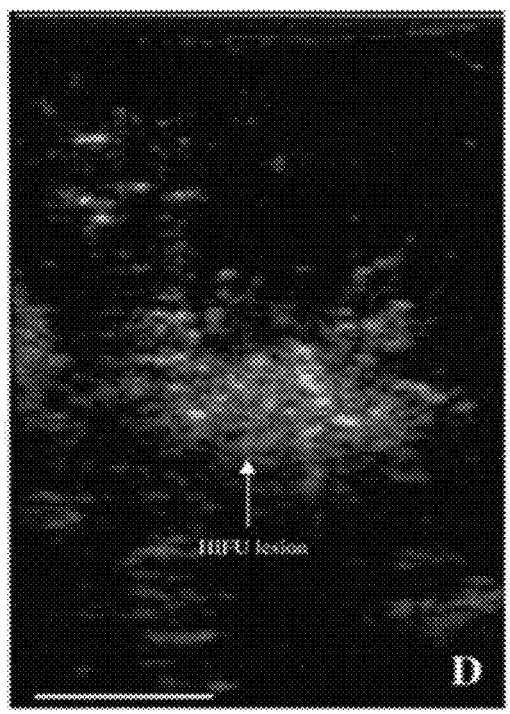

FIGS. 11E-11H are ultrasound images of the rabbit sciatic nerve complex taken in the first study before, during, and after HIFU treatment. These are the same ultrasound images as shown in FIGS. 11A-11D, without the introduction of the HIFU transducer into the ultrasound image and are presented together on one drawing sheet for easy comparison. The ultrasound image of FIG. 11E shows nerve complex 82a, the adjoining muscle tissue, and points 121 and 123 where the HIFU therapy is to begin and end, respectively (to ensure that the entire cross-sectional area of the nerve is treated, the focal region of the HIFU being substantially smaller than the cross-sectional area of the nerve). The ultrasound image of FIG. 11F shows synchronized HIFU interference bands 97, nerve complex 82a, and lesion 99a after two seconds of HIFU therapy. The ultrasound image of FIG. 11G shows synchronized HIFU interference bands 97, nerve complex 82a, and lesion 99a after ten seconds of HIFU therapy. The ultrasound image of FIG. 11H shows the nerve, muscles, and lesion after HIFU therapy.

Figure 12A:
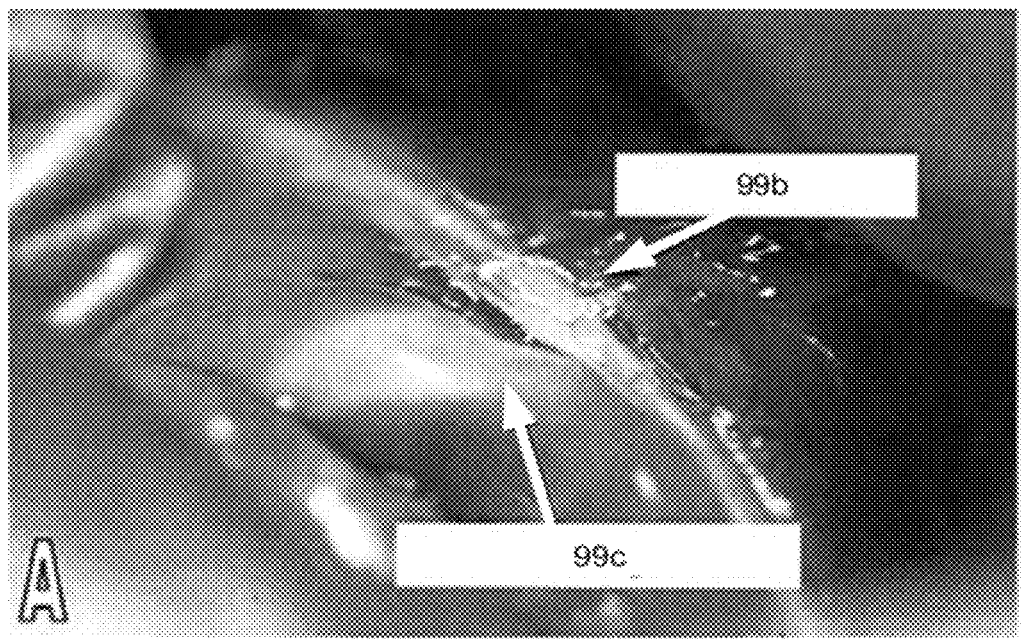
Figure 12B:
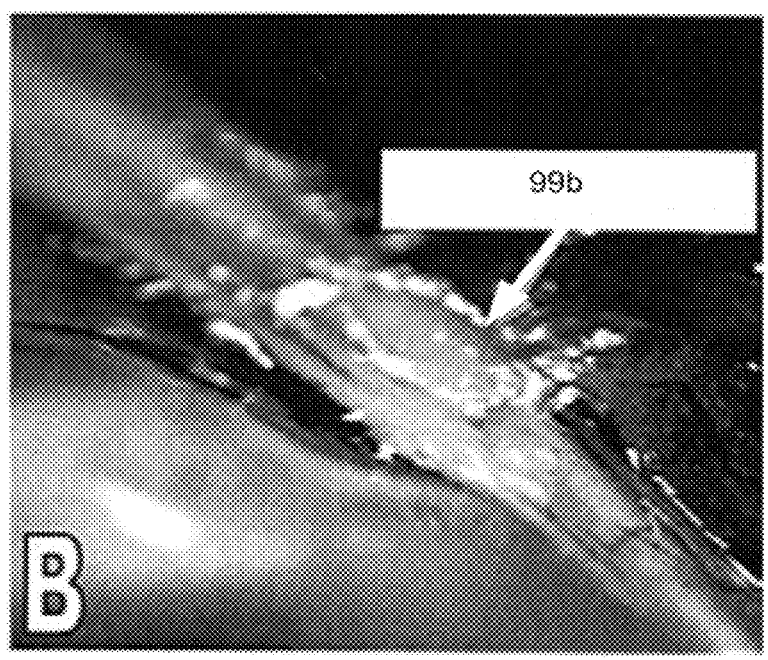
Figure 12C:
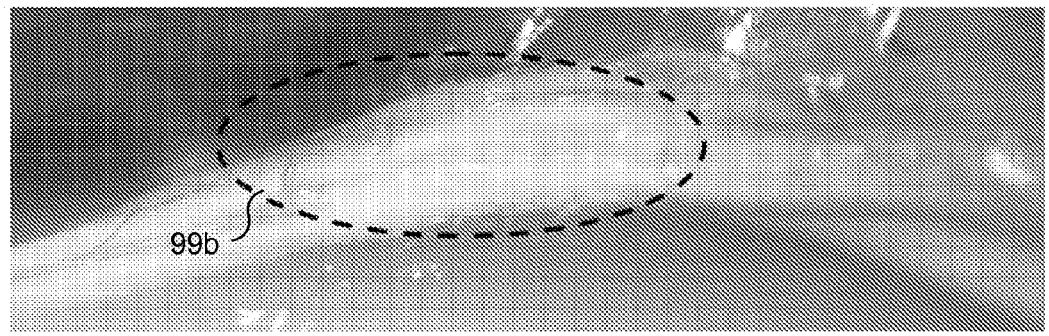
Figure 12D:
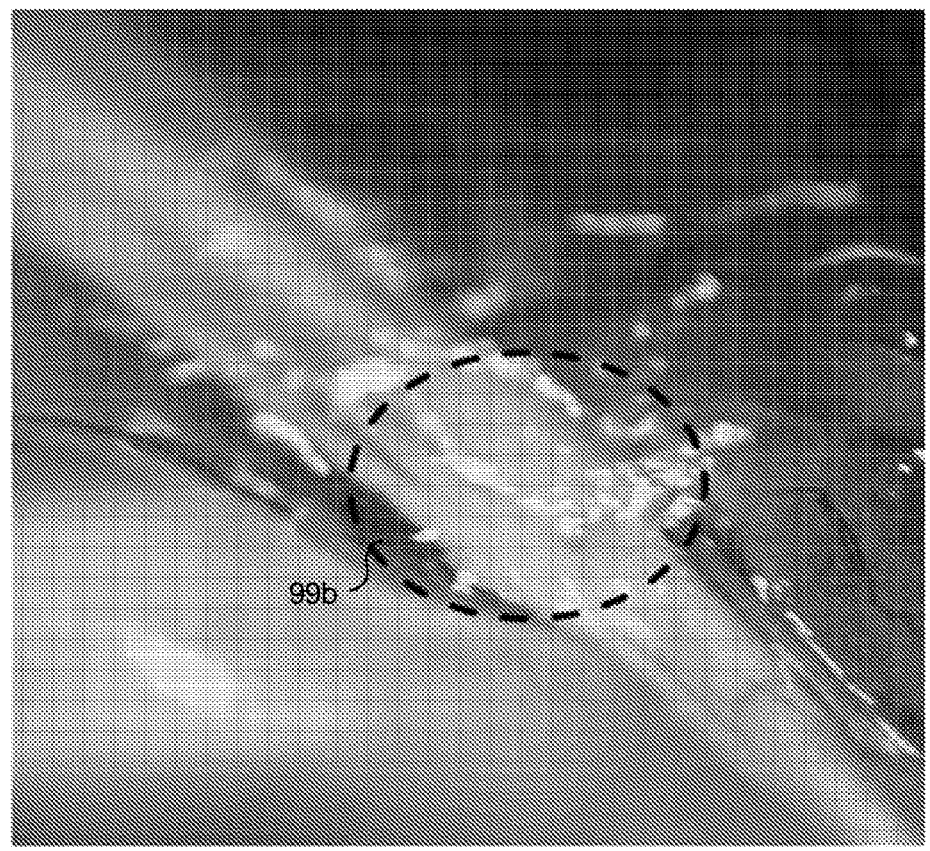
Figure 12E:
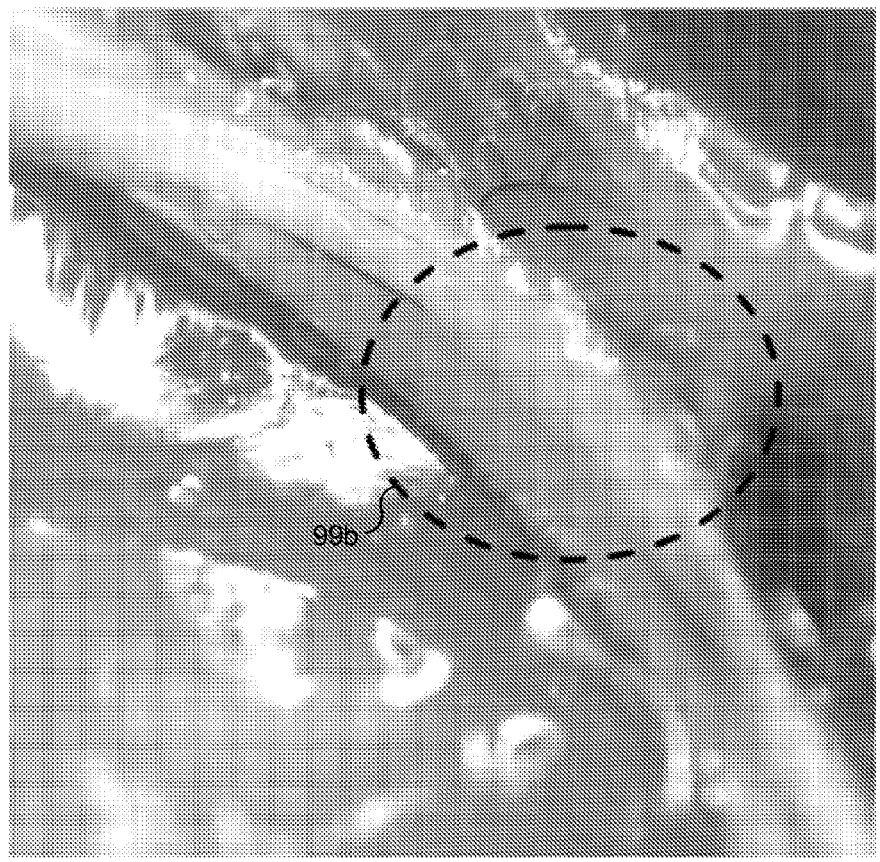
Figure 12F:
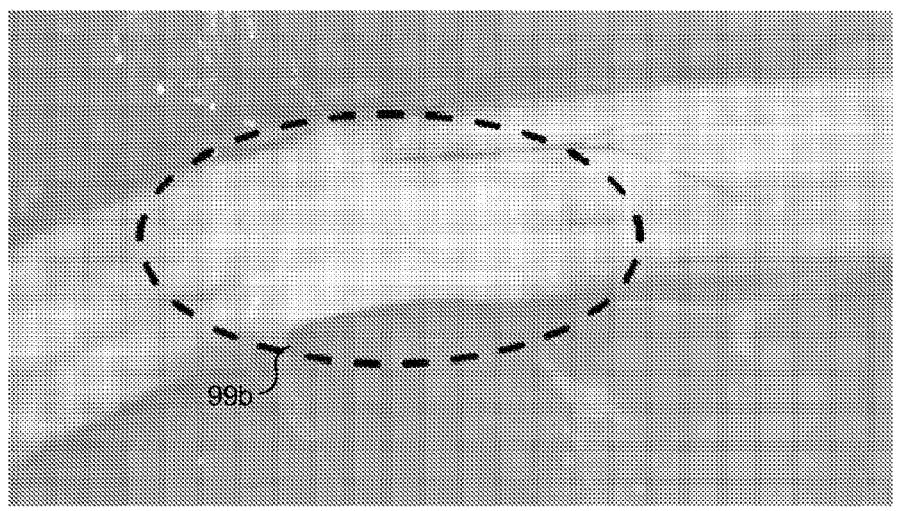

Conduction block was indicated by complete suppression of the force response to electrical stimulation of the nerves. Surgical exposure of the nerves showed a clear presence of HIFU lesions on each sciatic nerve complex, as indicated in the photographs of FIGS. 12A and 12B (the photograph of FIG. 12B is simply a higher magnification image of the photograph of FIG. 12A). The lesions appeared white in comparison to the normal pink color of the tissue. Both a nerve lesion 99b and a muscle lesion 99c are visible in FIG. 12A (as described above, the focal region of the HIFU transducer was swept across the nerve, with an initial focal point coinciding with muscle tissue immediately adjacent to one side of the nerve, and ending in muscle tissue immediately adjacent to an opposite side of the nerve). FIGS. 12C-12F are additional images of ultrasound image guided HIFU induced nerve lesions generated in the first study. Conduction block of all nerve complexes that were surgically exposed was confirmed by observing a complete absence of force response to nerve stimulation proximal to the HIFU site, but a strong force response (approximately 0.55 N) to stimulation distal to the HIFU site.

Thin slicing of the frozen rabbit legs exposed lesions that completely encompassed the nerves. A cross-sectional image of one lesion is presented in FIG. 13. The estimated volumes of the lesions were determined to be 2.8+1.4 cm3 (mean+SD). Such large lesions indicate significant collateral damage to the adjacent muscle which is undesirable for a clinical treatment. By decreasing the time of HIFU treatment, in preparation for the long-term study (discussed below), it is possible to reduce the damage to adjacent tissue.

Figure 14A:
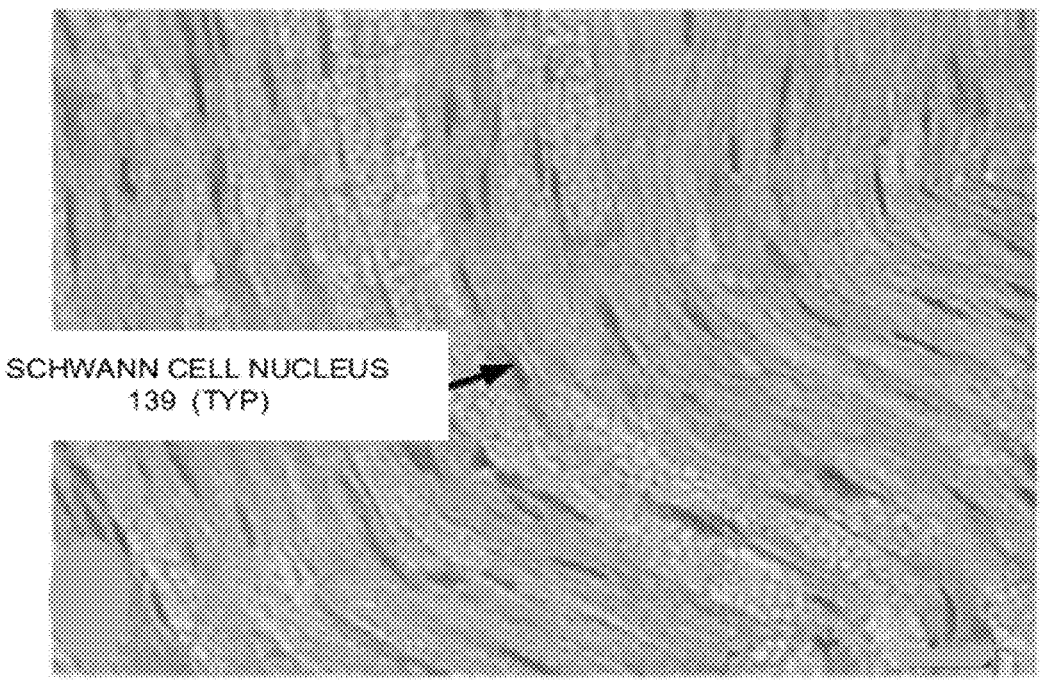
Figure 14B:
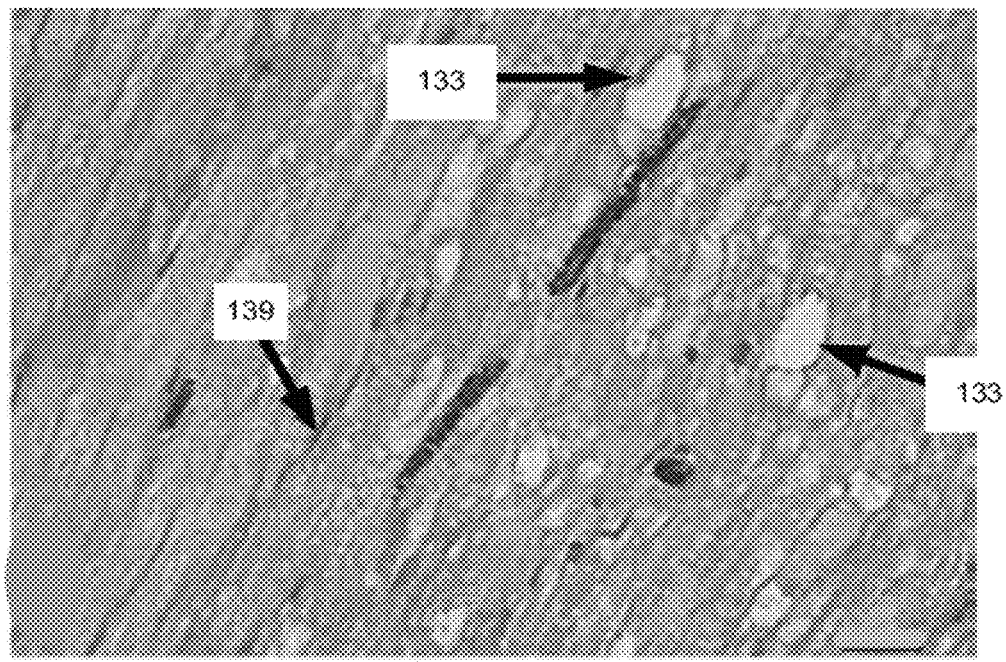
Figure 14C:
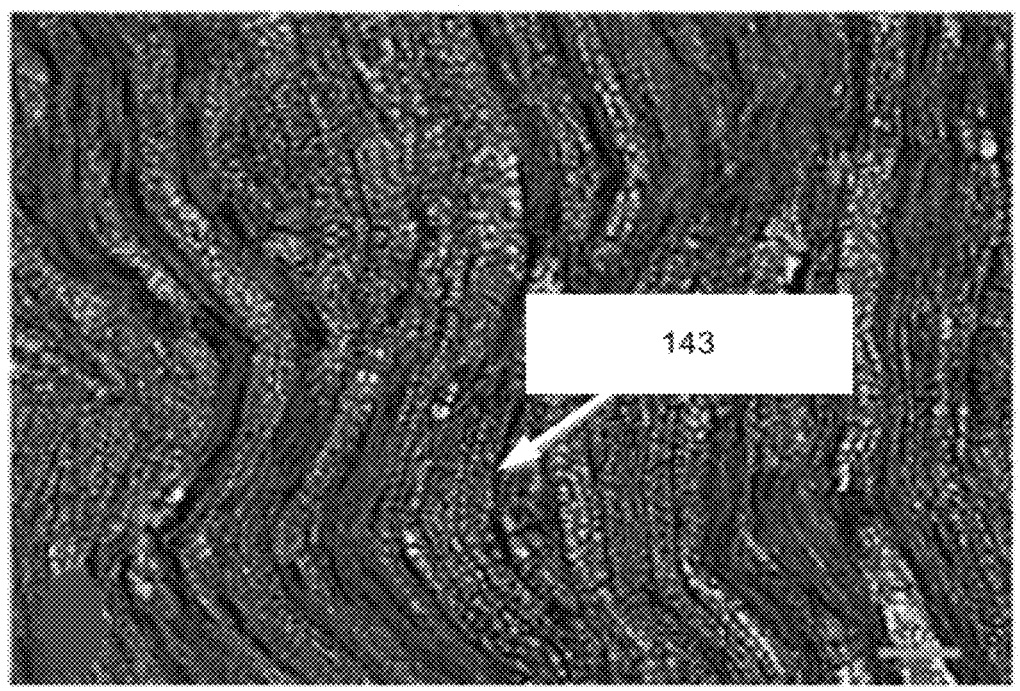
Figure 14D:
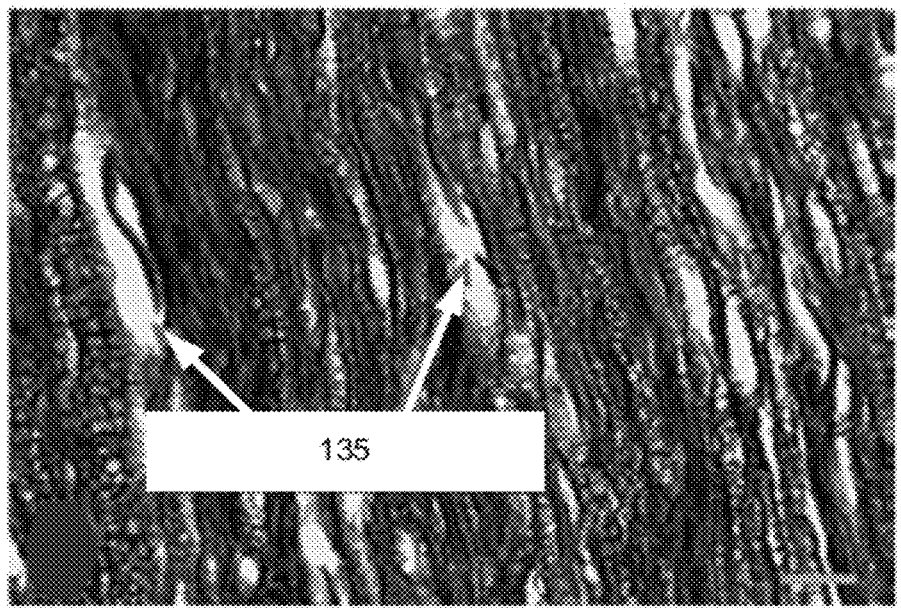

FIGS. 14A-14D are light microscopy images of nerves, stained with H & E (FIGS. 14A and 14B) or Masson's trichrome (FIGS. 14C and 14D), and observed longitudinally. All scale bars equal 20 μm. In FIG. 14A, the untreated section of nerve shows many nuclei of Schwann cells. In FIG. 14B, the HIFU-treated section of nerve appears disorganized. Thick arrows 133 show holes in the structure of the nerve and there are few Schwann cell nuclei 139 present. In FIG. 14C, which represents an untreated section of nerve, arrow 143 shows the untreated nerve is characterized by relatively thick myelin layer. In contrast, in FIG. 14D, the HIFU-treated section of nerve appears disorganized and arrows 135 point to areas of myelin disruption. These longitudinal sections of HIFU-treated nerves, stained by H&E or Masson's trichrome, clearly show disruption of myelin sheaths and axons across fascicles of the nerve (arrows 133 in FIG. 14B and arrows 135 in FIG. 14D. The number of staining Schwann cell nuclei 139 are reduced in the HIFU-treated sections, as indicated by comparing FIG. 14B with the untreated nerve sections shown in FIG. 14A. The HIFU treatment could have caused apoptosis or necrosis of the cells.

Figure 15A:
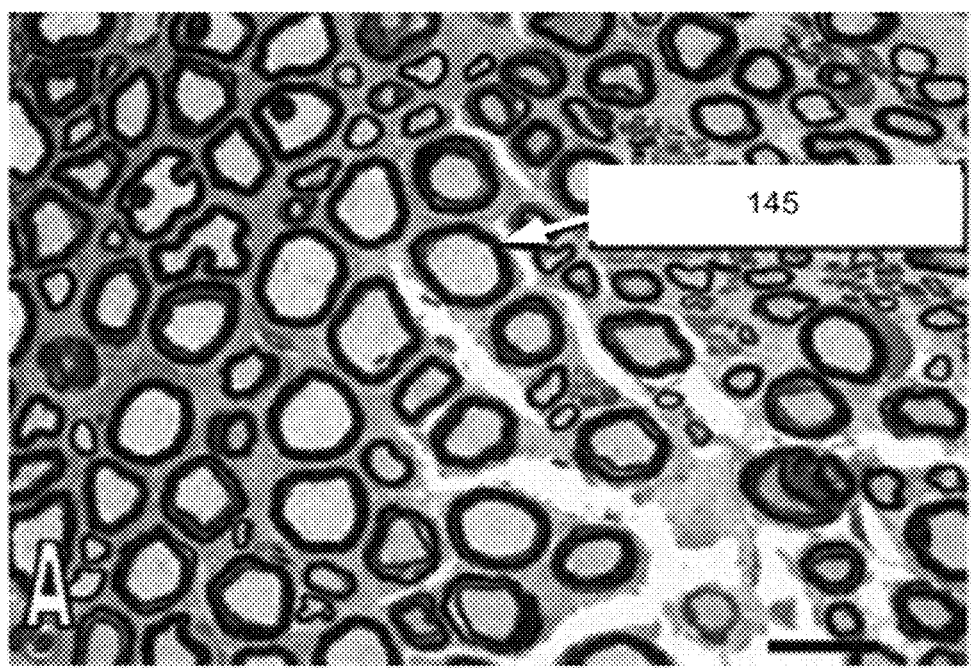
Figure 15B:
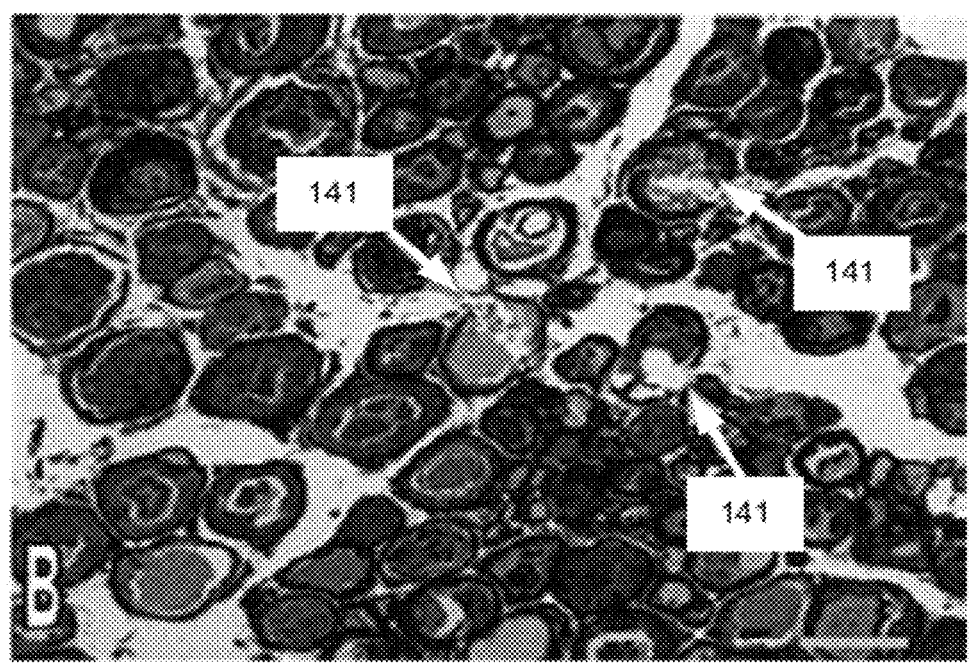

In the nerve cross sections stained with osmium and Richard's stain (FIGS. 15A and 15B), the HIFU treatment appeared to have caused axon swelling with myelin thinning and disruption, as indicated by arrows 141 in FIG. 15B, as compared to the untreated nerve sections shown in FIG. 15A. Most axons in the HIFU-treated sections showed abnormal dark staining within the axoplasm, which may have been due to disruption of the myelin sheath and accumulation of myelin in the axoplasm. The images of FIGS. 15A and 15B were generated using light microscopy. Richard's stain is methylene blue/azure II. The scale bars in the image are equal 16 μm. The untreated section of nerve in FIG. 15A shows a thick layer of myelin surrounding individual axons (see arrow 145), whereas in the HIFU-treated section of nerve in FIG. 15B clearly show areas of axonal demyelination and cell destruction.

FIGS. 16A and 16B show TEM images (magnification of 2300×) of axons of a normal, untreated section of a rabbit nerve (FIG. 16A) and a HIFU-treated section of the same rabbit nerve (FIG. 16B). It appears that the myelin layers surrounding HIFU-treated axons are disorganized and broken, allowing accumulation of myelin in the axoplasm of the nerve cells. The scale bars equal 6 μm. Note that FIG. 16A (normal, untreated nerve section) shows thick and organized myelin layers surrounding individual axons, while FIG. 16B (HIFU treated nerve section) shows disorganized and broken myelin layers surrounding individual axons.

The results of the first in vivo study indicate that HIFU at intensity of about 1480-1850 W/cm2 can effectively block conduction in the sciatic nerve complex of rabbits within 36 seconds+14 seconds (mean+SD). Therefore, the mean dose applied to the nerve and its adjacent tissue was about 49,300-62,900 J/cm2. This first empirical study also demonstrated the capability of commercially available high-resolution ultrasound imaging to identify the nerve complex and guide and monitor the HIFU treatment of the complex.

The biological mechanism of nerve block appears to be a combination of demyelination, axon disruption, and other structural damage to the nerve fibers, although the exact mechanism of HIFU bioeffects for neurolysis remains to be determined. Mechanisms of tissue damage by HIFU have been previously reported as being either thermal or mechanical. The large increase in temperature in the tissue at the site of the HIFU focus can lead to coagulative necrosis of the tissue. The blanching of the nerve at the site of the HIFU treatment, as well as the lesion in the surrounding muscle, was evidence of coagulative necrosis and thermal effect. It is also likely that cavitation (formation, growth, and collapse of micro-sized bubbles) plays a role in the structural damage evident from the histological examination. The high intensities (1480-1850 W/cm2) calculated at the focus of the HIFU transducer are likely sufficient to induce cavitation within the nerve and muscle tissue. The rupture of myelin sheaths of axons of the nerves (FIG. 15B) is likely the result of this mechanical action of HIFU. Boiling of ambient liquids can also result from the high temperatures generated in the tissue with HIFU application. Boiling bubbles can then act as nuclei for the generation of or enhancement of cavitation. Both cavitation and boiling are also believed to be involved in the enhancement of hyperechogenicity in the region of the ultrasound image corresponding to the HIFU focus. Although their involvement is assumed, the role of thermal and mechanical effects of HIFU in the conduction block of peripheral nerves is not fully understood at this time; and future studies are being planned to determine the prevalence of these mechanisms when using different doses of HIFU.

As noted above, histological results at 30 to 60 minutes after HIFU treatment show partial disruption of myelin and axons in the nerve. The abnormally dark staining of axoplasm in the osmium and Richard's stain cross sections (FIG. 15B) indicates disruption of myelin sheaths and accumulation of myelin in the axoplasm. TEM images in FIGS. 16A and 16B support this conclusion by showing the accumulation of disorganized and broken myelin in the axoplasm of nerve cells (FIG. 16B). Myelin disruption was evident from longitudinal nerve sections as well, shown by arrows 135 in FIG. 14D. HIFU also seems to disrupt the nuclei of Schwann cells, as can be seen by comparing Schwann cell nuclei 139 in FIGS. 14A and 14B. Schwann cells are responsible for myelination and remyelination in peripheral nerves. Without healthy Schwann cells, the nerve fibers are likely to have difficulty repairing myelin disruption caused by HIFU. Disruption of myelin and axons may lead to distal axon degeneration. Whether HIFU disruption of peripheral nerve is sufficient to lead to axon degeneration will be determined in long-term studies, currently underway.

To determine the long-term effects of HIFU treatment on the nerve complex, it is important to note the distinction between a force response to electrical stimulation distal to the HIFU treatment site and one proximal to the site. The initial disruption of the nerve by HIFU blocks the transmission of excited signals as they travel along axons from locations proximal to the treatment site to locations distal to the site. Therefore, stimulating the nerve proximal to the site will not result in a force response. However, the axon segments distal to the site are still viable after HIFU treatment and transmission along this area of the nerve is not blocked; a normal force response to stimulation is generated. If HIFU damage is irreversible, it could result in axon degeneration distal to the HIFU site over a period of days.

This first empirical study preliminary (acute rabbit study) provides a proof of concept for image guided HIFU therapy to treat the nervous system, to achieve a conduction block of a nerve. The study proved the sciatic nerve complex of rabbits could be treated using an ultrasound image guided HIFU device. While this first study indicates that HIFU therapy can be used to treat spasticity, it must be noted that determination of a threshold HIFU intensity and duration (dose) of treatment that will suppress function in the nerves is necessary for effective clinical application of HIFU to treat spasticity. Long-term studies will indicate whether the current protocol of HIFU provides a permanent block, caused by irreversible, axonal degeneration of the nerves, or only a temporary, reversible conduction block. Either case has clinical application. A permanent block would provide an effect essentially like severing the nerve, such that the spasticity or pain associated with a specific nerve would be absent indefinitely. Any voluntary function provided by this nerve would also be eliminated. Therefore, this effect would be useful primarily for patients who no longer have function, such as those with a complete transection of the spinal cord, yet have spasticity and/or pain. If the effect is reversible, it may indicate that there are protocols of HIFU treatment that could simply lessen the presence of spasticity or pain without hindering the voluntary function of a patient. This initial acute study showed the capability of very high HIFU doses of about 49,300-62,900 J/cm$^2$ to produce a complete conduction block of the rabbit sciatic nerve.

2$^{nd}$ Study: Verification of Irreversible Block of the Rabbit Sciatic Nerve Complex Treatment of spasticity sometimes requires permanent blockage of nerve function. The next study sought to determine a protocol of HIFU treatment that would irreversibly suppress the function in the nerve, to be used as a permanent treatment of patients with severe spasticity and no voluntary function. This study assessed the function of the nerve in response to electrical stimulation as much as 14 days after the HIFU treatment, assuming that if nerve function does not reappear after this time, HIFU has damaged axons of the nerve to such an extent that they have undergone Wallerian degeneration. Should function be restored at any time point within 14 days of HIFU treatment, this result is an indication that HIFU simply disrupted the nerve fibers enough to reversibly block conduction without subsequent axonal degeneration. As noted above, both cases have clinical utility for the treatment of patients with spasticity.

The ultrasound image-guided HIFU device that was used in the 1$^{st}$ study described above (see FIGS. 8A, 9C and 9E) was also used in the 2$^{nd}$ long-term study. There were only slight differences in the preparation of the animal and the application of HIFU to the nerve. To minimize the complications that could arise during the animal's recovery, no incisions were made in the rabbit skin. A new technique of preparing rabbit skin for transcutaneously HIFU therapy was developed. This technique involved shaving with an electric razor, 1-2 applications of depilatory cream (5 min each), and adding a thin layer of mineral oil between the polyacrylamide gel coupler and the skin. With each animal, the sciatic nerve complex was visualized using ultrasound imaging as a hyperechoic structure (Philips HDI-1000, CL10-5 probe), and HIFU treatment of 1500-1930 W/cm$^2$ was applied to the nerve. This range of intensities was determined previously to enable immediate visualization of a hyperechoic spot in the ultrasound image and complete block of the nerve, with minor collateral damage to adjacent tissue. For each rabbit, the protocol was to apply HIFU in 5 second intervals (10-20 seconds of total treatment) to the nerve complex until no force response of the plantarflexion muscles to electrical stimulation remained. A new package of needle electrodes and a fresh polyacrylamide gel coupler for the HIFU transducer were used for each animal. After completion of treatment, the animal was then allowed to recover from anesthesia. Each animal was monitored in the animal facility twice daily (for the first 5 days) and its force response to electrical stimulation of the sciatic nerve was measured with an endpoint at 15 days. The animal also had its force response measured at the intermediate time points of 2 and 7 days post HIFU treatment. Only minor anesthesia was used at these intermediate time points to control unwanted movement of the rabbit.

At the designated time endpoint of 15 days post-treatment, each animal was anesthetized, the nerve complex electrically stimulated percutaneously with near-nerve needle electrodes and the response of plantarflexion muscles was measured with a force transducer. The nerve complex was exposed and the force response to electrical stimulation proximal and distal to the HIFU site was measured. The animal was euthanized, and samples of the nerve and adjacent muscle were surgically harvested for future histological analysis.

The sciatic nerve complexes of the right legs of two New Zealand white rabbits have been treated using this protocol. One rabbit was treated with two 5-second exposures of HIFU at 1930 W/cm$^2$ (58% duty cycle; 19,500 J/cm$^2$), and the result was complete suppression of the force response (kick) to electrical stimulation (15 V). The hyperechoic spot was immediately visualized in the ultrasound image during each treatment. For one rabbit, after four different 5-second treatments of HIFU at 1500 W/cm$^2$ (58% duty cycle; 30,000 J/cm$^2$), the force response of the leg to electrical stimulation (15 V) was approximately 30% of the initial force response. It was concluded that the HIFU treatment should be terminated at that point to avoid formation of large lesions of muscle necrosis. The hyperechoic spot was visualized during these treatments, but only towards the end of each 5-second treatment. After 2 days, the HIFU-treated sciatic nerves of the animals were electrically stimulated and the force response of the plantarflexion muscles was measured. Complete block was observed in both animals, since no force response was indicated. Again, at 7 and 15 days post-treatment, the force response of both animals was measured and no response remained. Finally, at 15 days post-treatment, terminal surgery was performed for both animals. Upon exposure and stimulation of their sciatic nerves, both proximal and distal to the HIFU treatment site, no force response of the plantarflexion muscles remained, indicating axonal degeneration. These results indicated that the nerves remained blocked at 15 days post-treatment. Additionally, this duration of conduction block resulted in degeneration of distal axons of the nerve, indicated by the suppression of the force response to distal stimulation. The histological response of the nerves have not yet been evaluated to confirm this distal axonal degeneration. It is also important to note that Wallerian degeneration is used as an indication of irreversible suppression. Regeneration of nerves is possible, although investigating this would have required several months of post-HIFU observation of nerve conduction and function.

The long-term response of nerves is indicated by the light microscopy images in FIGS. 16C and 16D. The proximal portion of the nerve has axons that appear normal, as indicated in FIG. 16C. The distal portion of the nerve has several vacant sites, where axons were originally, indicating the degeneration of axons, as indicated in FIG. 16D. A total of 12 rabbits have been treated according to the protocol of the 2$^{nd}$ study, and the animals have survived to either 0, 7, 14, or 15 days post HIFU treatment. The mean HIFU treatment time to achieve complete conduction block of the sciatic nerve was 10.5±4.9 seconds. Complete conduction block remained in all treated nerves at their designated endpoints. The mean lesion volume was 1.6±1.1 cm$^3$.

3$^{rd}$ Study: Electrophysiological Acute Study of Partial Conduction Block

The goal of this study was to begin to explore the effects of HIFU of various doses on the peripheral nerve, particularly the physiological effects. It was hypothesized that a proportional relationship between HIFU dose and the suppression of the nerve conduction in response to electrical stimulation would be observed.

A single element, 3.5 MHz spherically curved HIFU transducer with a diameter of 23 mm and a focal length of 35 mm was used in this study. Two New Zealand white rabbits were anesthetized and their femoral nerves exposed. Pairs of stimulating and recording electrodes were hooked to the nerve in each rabbit at a distance of approximately 1.0 cm apart. The proximal stimulating electrode pair was connected to a Grass stimulator (S88), and the more distal recording pair was connected to an oscilloscope. The stimulator was set to deliver square pulses of 9 V amplitude and 6 ms duration at a rate of 3.8 pulses/s. Normal compound nerve action potentials (CNAP) were evoked at this same rate.

Continuous wave HIFU of increasing dose (increasing power levels at consistent duration of 5 seconds) was then applied to the nerve (between the two pairs of electrodes). The transducer was held stationary for durations of 5 seconds at each dose to allow a lesion to form. The transducer was coupled to the nerve using a water-filled plastic conical housing attachment as shown in FIG. 17. As indicated in this Figure, a probe 201 including the above transducer includes a water filled plastic cone 203 to serve as an acoustic coupling. The tip of plastic cone 203 was applied directly to nerve 82a so that HIFU was focused just beyond the tip of the plastic cone, thereby generating a lesion 205. The electrical power was recorded for each application of HIFU, and the corresponding CNAPs were recorded, and the waveforms were saved.

An upper portion of FIG. 18 (marked A) graphically illustrates the CNAP signal before HIFU application, while a lower portion of FIG. 18 (marked B) graphically illustrates the CNAP signals corresponding to application of HIFU of 7200 J/cm$^2$. FIG. 19 shows the suppression of the signal amplitude as HIFU of increasing dose was applied. HIFU application produced suppression of the signal. As the dose increased, the suppression was more pronounced (a maximum decrease of amplitude by 87%). The nerve appeared damaged and discolored after HIFU treatments at doses of 6250 J/cm$^2$ and above. The lesions corresponding to the HIFU application approximated the cross section of the nerves; however, the focal size of the HIFU beam did not allow equal distribution of energy across the entire nerve. It is important to note that the signal was not completely suppressed even after application of HIFU at higher doses. This remaining signal still enabled generation of a force response, albeit a weakened response. This result is indicative of a partial conduction block. Further studies using rats as the animal model are planned to verify these results. Rather than steadily increasing the HIFU dose applied to a single nerve, future studies will apply different doses of HIFU to different nerves so that effects can be better correlated with dose.

4$^{th}$ Study: Functional Investigation Acute Study of Partial Conduction Block The purpose of this study was to investigate the effects of different doses of HIFU on the rabbit sciatic nerve, particularly the force response of the plantarflexion muscles in response to stimulation of the nerve. It was hypothesized that higher doses of HIFU would lead to a greater suppression of the force response to electrical stimulation.

The ultrasound image-guided HIFU device used in the 1$^{st}$ and 2$^{nd}$ studies described above was also employed in the 4$^{th}$ study. The procedure used in this study was identical to that described in the 1$^{st}$ study, except that the HIFU transducer was held stationary during treatment, rather than being scanned across the nerve. Furthermore, the voltage threshold stimulus to produce a force response of the plantarflexion muscles was determined as a function of HIFU dose. The sciatic nerves of three rabbits (six nerves) were treated.

For all rabbits, as the dose of HIFU application was increased (by increasing the duration of HIFU application), the voltage threshold for the stimulation of plantarflexion muscle contraction (to approximately the same force level) also increased to a maximum of 100-300%. These results, graphically illustrated in FIG. 20, represent the response of one nerve, suggest a partial conduction block, since a much greater stimulus voltage was required for the desired muscle contraction. Additionally, the maximum force response of the plantarflexion muscles both before and after HIFU application was measured. The force was weakened after HIFU application, but unlike in the 1$^{st}$ study discussed above, the muscle response was not completely suppressed. Upon exposure of the nerve, the force response was measured when applying stimulation directly to the nerve, both proximal and distal to the site of HIFU treatment. For all six legs, the force response to proximal stimulation was lower than that from distal stimulation. The mean distal and proximal responses are shown in FIG. 21. These results seem to indicate a partial conduction block of the sciatic nerve. However, the small number of nerves treated and the variance of treatment times do not yield statistically significant results. These variable effects of HIFU application on the functional behavior of the nerve complex suggest a need for more thorough investigation of the range of axonal effects that may result from variable HIFU exposure parameters. It appears that HIFU is capable of producing both partial and complete conduction block of the rabbit sciatic nerve.

5$^{th}$ Study: Pig Electrophysiological Acute Study of Partial Conduction Block The purpose of this study was to continue investigating a range of HIFU doses on the electrophysiological and functional properties of peripheral nerves. The length of the pig femoral nerve allowed several HIFU applications on each nerve.

Sections of both femoral nerves of one pig were treated with 5-second applications of HIFU. An intraoperative, 5.7 MHz HIFU transducer with a titanium solid-cone applicator was used in this study. The same direct-contact approach as shown in FIG. 17 was used, except with a titanium applicator rather than a water-filled cone. The diagram in FIG. 22 shows the positions on one nerve where the HIFU treatments of various doses were applied. 7500 J/cm$^2$ was applied at location 207; 6250 J/cm$^2$ was applied at location 209; 5000 J/cm$^2$ was applied at location 211; and 3750 J/cm$^2$ was applied at location 213. FIG. 23 illustrates the HIFU induced lesions on one nerve using various doses of HIFU.

The plot in FIG. 24 shows the average amplitude of the CNAPs that were recorded from the nerves in response to electrical stimulation after each HIFU treatment, normalized to the initial amplitude of CNAPs before HIFU application. For both nerves, the amplitude of the action potentials increased with the initial HIFU treatments and eventually decreased after further applications at higher doses. For the left leg, additional 7500 J/cm$^2$ treatments were applied to the nerve in an attempt to suppress the signal further (total doses of 22,500 and 30,000 J/cm$^2$). The signal did begin to decrease, but did not completely disappear. Additionally, the force response to electrical stimulation remained, although it was weaker as the HIFU treatment progressed. Even when a significant lesion was visible on the nerve, the force response and CNAPs were not completely suppressed. Such behavior of the nerve is indicative of a partial conduction block due to HIFU treatment. The variability of the HIFU effects are likely due to the focal size of the HIFU beam employed, which did not provide uniform distribution of energy across the entire cross section of the nerve.

Preferred HIFU Therapy Device Designs Based on the Results of the Empirical Studies Based on the empirical studies, HIFU therapy probes to be utilized to achieve permanent neural blockage will preferably be a HIFU transducer whose focal cross-sectional area of the HIFU beam is sufficiently great to enable equal distribution of the energy across an entire nerve being treated. One design criteria to achieve this larger focal region will be designing HIFU transducers to have medium focusing characteristics, rather than the strong focusing characteristics. The HIFU transducer having strong focusing characteristics that was used in the above empirical studies provided a HIFU focus with a cross section no greater than 1 mm, as shown in FIGS. 13A and 13B. Unless the cross section of the nerve to be treated is much smaller than 1 mm, there may not be a consistent dose received by different portions of the nerve. To develop a HIFU transducer for targeting a specific nerve, the mean diameter and depth of nerves from a variety of different test subjects will be measured, to ensure that the HIFU transducers have sufficient focal length. As noted above, gel couplers having different standoff thicknesses can be used to obtain different depths of penetration into tissue with fixed focal length HIFU transducers. The focal length of the fixed focus to HIFU transducer is controlled by the radius of curvature of the transducer. Based on anatomical studies for a specific neural treatment site, the fixed focal length should be slightly greater than the depth of the nerve, so that the fixed focus will reach the deep edge of the nerve when a small standoff or gel coupling (~1 cm thick) is disposed between the HIFU transducer and the tissue. Preferably the focal region of the HIFU transducer designed to achieve a permanent conduction block in a nerve will have a focal width larger than the nerve diameter to enable the HIFU to completely encompass the nerve, as shown in FIG. 25. For a nerve diameter of 1-2 mm, a HIFU focal width of approximately 3 mm would be preferable. The following equation describes the relationship between the parameters of the transducer and the focal width (w):

$$w = 2.44 \left(\frac{l_f}{D}\right)\lambda$$

where $l_f$ is the focal length (radius of curvature), D is the diameter, and $\lambda$ is the wavelength of the ultrasound beam. For example, a 3 MHz transducer with a diameter of 3 cm and a focal length of 3 cm would have a theoretical focal width of 1.2 mm. By increasing the ratio of the focal length to the diameter (F-number) or by decreasing the frequency, the focal width will increase. A 1 MHz transducer with the same F-number would have a theoretical focal width of 3.7 mm. It is important to note that these theoretical values are typically larger than the actual measured values. The most accurate values are those measured from the pressure field of the HIFU beam, however theoretical values must be used for initial construction of the device. It is also possible to design an acoustic lens (typically aluminum) to attach to the face of the transducer that could defocus the beam slightly to produce the larger focal size. Specifying different frequencies, focal widths, focal lengths, diameters, and acoustic lenses, the resulting HIFU beam patterns will be determined using both theoretical analysis and computer simulation. The parameters of the HIFU transducer chosen will be those that produce the most optimal beam pattern. Output intensities preferably will range from about 50-2000 W/cm$^2$.

Different neural targets will require HIFU transducers with different focal lengths to reach the appropriate depth of the nerves into the body. Different nerves, located in different regions of the body, require different transducer characteristics. Another important design consideration is that any therapy transducer and imaging transducer employed exhibit an appropriate acoustic window, enabling ultrasound imaging and HIFU to adequately reach the target neural structure without disrupting other important anatomical structures, such as blood vessels. Targeting areas that have small windows for the propagation of ultrasound energy require both the HIFU and imaging probes to have small footprints or beam dimensions. For the treatment of peripheral nerves, such as the tibial or peroneal nerves, a preferred device will be able to image from the side or back of the thigh and treat from the back of the thigh (midway between hip and knee). There are areas where no major blood vessels are located that could provide the safest treatment paths.

Two HIFU devices that have been proposed for the application of HIFU therapy to the sciatic nerve of a rat are shown in FIGS. 25 and 26. Each device includes a HIFU transducer designed to have a focal region larger than the cross-sectional area of a sciatic nerve 227 of a rat 233, to ensure that only a single application of HIFU is required to treat the entire cross-sectional area of the nerve. FIG. 25 schematically illustrates a device for the ultrasound image guided remote (i.e., transcutaneous) application of HIFU, including a HIFU transducer 221, an imaging transducer 225, a frame 223 (for ensuring the spatial orientation between the therapy transducer in the imaging transducer remains unchanged once an icon corresponding to the focal region of the HIFU transducer is introduced into an ultrasound image generated by the imaging transducer), and a convex-shaped water standoff 231 (a polyurethane membrane inflated with degassed water) attached to the face of the transducer. Standoff 231 acoustically couples the HIFU transducer to the lateral hamstring muscle and can be inflated to a desired height to enable positioning of the focus on the nerve without having to reposition the HIFU therapy probe (which is coupled to the frame). A constant flow of water through the standoff enables cooling of the transducer as well. Imaging transducer 225 can be implemented using a high-resolution imaging probe (preferably CL10-5, Philips HDI-1000TH), so that the HIFU focus will be in the image plane.

FIG. 26 schematically illustrates a HIFU device for the direct-contact application of HIFU and includes HIFU transducer 211 and a plastic cone 235. Cone 235 is filled with degassed water and is attached to the face of the transducer to acoustically couple the HIFU transducer directly to the target (which requires an incision to enable access to the nerve). Cone 235 extends along the HIFU beam path to the focus so that the focal zone is just beyond the tip of the cone, which enables visual guidance of the HIFU treatment to the nerve. Several different types of conic attachments can be used for direct contact HIFU therapy of neural structures. Hydrogel cones, aluminum cones, water filled cones, and titanium cones can be beneficially employed.

Significantly, focal region 229 provided by HIFU transducer 211 is larger than the cross-sectional area of the nerve to the HIFU transducer has been designed to treat. As a result, energizing the HIFU transducer will produce a lesion larger in cross-sectional area than the nerve, so that the nerve can be completely blocked with only a single application of HIFU.

FIG. 27 schematically illustrates a HIFU therapy probe 237 specifically designed to treat a neural structure 249. Probe 237 includes a HIFU transducer 241 that has been specifically designed to have a focal region 247 larger in size than a cross-sectional area of neural structure 249. A power lead 239 electrically couples probe 237 to a power supply (not shown). A standoff 243 acoustically couples HIFU transducer 241 to a patient's dermal layer 76. As discussed above, standoff 243 can be implemented using a fluid-filled sack or by hydrogel coupling. Manipulating a volume of fluid in standoff 243 when the standoff is implemented as a fluid filled sack will enable focal region 247 to be moved relative to neural structure 249 without requiring probe 237 to be moved. Also as noted above, when standoff 243 is implemented as a hydrogel coupling, hydrogel couplings of different sizes can be used to vary the depth to which focal region 247 penetrates beyond dermal layer 76. While not specifically shown, it should be understood that probe 237 is preferably synchronized to an ultrasound imaging probe to achieve ultrasound image guided HIFU therapy of neural structures.

While targeting in the empirical studies was achieved using a frame to couple the imaging transducer and the ultrasound therapy transducer together, and using a tissue-mimicking phantom gel to introduce an icon (via a transparent overlay) representing the focal region of the HIFU transducer into an image generated by the imaging transducer, as noted above, other techniques can be employed. Other embodiments of the invention might instead incorporate tracking of the ultrasound focus using software controlled by position sensors on the imaging and HIFU transducers. Ultrasound contrast agents or specifically, labeled particles that bind to substances in the nerve can improve its initial detection. The incorporation of 3D ultrasound imaging into such embodiments will also improve the detection of the nerve complex and the estimation of its volume to plan a more localized and effective HIFU treatment. These improvements will enable individuals with relatively little experience in the sonography of nerve structure to identify and treat it.

Embodiments that enable a variable depth of focusing into the patient can be beneficially employed. These embodiments will use coupling methods employing variable volume fluid coupling medium (unlike the stiff polyacrylamide gel) to enable dynamic adjustment of the HIFU transducer with this medium. Alternatively, a HIFU array will enable electronic focusing at a range of depths, providing a more localized HIFU treatment to a nerve or other structure of interest, without affecting much of the adjacent tissue. For areas near sensitive tissue, such as blood vessels or the spinal cord, extremely localized treatment is important to prevent adverse effects.

Clinical Applications

As noted above, HIFU holds promise as a more cost-effective, lower risk treatment for severe spasticity. Higher HIFU intensities appear to completely block the nerve conduction, but intermediate intensities are likely to cause only minimal suppression. Either case has clinical application. A permanent block would provide an effect essentially like severing the nerve, so that the spasticity or pain associated with a specific nerve would be eliminated indefinitely. Any voluntary function provided by this nerve would also be eliminated. Therefore, this effect would be useful primarily for patients who no longer have voluntary function, such as those with a complete transection of the spinal cord, yet having spasticity and/or pain. Non-permanent blocks achieved with lower dosages can be used to reduce the spasticity without permanently hindering the voluntary function of a patient. Patients with cerebral palsy, multiple sclerosis, incomplete spinal cord injury, and traumatic nerve injury often retain voluntary function yet it is limited by the presence of spasticity. Partial or temporary suppression of conduction in the over-excited nerves could lessen the spasticity and possibly improve the mobility of the patients.

The empirical studies targeted and treated peripheral nerves that are often part of an overactive reflex between motor synapses in the muscle and signals generated in the brain or spinal cord. An alternative method to suppress this overactive activity is to apply HIFU treatment directly to the nerve roots as they extend from the spinal cord. These are very sensitive structures that are in close proximity to the spinal cord, and a more precise localized method of HIFU treatment, such as graded neurolysis, would be best suited for this procedure.

With respect to using HIFU as a treatment for pain, many clinical problems cause individuals to experience pain generated in sensory nerves. These nerves are often unnecessary for normal sensory functions, such as those associated with tumors. Pain is often associated with cancer. For example, pain associated with bone cancer is typically severe and is known to involve a unique sensitization of the nervous system. Rather than taking heavy doses of pain medications (i.e., morphine) that cause nausea and other undesired side effects, the HIFU therapy of sensory nerves can provide a non-invasive method to alleviate the pain associated with sensory nerves. By destroying the nerves that create the pain, the patient's quality of life is improved without drugs. Thus, one aspect of the present invention is to provide a palliative treatment for cancer.

Ultrasound guided HIFU can also be used as treatment of musculoskeletal injuries, by targeting musculoskeletal structures rather than nerves. Ultrasound guided HIFU therapy can be used to detect and treat musculoskeletal injuries including tears in tendons, ligaments, and cartilage. Ultrasound's use in injuries of the musculoskeletal system has been more limited to diffuse ultrasound of physical therapy range intensities (1-10 W/cm3).

One application of the present invention would be treating a nerve having a larger cross-sectional area larger than the focal region of the HIFU transducer by scanning the focal region from one edge of the neural structure to the opposite edge (see FIG. 9C). This scanning technique can be used to achieve relatively large volumes of affected tissue relatively quickly (for example, the empirical studies employed a scanning rate of about 0.5-0.6 mm/second with HIFU durations of about 36 seconds). Previous techniques for inducing necrosis in tumors via HIFU have required relatively long treatment times. Using this scanning technique, even large sized tumors could be treated in a matter of seconds or minutes. Prior art methods of using HIFU for tumor treatment report treatment times of several minutes to hours to achieve large volumes (greater than 1 cubic centimeter) of necrosis, because they rely on the formation of several individual lesions approximately 1 mm×1 cm stacked next to each other. The duration of HIFU to form each lesion may be 5 seconds, but the time between each lesion formation is about 2 minutes. This protocol leads to very long treatment times. The scanning method of the present invention can significantly decrease the time that patients have to undergo a HIFU procedure to achieve a comparable result.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for using a high intensity focused ultrasound (HIFU) probe to provide therapy to a peripheral nerve at a treatment site in a patient, the method comprising the steps of:
   (a) positioning, external to the body, (i) a HIFU therapy probe having a focal point, and (ii) an ultrasound imaging device in proximity to the peripheral nerve;
   (b) creating an image of the treatment site with the imaging device by generating a sequence of ultrasonic imaging pulses that propagate to the treatment site;
   (c) verifying the position of the focal point of the HIFU probe relative to the treatment site in the image created in step (b) using imaging ultrasound;
   (d) after said verifying, administering a dose of HIFU to the peripheral nerve to achieve a therapeutic effect; and (e) during said administering, synchronizing and pulsing an HIFU wave produced by the HIFU probe with respect to the imaging pulses such that the HIFU probe's focal point can be viewed in the image during treatment.

2. The method of claim 1, wherein the imaging ultrasound comprises three dimensional (3D) ultrasound.

3. The method of claim 1, wherein the imaging ultrasound comprises two dimensional (2D) ultrasound.

4. The method of claim 1, wherein the step of verifying the position of the focal point of the HIFU probe relative to the treatment site comprises the steps of:
 (a) energizing the HIFU probe using a power level sufficient to change an echogenicity of tissue proximate the focal point, but insufficient to achieve a therapeutic effect; and
 (b) using the imaging ultrasound to detect the change in echogenicity, thereby verifying the position of the focal point.

5. The method of claim 1, further comprising the step of delivering a blood soluble agent to the patient prior to administering the dose of HIFU.

6. The method of claim 5, wherein the blood soluble agent is an anesthetic.

7. The method of claim 1, wherein the step of administering the dose of HIFU to the peripheral nerve comprises the step of using a HIFU power output level ranging from about 50 to about 2000 W/cm$^2$.

8. The method of claim 1, wherein the step of administering the dose of HIFU to the peripheral nerve comprises the step of using a HIFU power output level ranging from about 1480 to about 1850 W/cm$^2$.

9. The method of claim 1, wherein step (c) includes (i) generating a synchronization pulse that establishes a timing reference point for generating the sequence of ultrasonic imaging pulses in step (b), and (ii) pulsing the HIFU probe after a given time delay from the synchronization pulse sufficient to shift noise from the HIFU pulse away from the treatment site.

\* \* \* \* \*